(12) United States Patent
Tran et al.

(10) Patent No.: US 10,617,441 B2
(45) Date of Patent: Apr. 14, 2020

(54) PERCUTANEOUS LATERAL RECESS RESECTION METHODS AND INSTRUMENTS

(71) Applicant: Vertos Medical, Inc., Aliso Viejo, CA (US)

(72) Inventors: Minh Tran, Westminster, CA (US); Randel Woodgrift, Los Gatos, CA (US); James M. Corbett, San Juan Capistrano, CA (US); Phillip A. Thompson, Aliso Viejo, CA (US); David P. Lalor, Jr., Aliso Viejo, CA (US)

(73) Assignee: Vertos Medical, Inc., Aliso Viejo, CA (US)

( * ) Notice: Subject to any disclaimer, the term of this patent is extended or adjusted under 35 U.S.C. 154(b) by 120 days.

(21) Appl. No.: 15/698,584

(22) Filed: Sep. 7, 2017

(65) Prior Publication Data

US 2018/0064461 A1 Mar. 8, 2018

Related U.S. Application Data

(60) Provisional application No. 62/384,435, filed on Sep. 7, 2016.

(51) Int. Cl.
*A61B 17/00* (2006.01)
*A61B 17/88* (2006.01)
(Continued)

(52) U.S. Cl.
CPC .. *A61B 17/320016* (2013.01); *A61B 17/1671* (2013.01); *A61B 17/1695* (2013.01);
(Continued)

(58) Field of Classification Search
CPC ........ A61B 17/320016; A61B 17/1671; A61B 17/1695; A61B 17/32002;
(Continued)

(56) References Cited

U.S. PATENT DOCUMENTS

| 7,993,378 B2 * | 8/2011 | Foley | A61B 17/02 |
| | | | 600/114 |
| 2005/0273167 A1 * | 12/2005 | Triplett | A61B 17/1671 |
| | | | 623/17.11 |

(Continued)

FOREIGN PATENT DOCUMENTS

| CH | 709203 A1 | 7/2015 |
| DE | 29703947 U1 | 6/1997 |

(Continued)

OTHER PUBLICATIONS

International Search Report dated Jan. 31, 2018, for PCT Application No. PCT/US2017/050560, filed on Sep. 7, 2017, 7 pages.

(Continued)

*Primary Examiner* — Jessica Weiss
(74) *Attorney, Agent, or Firm* — Cooley LLP

(57) ABSTRACT

The present disclosure is directed to devices, kits, and methods for treating lumbar spinal stenosis by at least partially decompressing a compressed nerve root. The method can include identifying the compressed nerve root and percutaneously accessing a region of a lamina located adjacent to the compressed nerve root. The method can also include forming a channel through the region of the lamina, wherein the channel can be formed medial to a lateral border of the lamina. Further, the method can include expanding the channel in a lateral direction.

22 Claims, 38 Drawing Sheets

(51) Int. Cl.

| | | |
|---|---|---|
| *A61B 17/56* | (2006.01) | |
| *A61B 17/32* | (2006.01) | |
| *B25B 23/14* | (2006.01) | |
| *A61B 17/16* | (2006.01) | |
| *A61B 17/34* | (2006.01) | |
| *A61B 17/3205* | (2006.01) | |
| *A61B 90/00* | (2016.01) | |

(52) U.S. Cl.
CPC .. *A61B 17/32002* (2013.01); *A61B 17/32053* (2013.01); *A61B 17/3403* (2013.01); *A61B 17/3421* (2013.01); *B25B 23/14* (2013.01); *A61B 17/1637* (2013.01); *A61B 2017/00261* (2013.01); *A61B 2017/00743* (2013.01); *A61B 2017/320056* (2013.01); *A61B 2017/320064* (2013.01); *A61B 2017/3425* (2013.01); *A61B 2017/3488* (2013.01); *A61B 2090/034* (2016.02); *A61B 2090/08021* (2016.02); *A61B 2090/376* (2016.02)

(58) Field of Classification Search
CPC .......... A61B 17/32053; A61B 17/3403; A61B 17/3421; A61B 17/1637; B25B 23/14
USPC ............... 606/79–85, 279; 600/201–249; 623/17.11–17.16
See application file for complete search history.

(56) References Cited

U.S. PATENT DOCUMENTS

| | | | | |
|---|---|---|---|---|
| 2006/0004369 | A1* | 1/2006 | Patel | A61B 17/1633 606/79 |
| 2008/0243117 | A1* | 10/2008 | Sharps | A61B 18/12 606/41 |
| 2010/0312103 | A1* | 12/2010 | Gorek | A61B 6/12 600/425 |
| 2010/0331883 | A1* | 12/2010 | Schmitz | A61B 10/0275 606/249 |
| 2011/0301647 | A1* | 12/2011 | Hua | A61B 17/7083 606/279 |
| 2015/0257784 | A1 | 9/2015 | Corbin et al. | |
| 2015/0342591 | A1* | 12/2015 | Bleich | A61B 17/1671 600/204 |

FOREIGN PATENT DOCUMENTS

| | | |
|---|---|---|
| DE | 102011088252 A1 | 6/2013 |
| WO | WO-2005/120401 A2 | 12/2005 |
| WO | WO-2005/120401 A3 | 12/2005 |

OTHER PUBLICATIONS

Written Opinion of the International Searching Authority dated Jan. 31, 2018, for PCT Application No. PCT/US2017/050560, filed on Sep. 7, 2017, 11 pages.

* cited by examiner

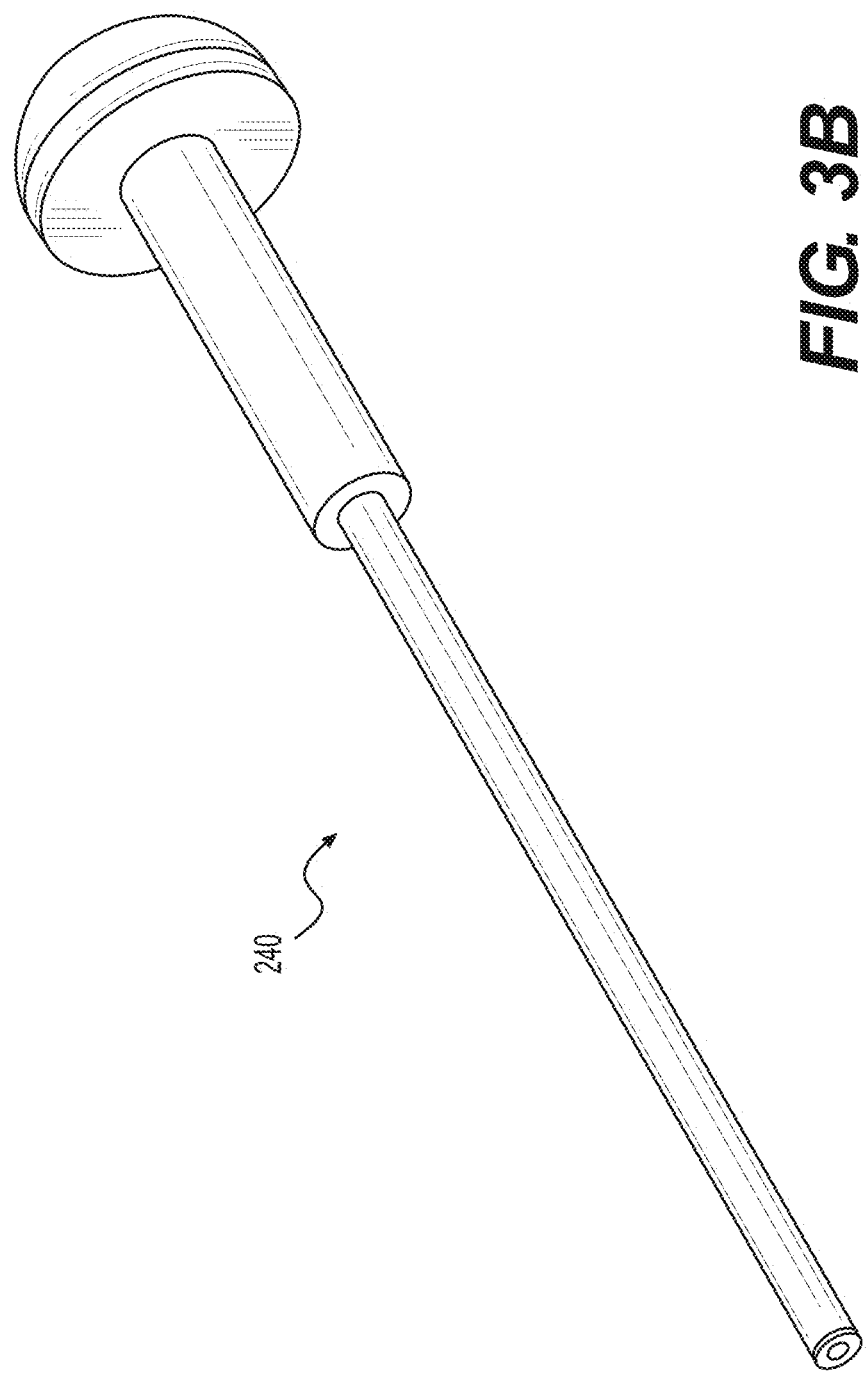

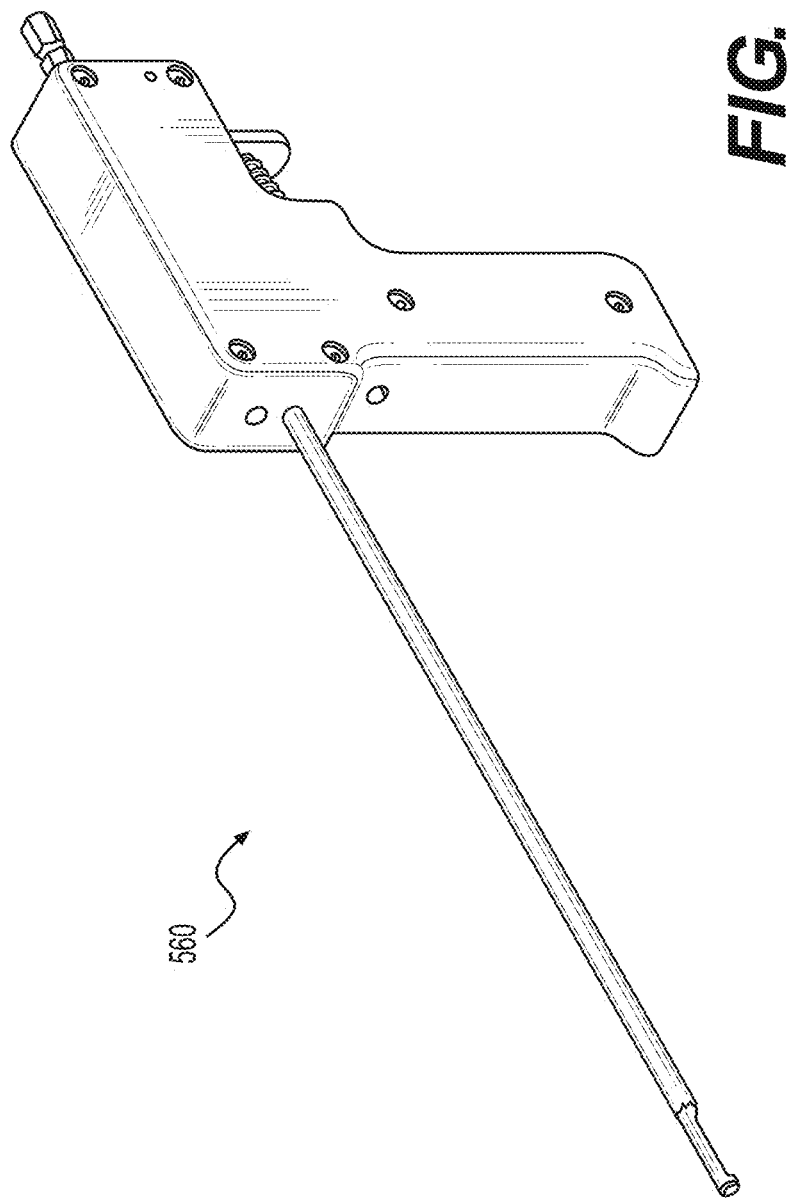

PERCUTANEOUS LATERAL RECESS RESECTION METHODS AND INSTRUMENTS

RELATED APPLICATIONS

This application claims the benefit of U.S. Provisional Application No. 62/384,435, filed Sep. 7, 2016, which is incorporated by reference herein in its entirety.

FIELD

This disclosure relates generally to the field of minimally invasive surgery. More specifically, the disclosure relates to methods and devices for treating spinal stenosis using percutaneous procedures.

BACKGROUND

Spinal stenosis can occur when the spinal canal narrows to compress the spinal cord or associated nerves roots. Spinal degeneration often occurs with aging, but may also be caused by disc herniation, osteoporosis, cancerous growth, or arise as a congenital condition. Spinal stenosis may also be caused by subluxation, facet joint hypertrophy, osteophyte formation, underdevelopment of spinal canal, spondylosis deformans, degenerative intervertebral discs, degenerative spondylolisthesis, degenerative arthritis, ossification of the vertebral accessory ligaments, or thickening of the ligamentum flavum. A less common cause of spinal stenosis, which usually affects patients with morbid obesity or patients on oral corticosteroids, is excess fat in the epidural space. The excessive epidural fat compresses the dural sac, nerve roots and blood vessels contained therein, often resulting in back and leg pain, or weakness and numbness of the legs.

Spinal stenosis may affect the cervical, thoracic, or lumbar regions of the spine. In some cases, spinal stenosis may be present in all three regions. Lumbar spinal stenosis can cause lower back pain, abnormal sensations in the legs or buttocks, and loss of bladder or bowel control.

Patients suffering from spinal stenosis are typically first treated with exercise therapy, analgesics, or anti-inflammatory medications. If these conservative treatment options fail, surgery may be required to decompress the spinal cord or nerve roots.

Traditional surgical procedures to correct stenosis in the lumbar region require a large incision be made in the patient's back. Muscles and other supporting structures are then stripped away from the spine, exposing the posterior aspect of the vertebral column. A portion of the vertebral arch, often at the laminae, may then be removed (laminectomy). The procedure is usually performed under general anesthesia. Patients can be admitted to the hospital for approximately five to seven days depending on the age and overall condition of the patient. Patients often require between six weeks and three months to recover from the procedure. Further, many patients need extended therapy at a rehabilitation facility to regain enough mobility to live independently.

Spinal stenosis can also occur due to compression of the intervertebral foramina, the passages between vertebrae through which nerves pass laterally from the spinal cord to the body. Foramina compression is often due to unwanted bone, ligament, or scar tissue formation in the passages. A foraminotomy can relieve the symptoms of nerve compression caused by foramen constriction. Traditional treatments include making an incision in the back of the patient's neck, then peeling away muscle to reveal the bone underneath, and cutting a small hole in the vertebra. Through this hole, using an arthroscope, the foramen can be visualized, and the impinging bone or disk material removed.

Much of the pain and disability after an open foraminotomy or laminectomy results from the tearing and cutting of the back muscles, blood vessels, supporting ligaments, and nerves. Also, because the spine stabilizing back muscles and ligaments are stripped and detached from the spine, these patients frequently develop spinal instability post-operatively.

Minimally invasive techniques offer the potential for less post-operative pain and faster recovery compared to traditional open surgery. Percutaneous spinal procedures can be performed with local anesthesia, thereby sparing the patient the risks and recovery time required with general anesthesia. In addition, there is less damage to the paraspinal muscles and ligaments with minimally invasive techniques, thereby reducing pain and reducing damage caused to the stabilizing structures.

Various techniques for minimally invasive treatment of the spine are known. Microdiscectomy is performed by making a small incision in the skin and deep tissues to create a portal to the spine. A microscope is then used to aid in the dissection of the adjacent structures prior to discectomy. The recovery for this procedure is much shorter than traditional open discectomies.

Percutaneous discectomy devices with fluoroscopic guidance have been used successfully to treat disorders of the disc but not to treat spinal stenosis directly. Arthroscopy or direct visualization of the spinal structures using a catheter or optical system have also been proposed to treat disorders of the spine including spinal stenosis, however these devices still use miniaturized standard surgical instruments and direct visualization of the spine similar to open surgical procedures. These devices and techniques are limited by the small size of the spinal canal and these operations are difficult to perform and master. In addition, these procedures are painful and often require general anesthesia. Further, arthroscopy procedures are time consuming and the fiber optic systems are expensive to purchase and maintain.

Current surgical procedures to treat spinal stenosis are often highly invasive, requiring significant removal of tissue to access the site and treat the stenotic lesion. A typical open procedure requires an incision be large enough to permit a surgeon to directly visualize the surgical site. Alternatively, an endoscope may be used in conjunction with a tissue retraction system to allow visualization and tissue removal through a large portal. Both procedures are highly invasive compared to the presently disclosed methods described herein. These traditional procedures often adversely affect the patient due to higher blood loss during the procedure, more damage to the tissue, or a larger incision. These factors may require longer hospital stay and longer rehabilitation time for the patient.

There are no known spinal procedures that employ percutaneous decompression of an exiting nerve root in the lateral recess area of the lumbar spine. Difficulties in performing a percutaneous procedure include lack of visualization of the surgical site, and wide variations in the anatomical region where bone is being removed. The variation (i.e. thickness and geometry) in the lateral aspect of the lamina where bone is being removed can make it difficult for surgical instruments to grasp, cut, and remove bone percutaneously. Hence, it remains desirable to provide simple methods, techniques, and devices for treating spinal stenosis and other spinal disorders without the disadvantages of conventional techniques.

SUMMARY

The surgical procedures and medical devices described herein overcome at least some of the limitations of the prior art. One aim of at least certain embodiments of the present disclosure is to treat symptoms of lumbar spinal stenosis by decompressing a nerve root. The procedure can be performed percutaneously with fluoroscopic imaging using anatomical landmarks to guide the instruments. Bone removal can be performed in a lateral recess area of a lamina, adjacent to the location of the nerve root. By removing at least part of the boney area, the nerve root can be decompressed to alleviate pain associated with lumbar spinal stenosis. The instrument set described herein can be specifically configured for use with the percutaneous procedure to safely access and remove bone from the lateral recess area of the lamina.

One aspect of the present disclosure is directed to a method for treating lumbar spinal stenosis by at least partially decompressing a compressed nerve root. The method may comprise identifying the compressed nerve root and percutaneously accessing a region of a lamina located adjacent to the compressed nerve root. The method may also comprise forming a channel having a longitudinal axis through the region of the lamina, wherein the channel can be formed medial to a lateral border of the lamina. Further, the method may comprise laterally extending the channel in at least one direction generally perpendicular to the longitudinal axis of the channel.

In some variations, the region of the lamina may include a lateral recess area and the method may further include extending the channel to breach the lateral border of the lamina. In some instances, the at least one of forming the channel and laterally extending the channel may be performed without direct visualization. The method may further comprise identifying at least one of a center of and an inferior border of a superior pedicle using fluoroscopic imaging. Moreover, in some variations, the method may further include making an incision at the intersection of a vertical line associated with the center of the superior pedicle and a horizontal line associated with the interior border of the superior pedicle. In some of these variations, the method may further include inserting a device through the incision, aligning the device substantially parallel to the superior pedicle, and anchoring the device to the lamina at a plurality of anchoring locations. Methods may further comprise forming the channel generally between at least two of the plurality of anchoring locations.

In some variations, the device may further comprise an access lumen, and the method may further comprise moving the access lumen to a different position without moving the plurality of anchoring locations. Moving the access lumen may also be performed without changing an orientation of the access lumen. Further, the access lumen may be restricted to a linear movement substantially orthogonal to the longitudinal axis of the channel. In some instances, the method may further comprise releasably engaging a lock to maintain a position of the access lumen relative to the anchoring locations.

According to another aspect, the present disclosure is directed to a method for resecting tissue from a lateral recess of a spine of a patient, whereby the spine can include a vertebrae having a lamina. The method may comprise anchoring a plurality of docking pins to the lamina, and slidably engaging an access portal with the plurality of docking pins. The access portal may have a distal end, a proximal end, first and second elongate members each configured to receive one of the plurality of docking pins, and a third elongate member configured to receive a surgical instrument. The method may further comprise sliding a first surgical device into the third elongate member, at least partially forming a hole in the lamina using the first surgical device, removing the first surgical device from the third elongate member, and inserting a second surgical device into the third elongate member. In some variations, the method may further comprise removing at least part of the lamina surrounding the hole using the second instrument while at least part of the plurality of docking pins resides within the first and second elongate members, and removing the second instrument, the access portal, and the plurality of docking pins from the patient. In some variations, the method may further comprise aligning at least one of the plurality of docking pins parallel to a superior pedicle of the spine.

In some embodiments, the method may further comprise, prior to slidably engaging the access portal with the plurality of docking pins, sliding a stylet into the third elongate member, sliding the access portal over at least one of the plurality of docking pins until the distal end of the stylet contacts the lamina, and removing the stylet from the third elongate member. In these variations, the method may further comprise slidably engaging the access portal with at least two of the plurality of docking pins. In some instances, the method may further comprise automatically disengaging the first surgical device when an anterior surface of the lamina is breached, and/or, in variations in which the first surgical device includes a trephine, coupling the trephine to a power source, sliding the trephine into the third elongate member of the trephine guide, and rotating the trephine relative to the third elongate member to form the hole in the lamina. In some instances, the method may further comprise using a feeler probe to verify that the hole extends generally through the lamina or to remove bone captured in the trephine and/or passing the second surgical device through the hole, wherein the second surgical device includes a rotating rongeur. In some embodiments, at least one of the plurality of docking pins may be engaged to the lamina before slidably engaging the access portal with the plurality of docking pins, and at least one of the plurality of docking pins may be engaged to the lamina after slidably engaging the access portal with the plurality of docking pins. Methods may further comprise restricting movement of the third elongate member along a linear path orthogonal to the plurality of docking pins and/or restricting orientation of the third elongate member to orientations parallel to at least one of the plurality of docking pins.

According to another aspect, the present disclosure is directed to a method of percutaneously decompressing a spinal nerve root of a patient. The method may comprise creating a single incision in the patient's back and accessing a posterior surface of a region of a vertebra located adjacent to the spinal nerve root via the single incision. The method may also comprise docking a plurality of anchoring pins to the region of the vertebra and creating a channel in the vertebra generally between at least two of the plurality of anchoring pins. The channel may have a first cross section and may be extended generally from the posterior surface to an anterior surface of the region of the vertebra. The method may also include selectively enlarging less than the whole first cross section of the channel to form a second cross section larger than the first cross section. In some variations, the first cross section may be symmetrical and the second cross section may be asymmetrical and/or the single incision may be located using an anatomical feature of a vertebra located superior to the vertebra located adjacent to the spinal nerve root.

According to another aspect, the present disclosure is directed to an access portal for use with a surgical procedure, the access portal having a distal end, and a proximal end. The access portal may comprise a housing, first and second elongate members, and a third elongate member. Each of the first and second elongate members may comprise a lumen therethrough and may be configured to receive a docking pin. The longitudinal axes of the first and second elongate members may be parallel to one another and a proximal end of each of the first and second elongate members may be coupled to the housing. The third elongate member may comprise a lumen therethrough and may be configured to receive a surgical instruction. A proximal end of the third elongate member may be movably coupled to the housing. The third elongate member may be movable laterally relative to the first and second elongate members such that a longitudinal axis of the third elongate member may be translatable in at least one lateral direction relative to the longitudinal axes of the first and second elongate members.

In some variations, a part of the access portal may comprise radiolucent material and/or the first and second elongate members may each comprise a steel alloy. The access portal may further comprise a guide adjuster configured to adjust the length of the surgical instrument extending beyond the third elongate member. In some instances, the surgical instrument may include at least one of a stylet, a trephine, and a feeler probe. Moreover, the surgical instrument may be a rongeur having a rotatable outer cannula surrounding a longitudinally displaceable rod having a distally located hook. In some embodiments, at least one of the first, second, and third elongate members may be removably attached to the housing and/or at least one of the first and second elongate members may be rigidly attached to the housing. In some variations, the access portal may further comprise a longitudinal axis, and the longitudinal axis of the access portal and the longitudinal axis of the third elongate member may be co-linear.

According to another aspect, the present disclosure is directed to an access portal for use in a surgical procedure, and the access portal may comprise a housing comprising a body and an actuator, a first elongate member, a second elongate member, and a third elongate member. A proximal end of the first elongate member may be coupled to the housing and the first elongate member may be configured to receive a first docking pin. A proximal end of the second elongate member may be coupled to the housing and a second docking pin may be positioned within the second elongate member and releasably coupled to the housing. The third elongate member may be coupled to the actuator, and the actuator may comprise a first position in which the third elongate member is fixed relative to the body and a second position in which the third elongate member is movable relative to the body.

In some embodiments, the body may further comprise first and second slots and the third elongate member may be positioned through the first and second slots. In some of these embodiments, the body may further comprise a third slot, and the actuator may be at least partially positioned through the third slot. In some variations, the body may further comprise a proximal surface, a distal surface, and a side surface, and the first, second, and third slots may be formed in the proximal, distal, and side surfaces, respectively. The first slot may be configured to allow movement of the third elongate member in a lateral direction, in a medial direction, or in both lateral and medial directions. In some variations, the actuator may comprise a disc-shaped dial. In some of these variations, rotation of the actuator may move the actuator between the first and second positions. Moreover, in some variations, the second docking pin may be releasably coupled to the housing using a fastener. In some access devices, the body may comprise a proximal surface and a distal surface, and the first and second elongate members may extend distally from the distal surface. In some of these access devices, the body may further comprise a slot on the distal surface, and the first and second elongate members may be coupled to the housing on opposite sides of the slot. In some instances, the access portal may further comprise a depth guide adjuster.

According to another aspect, the present disclosure is directed to a kit for use in a surgical procedure. In some variations, the kit may comprise an access portal and a trephine. The access portal may comprise a first elongate member, a second elongate member, a third elongate member, and a depth guide adjuster. The first and second elongate members of the access portal may be configured to receive first and second docking pins and the third elongate member may be configured to receive a surgical tool. The trephine may comprise an elongate member, a hub, and a two-way clutch operably coupling the elongate member and the hub. Rotational movement may be transmitted from the hub to the elongate member through the two-way clutch when a compressive force is applied to the hub and when a tensile force is applied to the hub.

In some variations, the two-way clutch may comprise a neutral configuration, a first engaged configuration, and a second engaged configuration, and rotational movement may not be transmitted from the hub to the elongate member when the clutch is in the neutral configuration. In some instances, the two-way clutch may be in the first engaged configuration when a compressive force is applied to the hub and/or in the second engaged configuration when a tensile force is applied to the hub. In some embodiments, the kit may further comprise a bone ejector, a feeler probe and a ronguer, and the bone ejector, the feeler probe and the rongeur may be configured to be at least partially slidably positioned within the third elongate member of the access portal. The kit may further comprise first and second docking pins.

According to another aspect, the present disclosure is directed to a kit for use in a surgical procedure and the kit may comprise an access portal, a trephine, a bone ejector and a rongeur. The access portal may comprise a housing and an elongate member coupled to the housing. The housing may comprise a body and an actuator and the elongate member may be rotatably coupled to the actuator. Rotation of the actuator in a first direction may lock the position of the elongate member relative to the body and rotation of the actuator in a second, opposite direction may allow lateral movement of the elongate member relative to the body. In some variations, the access portal may further comprise first and second docking pin guides configured to receive first and second docking pins. In some of these variations, rotation of the actuator in the second, opposite direction may allow lateral movement of the elongate member relative to the first and second docking pin guides. Moreover, in some embodiments, the elongate member may be configured to receive at least a portion of the trephine, the bone ejector, the feeler probe, or the rongeur.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the present disclosure, as claimed.

BRIEF DESCRIPTION OF THE DRAWINGS

The accompanying drawings, which are incorporated in and constitute a part of this specification, illustrate embodiments of the present disclosure and together with the description, serve to explain the principles of the present disclosure.

FIGS. 3A, 3B, 3C, 3D, 3E, 3F, and 3G show various instruments, according to exemplary embodiments;

DESCRIPTION OF THE EMBODIMENTS

Reference will now be made to exemplary embodiments of the present disclosure, examples of which are illustrated in the accompanying drawings. Wherever possible, the same reference numbers will be used throughout the drawings to refer to the same or like parts.

The vertebral column (spine, spinal column, backbone) forms the main part of the axial skeleton, provides a strong yet flexible support for the head and body, and protects the spinal cord disposed in the spinal canal, which is formed within the vertebral column. The vertebral column comprises a stack of vertebrae with an intervertebral disc between adjacent vertebra. The vertebrae are stabilized by muscles and ligaments that hold each vertebra in place and limit their movements relative to adjacent vertebra.

Figure 1:
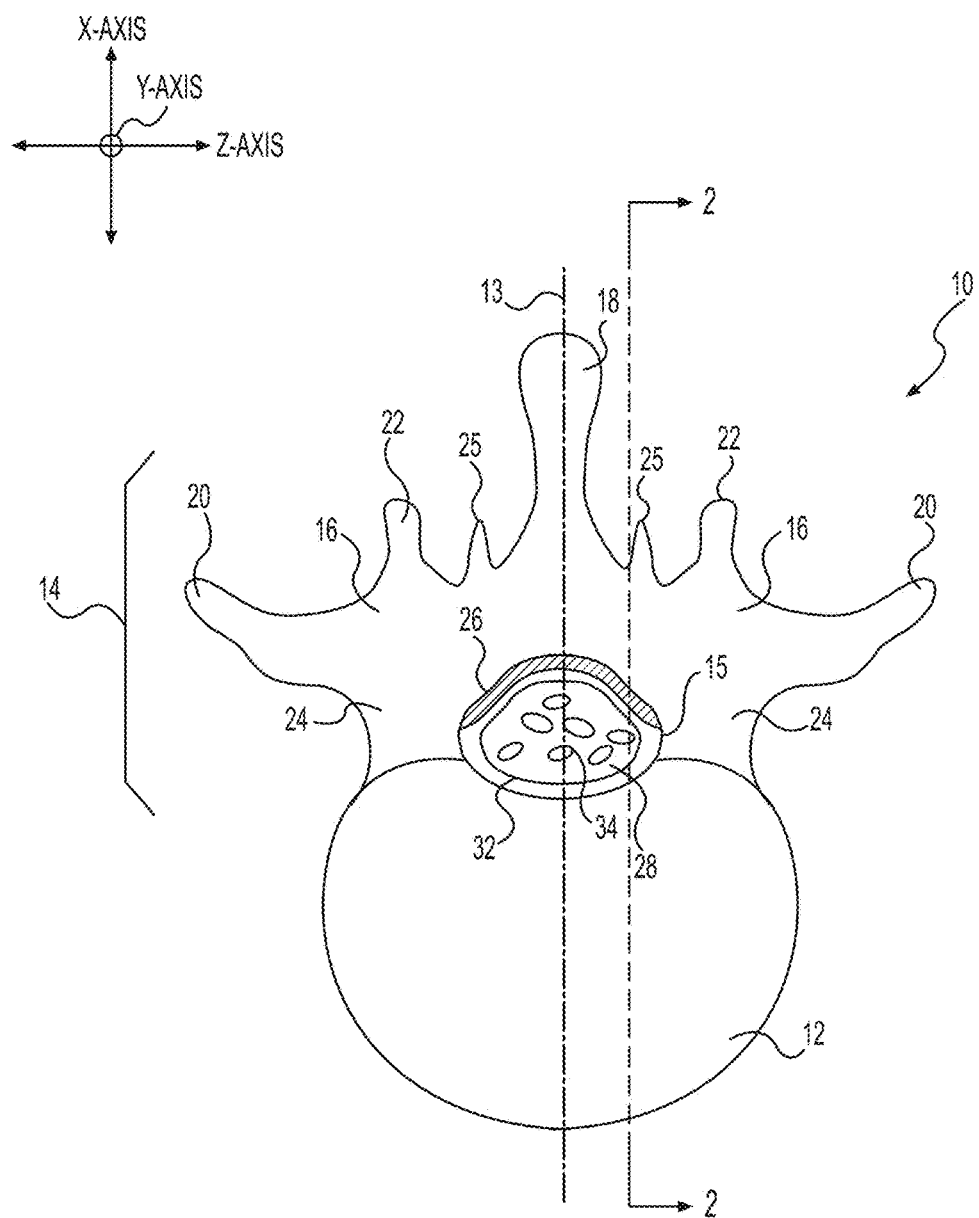
FIG. 1 shows a cross-sectional view of a spine viewed from the space between two adjacent vertebrae, showing an upper surface of one vertebra and the spinal canal.

As illustrated in FIG. 1, each vertebra 10 includes a vertebral body 12 that supports a vertebral arch 14. Vertebral body 12 has the general shape of a short cylinder and is located anterior to vertebral arch 14. Vertebral arch 14 together with vertebral body 12 encloses a space termed a vertebral foramen 15. A series of vertebral foramen 15 in adjacent vertebrae 10 along the vertebral column define the spinal canal. A median plane 13 generally divides vertebra 10 into two substantially equal lateral sides.

Vertebral arch 14 is formed by two pedicles 24 which project posteriorly to meet two laminae 16. The two laminae 16 meet posteriomedially to form a spinous process 18. At the junction of pedicles 24 and laminae 16, six processes arise. Two transverse processes 20 project posterolaterally, two superior articular processes 22 project generally superiorly and are positioned superior to two inferior articular processes 25 that generally project inferiorly.

Vertebral foramen 15 is generally an oval shaped space that contains and protects a spinal cord 28. Spinal cord 28 comprises a plurality of nerves 34 surrounded by cerebrospinal fluid (CSF) and an outermost membrane called a dural sac 32. The CSF-filled dural sac 32 containing nerves 34 is relatively compressible. Posterior to the spinal cord 28 within vertebral foramen 15 is the ligamentum flavum 26. Laminae 16 of adjacent vertebral arches 14 in the vertebral column are joined by the relatively broad, elastic ligamentum flavum 26.

Figure 2:
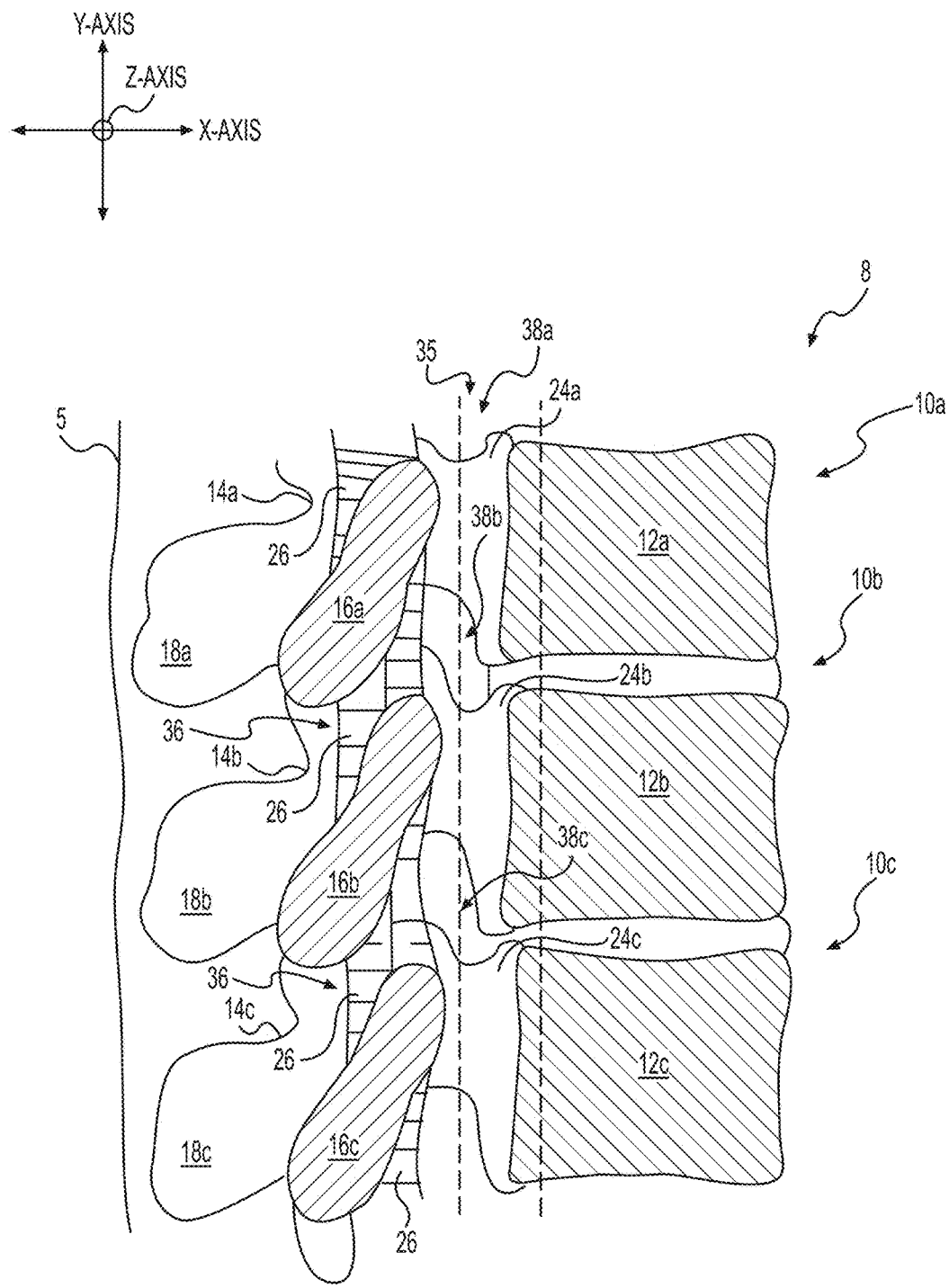
FIG. 2 shows a partial cross-sectional lateral view of a segment of a vertebral column.

FIG. 2 is a partial cross-sectional lateral view of a segment of a vertebral column 8, including a patient's back 5. The segment of vertebral column 8 illustrated in FIG. 2 includes three vertebrae 10*a*, 10*b*, and 10*c*. Each vertebra 10*a*, 10*b*, 10*c* includes a vertebral body 12*a*, 12*b*, 12*c*, that supports a vertebral arch 14*a*, 14*b*, 14*c*, respectively. Vertebral body 12*a*, 12*b*, 12*c* is anterior to vertebral arch 14*a*, 14*b*, 14*c*, respectively. Each vertebral arch 14*a*, 14*b*, 14*c* together with vertebral body 12*a*, 12*b*, 12*c*, respectively, encloses a series of vertebral foramen (not shown) that partially define a spinal canal 35 (indicated as dashed lines) that runs along the length of vertebral column 8. Spinal canal 35 contains a spinal cord (not shown).

As previously described, each vertebral arch 14*a*, 14*b*, 14*c* includes two pedicles 24*a*, 24*b*, 24*c*, which project in generally posterior directions to meet two lamina 16*a*, 16*b*, 16*c*, respectively. In this view, one pedicle has been removed from each vertebra 10*a*, 10*b*, 10*c* and only the cross-section of one lamina 16*a*, 16*b*, 16*c* is visible. The two lamina 16*a*, 16*b*, 16*c* meet posteriomedially to form the spinous process 18*a*, 18*b*, 18*c*, respectively.

Lamina 16*a*, 16*b*, 16*c* of adjacent vertebra 10*a*, 10*b*, 10*c* are connected by ligamentum flavum 26 (shown in cross-section). The relatively elastic ligamentum flavum 26 extends almost vertically from superior lamina to inferior lamina of adjacent vertebrae. Thus, ligamentum flavum 26 spans an interlaminar space 36 (i.e., space between laminae of adjacent vertebrae).

Each lamina 16*a*, 16*b*, 16*c* comprises a relatively broad flat plate of bone that extends posteromedially and slightly inferiorly from pedicles 24*a*, 24*b*, 24*c*, respectively. Along the length of vertebral column 8, the lamina 16*a*, 16*b*, 16*c* can overlap, with each lamina substantially parallel to and at least partially overlapping the adjacent inferior lamina. Further, the adjacent substantially parallel laminae are separated by the intervening ligamentum flavum 26 and interlaminar space 36. For instance, lamina 16*a* is substantially parallel to and partially overlaps adjacent inferior lamina 16*b* and is separated from lamina 16*b* by ligamentum flavum 26 and interlaminar space 36.

Between every pair of adjacent vertebrae there are two lateral apertures. As shown in FIG. 2, an intervertebral foramen 38*b* resides between vertebrae 10*a* and 10*b*. Intervertebral foramina 38*a*, 38*b*, 38*c* are also called neural foramina and can be abbreviated as IV foramina. Intervertebral foramina 38*a*, 38*b*, 38*c* allow for the passage of various organs (not shown) into and out of spinal canal 35. These organs can include nerves (e.g., nerve root, dorsal root ganglion, recurrent meningeal (sinu-vertebral) nerves), blood vessels (e.g., spinal artery of the segmental artery, communicating veins between the internal and external plexuses), or ligaments (e.g., transforaminal).

The size, orientation and/or shape of intervertebral foramina 38*a*, 38*b*, 38*c* can vary along the vertebral column due to location (e.g. cervical, thoracic, lumbar) along vertebral column 8, pathology, spinal loading, or posture. In some instances, foramina 38 can be at least partially occluded by arthritic degenerative changes and space-occupying lesions like tumors, metastases and spinal disc herniations. Some degenerative conditions of the spine cause narrowing of foramina 38. One aim of certain embodiments of the present disclosure is to provide a method and a device for treating foraminal stenosis using lateral recess resection.

Devices

In some embodiments, the procedure can use anatomical landmarks to safely couple an access portal to a posterior aspect of the lamina, away from any vital nerves that could be accidentally damaged. The access portal can be generally anchored in place using a plurality of anchoring pins, as described below in more detail. Moreover, the access portal can be translated laterally, in one or more directions, generally over the posterior aspect of the lamina. Thus, the access portal can allow one or more instruments to be selectively relocated generally within defined bounds at the surgical site. Furthermore, instead of removing bone starting from an edge of a lateral aspect of the lamina, as done in open procedures, the current method can use a medial to lateral or "inside-out" approach.

Figure 4A:
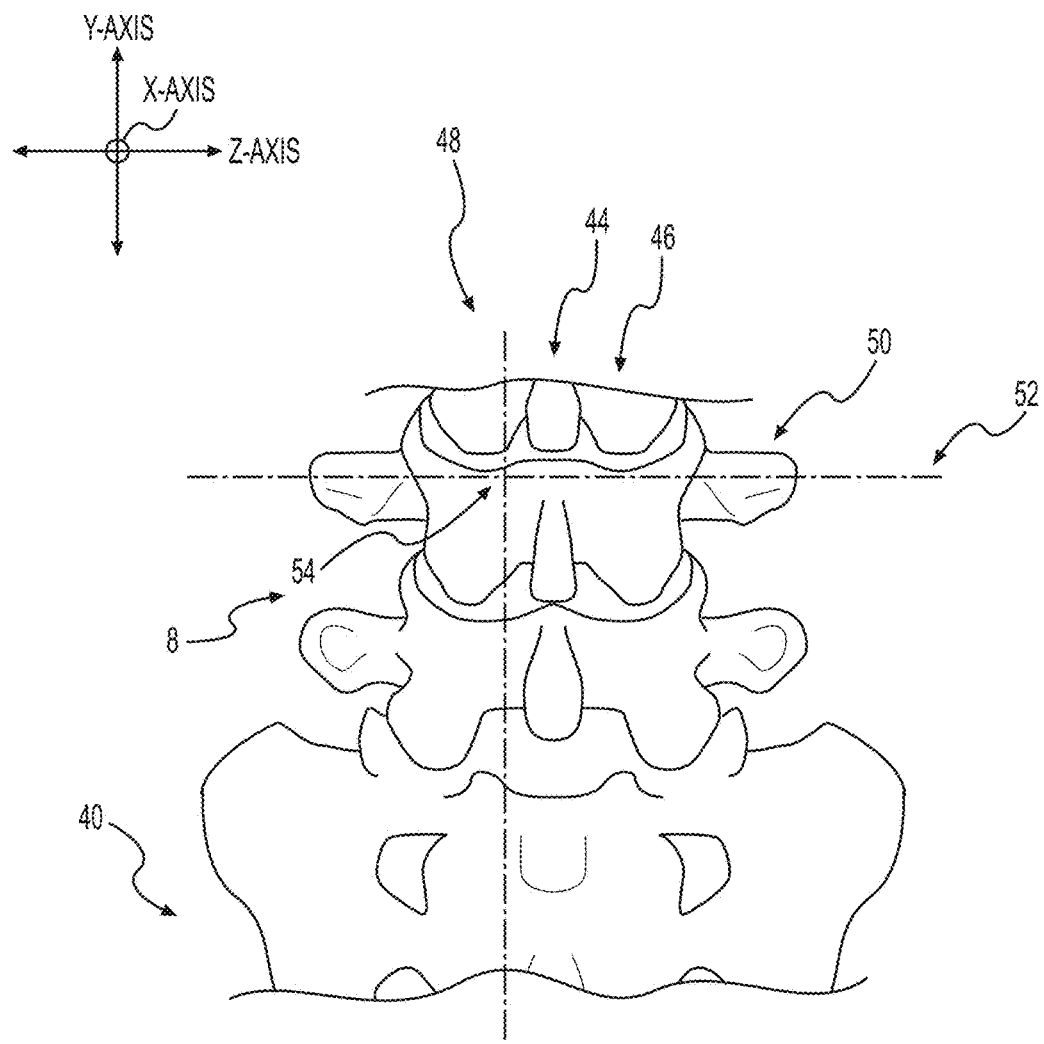
FIGS. 4A and 4B show posterior views of a segment of a vertebral column, according to an exemplary embodiment.
Figure 4B:
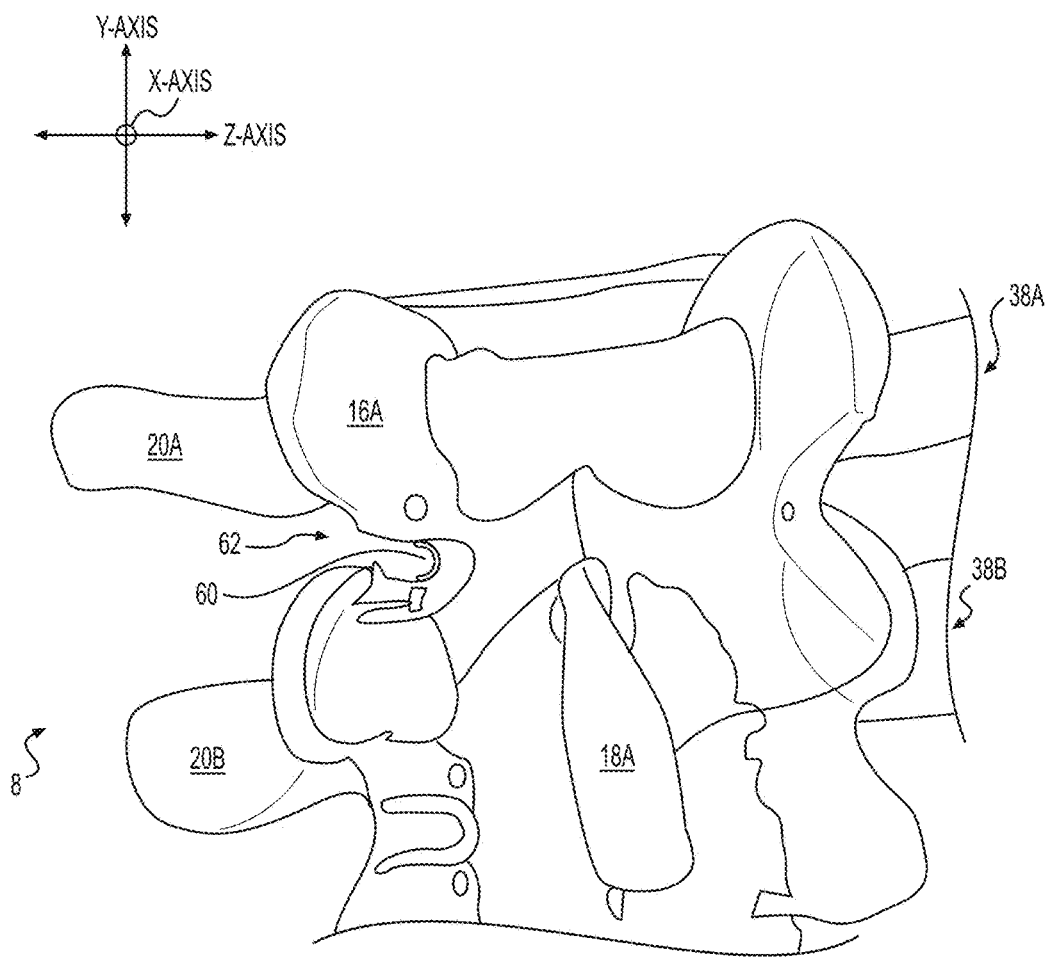

In this approach, an initial instrument can be used to form a channel 60 through lamina 16*a* starting on the posterior side of lamina 16*a* and just medial to the lateral border of lamina 16*a*, as shown in FIG. 4B. By forming channel 60 through lamina 16*a*, a predictable geometry can be created whereby subsequent instrument(s) can enter channel 60 and grasp, cut, or remove bone laterally. Such steps can be repeated until the lateral aspect of the lamina 16*a* is breached, forming a slot 62.

This approach can mitigate the variation in anatomical geometry of the lamina and allow specially designed instruments to cut and remove bone in a predictable manner. The instruments used in the procedure can safely access the surgical site and remove bone from the lateral aspect of the lamina. In some embodiments, the instruments can include a docking pin 250, a handle 240 for docking pin 250, an access portal 260, a trephine 530, a bone ejector 550, a feeler probe 555, and a rongeur 560, as shown respectively in FIGS. 3A-3G. Structural and functional descriptions of these instruments will be provided below in the context of a surgical method contemplated by the present disclosure.

Initially, a patient may be positioned to permit surgical access to their vertebral column 8 via their back 5. An imaging modality may then be used to visualize at least part of vertebral column 8. Imaging modalities can include PET, CAT, MRI, or other non-invasive imaging techniques. In some embodiments, fluoroscopy may be used to image at least part of vertebral column 8.

As shown in FIG. 4A, an imaging modality can be used to generate an image of part of vertebral column 8. For example, a fluoroscopic C-Arm (not shown) may be used to image a part of vertebral column 8. The image may, or may not, include a part of sacrum 40.

One or more anatomical features of vertebral column 8 can be identified. For example, in an anterior-posterior view, a center 44 of a superior pedicle 46 can be identified, as shown in FIG. 4A. Following identification of center 44, a vertical line 48 lateral to center 44 can be generated. It is contemplated that vertical line 48 could be created by placing an elongate device (not shown) medial to center 44. Vertical line 48 could be created using an edge of the elongate device.

It is also contemplated that an inferior border 50 of the superior pedicle may be identified. Following, an elongate device (not shown) could be placed inferior to inferior border 50. Based on the location of inferior border 50, a line 52 could be provided, as shown in FIG. 4A. For example, a C-Arm may be adjusted to provide an image of a lower endplate of a superior vertebra that appears as line 52. In an L4-L5 construct, the lower endplate of L4 can appear as single line 52, wherein line 52 is substantially horizontal.

Based on one or more anatomical features of vertebral column 8, an incision (not shown) in the skin of back 5 can be located. For example, a single incision can be located at an intersection 54 of line 48 and line 52. Following creation of the incision, one or more instruments may be inserted through the incision to access vertebral column 8. The incision may include a single cut having a length approximately equal to the outer diameter of the largest instrument to be passed through the incision. Smaller incisions may also be used.

In some embodiments, the lumbar spinal region of a patient may be surgically prepared with the patient positioned prone on a surgical table. Following fluoroscopic identification of the target spinal level, a stab incision approximately 12 mm in length may be made in the skin and through the underlying lumbar fascia. In other embodiments, a mark on the skin inferior and medial of a pedicle may be made. For example, the incision can extend about 6 mm superior and about 6 mm inferior from the mark. The rest of the procedure may be performed under live fluoroscopic imaging. As such, direct visualization of the bone, channel 60, slot 62, or other anatomical features may not be required for the methods of the present disclosure. It is also contemplated that another part of the spine or other bone structure could be treated using at least part of the following devices or methods.

Figure 5:
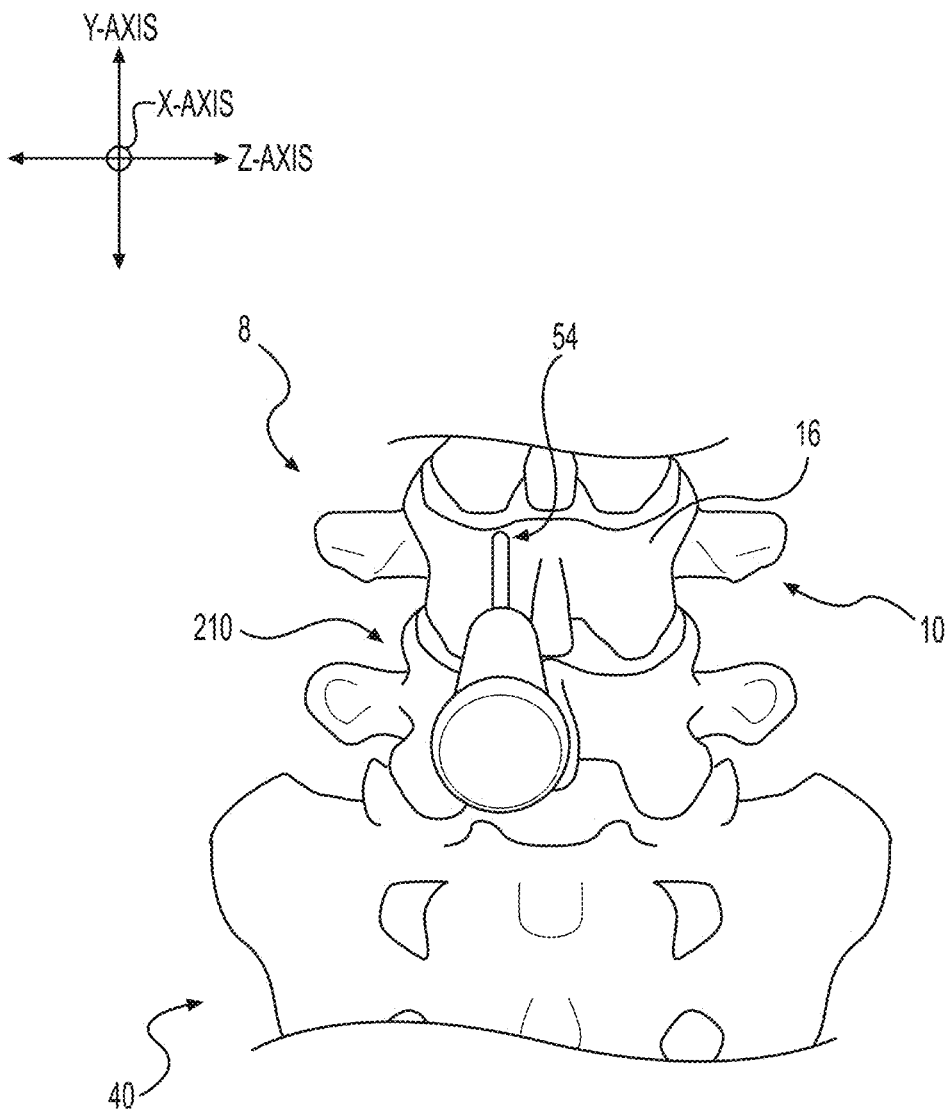
FIG. 5 shows a posterior view of a segment of a vertebral column, showing an instrument location according to an exemplary embodiment.

As shown in FIG. 5, a docking pin assembly 210 may be located at intersection 54. Docking pin assembly 210 may also be passed through the incision. In some embodiments, docking pin assembly 210 can be used to gain initial access to a posterior aspect of lamina 16 of vertebra 10. As described below, channel 60 may be created in lamina 16, wherein channel 60 may have a diameter of about 6 mm. In some embodiments, channel 60 may be enlarged toward a lateral recess, forming slot 62, undercutting the medial facet joint and decompressing the lamina.

Figure 8:
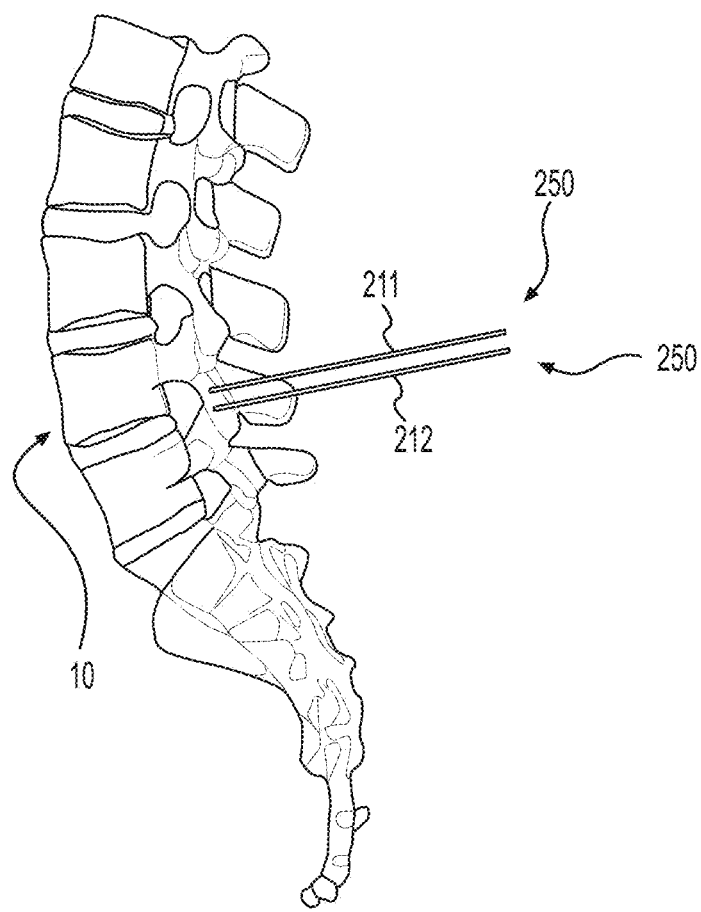
FIG. 8 shows a plurality of detached docking pins anchored to a vertebra, according to an exemplary embodiment.
Figure 26A:
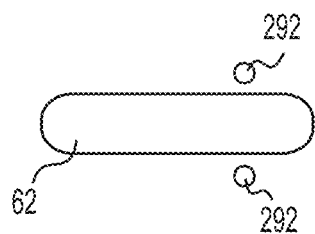
FIGS. 26A, 26B, 26C, and 26D show various slots formed within a lamina, according to exemplary embodiments.

Moreover, two or more docking pin assemblies 210 may be used. For example, a primary pin 211 may be anchored to a superior portion of lamina 16 while a secondary pin 212 may be anchored to an inferior portion of lamina 16 (FIG. 8). In addition, two or more docking pin assemblies 210 may each be located along a common straight line, such as, vertical line 48 (FIG. 4A). Such anchoring at multiple locations can provide a strong anchoring force sufficient to permit creation of slot 62 within lamina 16 (FIG. 4B). As described below, slot 62 can be located between the anchoring points of docking pin assemblies 210 (FIG. 26A). As shown in FIG. 4B, slot 62 can extend generally laterally and through an edge of lamina 16. Using a vertical incision with lateral motion can reduce pain and recovery time for the patient because the incision lies generally parallel to the majority of the musculature and any lateral movement within the incision merely displaces such tissue. In some variations, the slot may be about 3, 4, 5, 6, 7 or 8 mm wide, or in the range of about 3 mm (0.118 inches) to about 8 mm (0.315 inches), about 4 mm (0.157 inches) to about 6 mm (0.236 inches), or about 6 mm (0.236 inches) to about 8 mm (0.315 inches), for example, and in use may be positioned as close as possible to the spinous process. In some variations, the first docking pin may be positioned during the procedure in the runout of the spinous process, or in the transitional area between the spinous process in the lamina, such that the slot position is just lateral to the first docking pin. The slot length may be in the range of about 5 mm (0.197 inches) to about 22 mm (0.866 inches), about 10 mm (0.394 inches) to about 18 mm (0.709 inches), or about 12 mm (0.472 inches) to about 16 mm (0.630 inches), for example. In one further example, the slot dimensions are approximately 5 mm (0.197 inches)×15 mm (0.591 inches) or more depending on laminal size.

Figure 6:
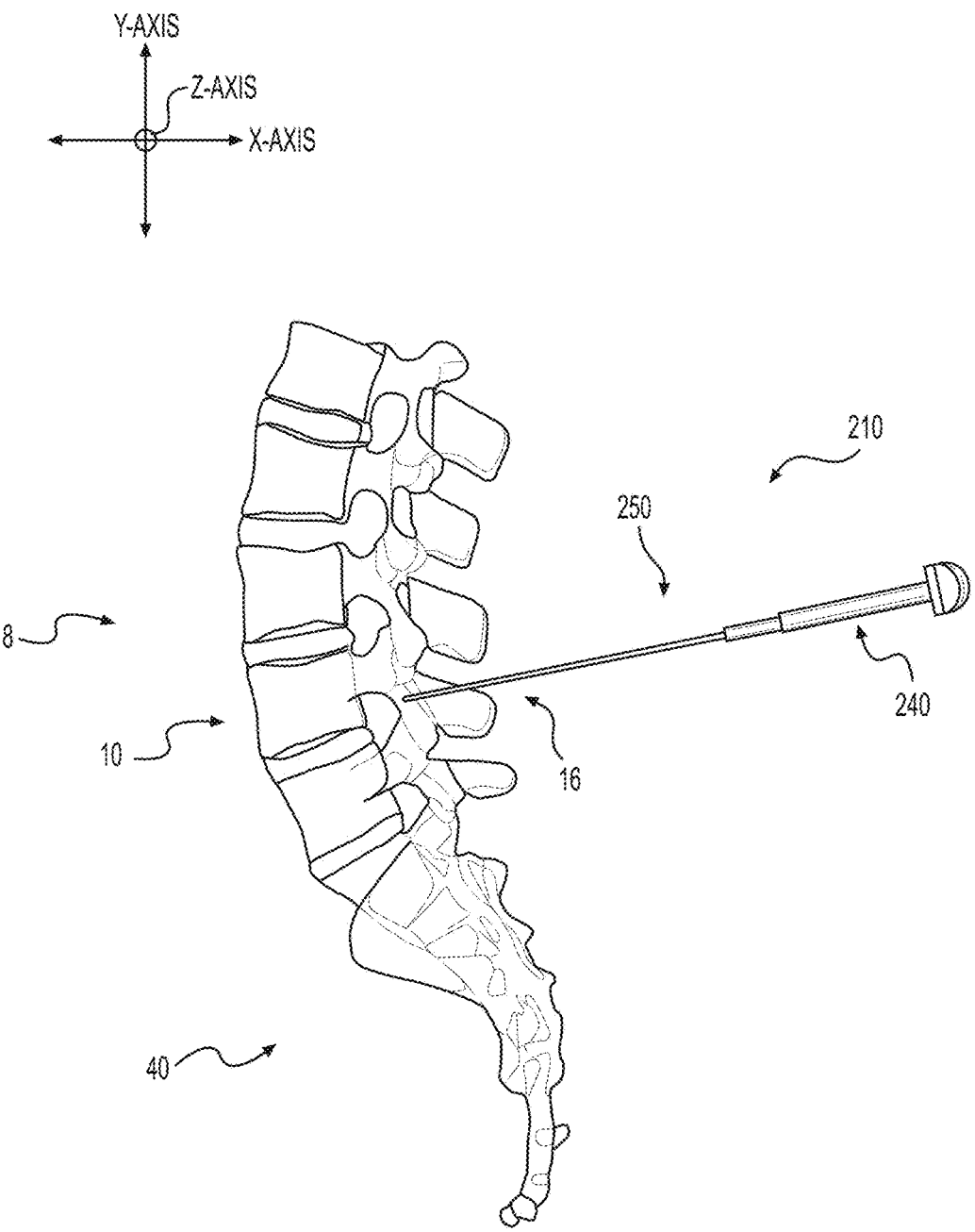
FIG. 6 shows a lateral view of a segment of a vertebral column, showing an instrument location according to an exemplary embodiment.

It is also contemplated that one or more docking pin assemblies 210 may be aligned with one or more anatomical features. For example, one or more docking pin assemblies 210 could be located inferior to a superior pedicle. Also, one or more docking pin assemblies 210 could be aligned substantially parallel to a superior pedicle, as shown in FIG. 6. In addition, one docking pin assembly 210 may be located superior or inferior to another docking pin (not shown) or pin 250. If necessary, the location or alignment of one or more docking pin assemblies 210 relative to one or more anatomical feature could be adjusted. Once properly located and aligned, additional force may be applied to one or more docking pin assemblies 210 to ensure that they are firmly anchored into lamina 16.

Figure 7A:
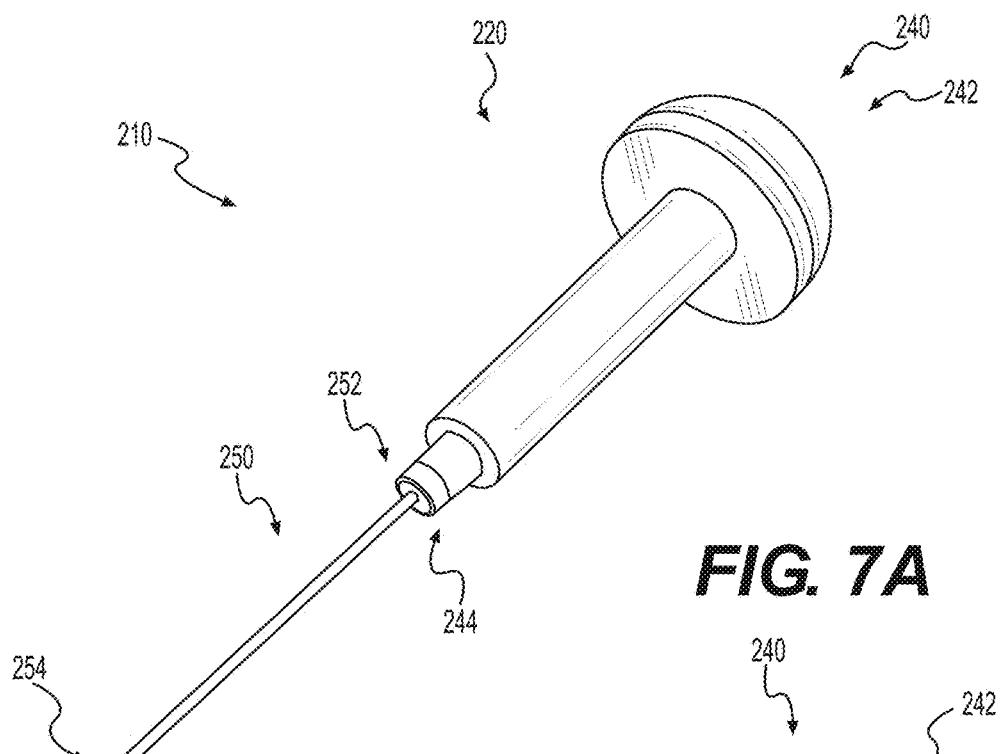
FIGS. 7A and 7B show, respectively, an attached and a detached docking pin, according to an exemplary embodiment.
Figure 7B:
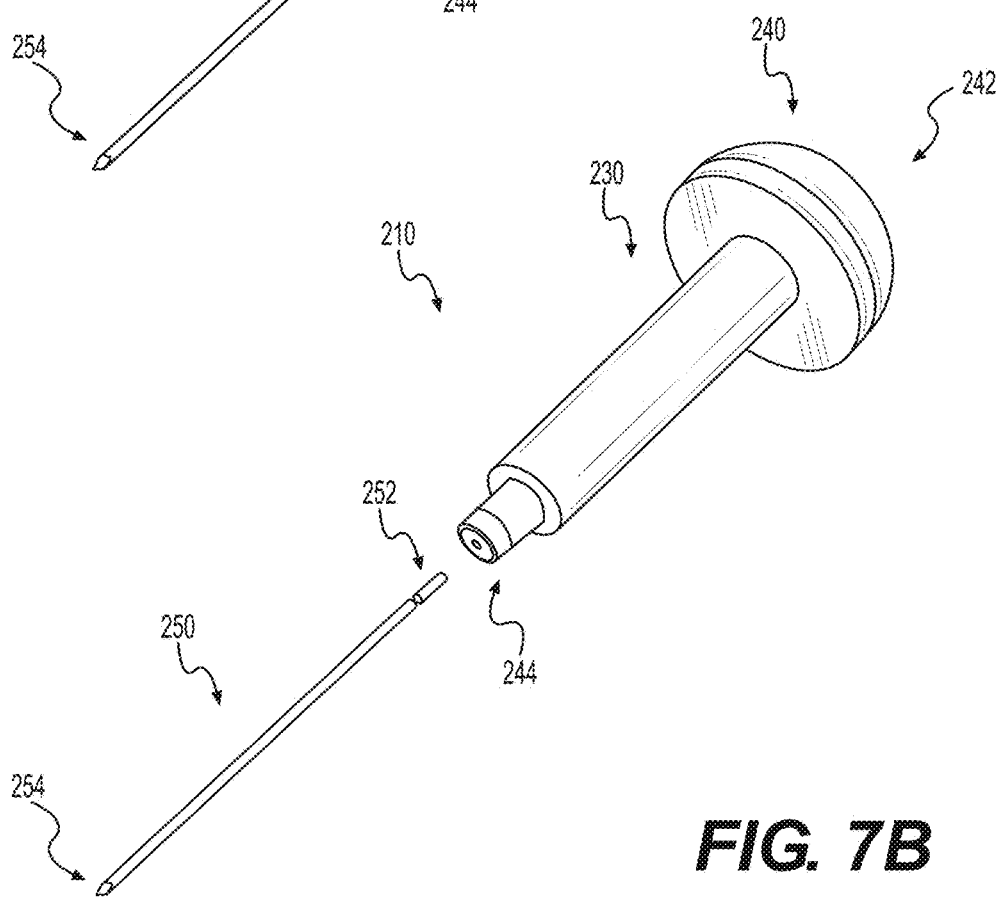

In some embodiments, docking pin assembly 210 can be detachable. FIGS. 7A and 7B depict docking pin assembly 210 in an attached configuration 220 and a detached configuration 230, respectively. Docking pin assembly 210 can include a handle 240 and a pin 250, wherein handle 240 and pin 250 can be configured to detach from each other. Handle 240 and pin 250 may each comprise a proximal end 242, 252 and a distal end 244, 254. In some variations, distal end 244 of handle 240 may be configured to detach from proximal end 252 of pin 250. It is also contemplated that distal end 244 and proximal end 252 could be configured for repeatedly releasably coupling, whereby handle 240 and pin 250 could be detached and attached one or more times. For example, the handle 240 may comprise a lumen or opening on a distal end 244 thereof into which proximal end 252 of pin 250 may be advanced. In some variations, proximal end 252 of pin 250 may comprise a notch or indentation that may engage with a raised portion or latch in the lumen of handle 240 to releasably couple pin 250 and handle 240. In other variations, the lumen may comprise threads that receive a threaded portion of proximal end 252 of pin 250. It should be appreciated that any suitable temporary or releasable fastener may be used to couple proximal end 252 of pin 250 to distal end 244 of handle 240. In some embodiments, handle 240 or pin 250 may include a locking system (not shown) configured to limit relative movement between handle 240 and pin 250.

In some embodiments, proximal end 242 of handle 240 can be configured to engage a mallet, a screwdriver, or other device to drive pin 250 into a boney structure. For example, a proximal surface of handle 240 may comprise an indentation, recess, or one or more slots sized and shaped to mate with or receive a mallet, distal tip of a screwdriver, or other pin driving device. Distal end 254 of pin 250 can be configured for bone penetration or anchoring in a boney structure. For example, distal end 254 may be sharp or include a barbed structure. In some variations, distal end 254 may comprise a plurality of facets, for example, two, three, four or more, and the facets may be short to facilitate stable anchoring. In other variations, the distal end 254 may comprise a different anchoring tip structure, for example, a screw tip.

Handle 240 and pin 250 can be manufactured using various techniques and formed from a range of materials. For example, handle 240 could include a radiopaque material or a radiolucent material, such as, ABS plastic. Such a material can permit viewing of the surgical site under fluoroscopy with minimal obstruction. Pin 250 may be formed from hardened stainless steel. Additionally, handle 240 and pin 250 may have any dimensions suitable for accessing and anchoring to bone. For example, handle 240 may be between about 2 cm (0.79 inches) and about 3 cm (1.18 inches) in length, and in some variations, about 2.5 cm (0.98 inches), while pin 250 may be between about 7.3 cm (2.87 inches) and about 12 cm (4.72 inches) in length or between about 8 cm (3.15 inches) and about 10 cm (3.94 inches). In some variations, pin 250 may be about 8.3 cm (3.27 inches) in length. Moreover, pin 250 may have a diameter between about 1.5 mm (0.06 inches) and about 3.2 mm (0.13 inches) or between about 2 mm (0.08 inches) and 3 mm (0.11 inches). In some variations, pin 250 may have a diameter of about 2.2 mm (0.09 inches). In other variations, one or more K-wires may be used in lieu of docking pins.

Figure 15:
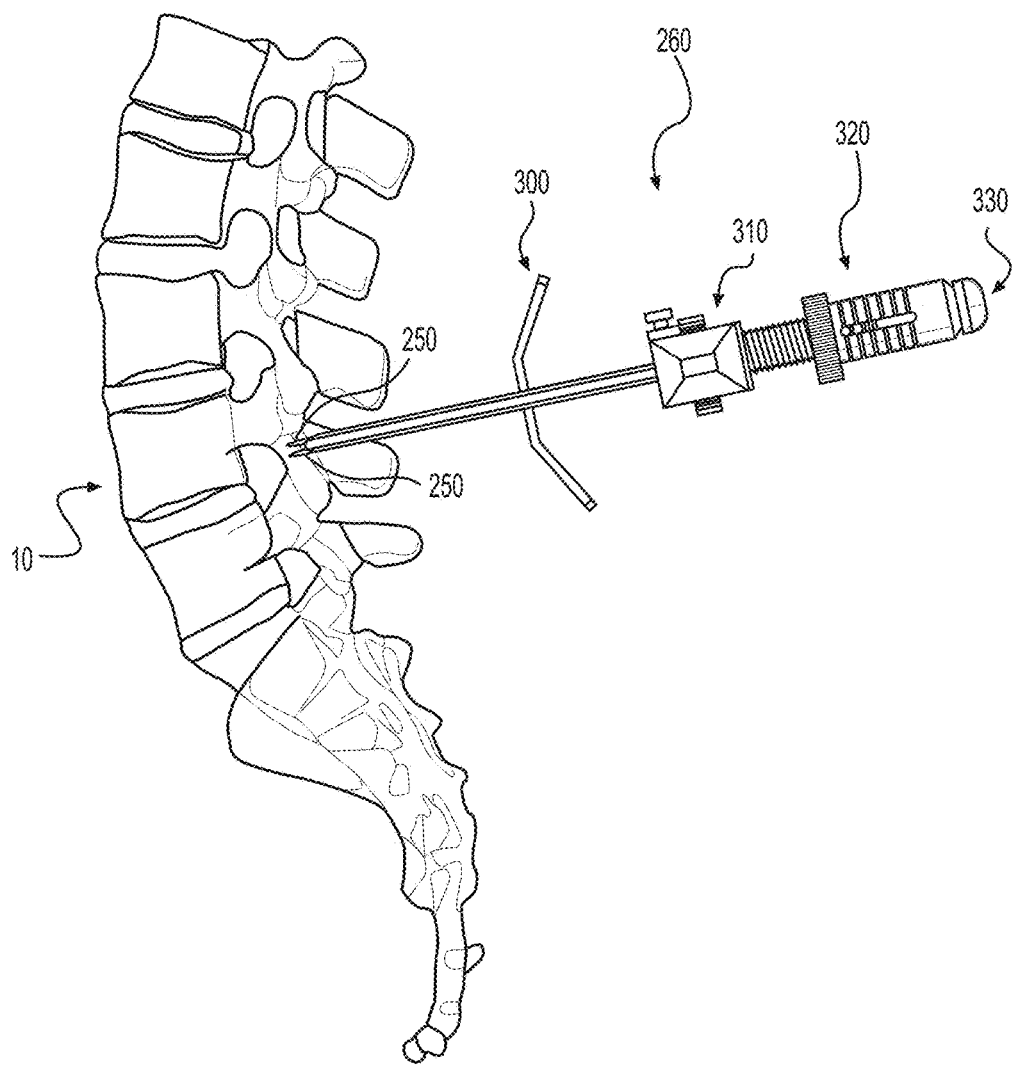
FIG. 15 shows an access portal slid over a plurality of docking pins, according to an exemplary embodiment.

In some embodiments, after pins 250 are anchored into vertebra 10, as shown in FIG. 8, access portal 260 may be slid over pins 250, as shown in FIG. 15. Access portal 260 may be slid over pins 250 until access portal 260 makes contact with vertebra 10 or lamina 16. As explained below, access portal 260 may provide controlled lateral access to vertebra 10 or lamina 16.

Pins 250 could be provided as a single device with a proximal coupling (not shown) providing lateral separation between pins 250. Pins 250 may also be coupled to lamina 16 using a template (not shown), similar to a docking pin guide 300 described below. Other devices and methods may be used to anchor a plurality of pins 250 to lamina 16.

In other embodiments, one or more pins 250 may be docketed to vertebra 10 and access portal 260 may then be slid over the one or more anchored pins 250. Following, one or more additional pins 250 may be anchored into vertebra 10 to provide additional stability and anchoring of access portal 260 to vertebra 10. For example, as shown in FIG. 6, one docking pin assembly 210 may be located in a superior region of lamina 16. Following, handle 240 may be removed from pin 250, as explained above. This can leave pin 250, as shown in FIG. 6, positioned similarly to the location of primary pin 211 in FIG. 8. Access portal 260 could be provided with one or more additional pin assemblies 210. For example, one pin 250 could be fixedly coupled to access portal 260, wherein this pin 250 could function as secondary pin 212 shown in FIG. 8. Access portal 260, containing secondary pin 212, could then be slid over primary pin 211 while it is anchored to lamina 16. Secondary pin 212 could then be anchored to lamina 16 by applying a force to access portal 260. Once secondary pin 212 is adequately anchored, access portal 260 may optionally be fixedly coupled to a proximal region of primary pin 211. Such dual anchoring could provide access portal 260 with sufficient fixation relative to lamina 16 to perform the procedures described herein.

It is also contemplated that access portal 260 may be first passed through an incision, followed by anchoring of pins 250 to vertebra 10. A dilator may also be used to provide suitable access to vertebra 10. In contrast to prior art devices using only one anchoring point, the present disclosure uses a plurality of anchoring points to provide significantly enhanced anchoring. This enhanced anchoring allows for more efficient and effective bone removal to precisely form channel 60 as desired.

Figure 9:
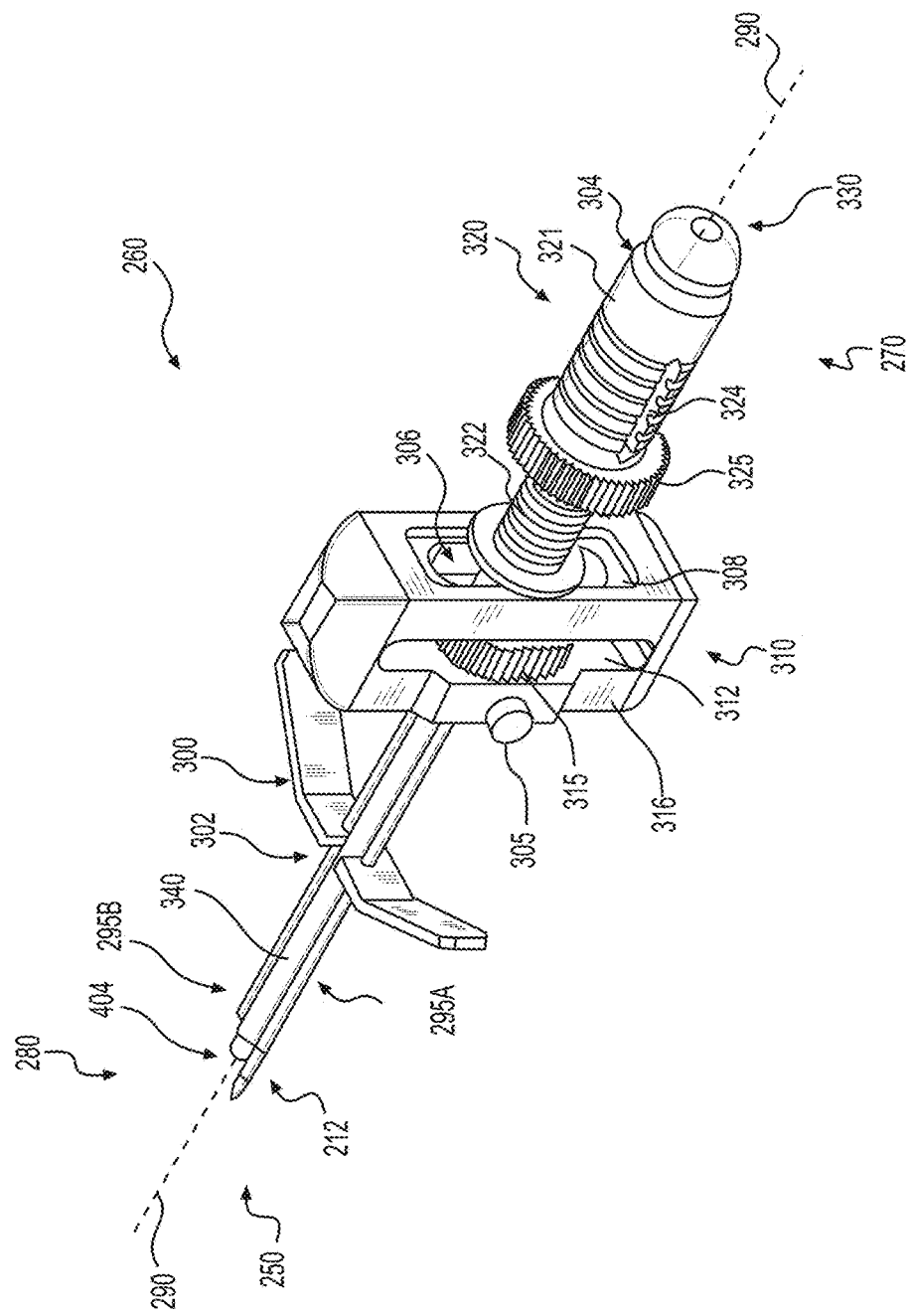
FIG. 9 shows a perspective view of an access portal, according to an exemplary embodiment.

FIG. 9 depicts access portal 260, according to an exemplary embodiment. Access portal 260 can include an elongate structure configured for use with a percutaneous procedure. Access portal 260 may be used for procedures within or adjacent to various body organs, such as, for example, vertebral column 8. Accordingly, access portal 260 can be shaped and sized for placement into a patient via a single incision.

Access portal 260 can have a proximal end 270, a distal end 280, and a longitudinal axis 290. Access portal 260 may comprise a one or more elongate members or docking pin guides configured to receive pins 250, for example, first and second elongate members 295A, 296B comprising first and second lumens therethrough respectively, and one or more elongate members configured to receive various types of surgical instruments, for example, third elongate member 340 comprising third lumen therethrough. Access portal 260 may also comprise a docking pin guide 300, a housing 310 comprising a body 316 and an actuator 315, and a depth guide adjuster 320. As shown in FIG. 9, access portal 260 may receive an obturator 330, which may be at least partially positioned within the lumen of the third elongate member 340, and secondary pin 212, which may be at least partially positioned within the lumen of one of the first or second elongate members 295A, 295B (depicted within lumen of first elongate member 295A). As mentioned above, third elongate member 340 may include an access cannula configured to receive various types of surgical instruments.

The first and second elongate members 295A, 295B (e.g., a proximal end of each) may be coupled to a distal end or surface of body 316 of housing 310 and may extend distally therefrom. In some variations, the first and second elongate members 295A, 295B may be fixedly coupled to the body 316, while in other variations, as described in more detail below, one or both of the first and second elongate members 295A, 295B may be releasably coupled to the body 316. Third elongate member 340 may be movably coupled to body 316 of housing 310 (e.g., at a proximal portion of third elongate member 340) such that the third elongate member 340 may move relative to the body 316. In some variations, the housing 310 may comprise a lock configured to temporarily limit movement of third elongate member 340 relative to body 316. In variations comprising a lock, when the lock is engaged, the third elongate member 340 may be fixed or otherwise prevented from moving relative to the housing 310, whereas when the lock is disengaged, the third elongate member 340 may slide or otherwise move relative to housing 310. Additionally, the third elongate member 340 may comprise a flattened surface 318 (FIG. 13) near a proximal end thereof (e.g., adjacent to body 316), which may allow the third elongate member 340 to be released from the docking pin guide 300, as will be described in more detail below. Flattened surface 318 may be positioned such that it is facing or adjacent the first or second elongate member 295A, 295 and an elongate edge of the second slot 309 in body 316.

Figure 13:
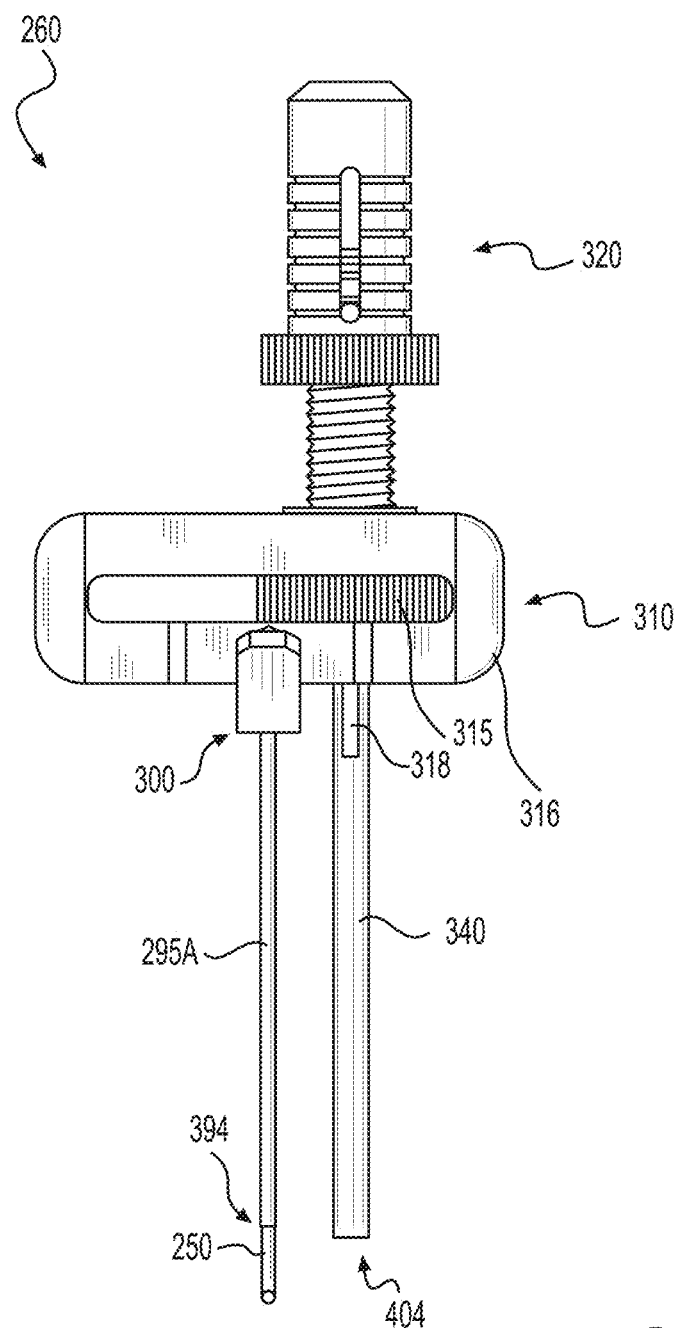
FIG. 13 shows a side view of a laterally translated access portal, according to an exemplary embodiment.

In some embodiments, pin 250 and/or first and/or second elongate member 295A, 295B may be fixedly coupled to housing 310 (e.g., body 316) and third elongate member 340 may be configured to move laterally relative to longitudinal axis 290 while pin 250, first elongate member 295A, second elongate member 295B, and/or body 316 remain essentially stationary (see FIG. 13). As explained below, such lateral movement can allow formation of slot 62 within a bone of the patient.

Pin 250 or first and/or second elongate members 295A, 295B can be releasably coupled to housing 310 (e.g., body 316) and thus to access portal 260. For example, first elongate member 295A may be fixedly attached to body 316 and pin 250 may be releasably coupled to first elongate member 295A, body 316, or both. In some variations, housing 310 may further comprise a lock or other attachment mechanism that couples either or both docking pin 250 and first elongate member 295A to body 316. For example, in some variations, housing 310 may comprise a fastener 305 that fixedly couples either or both docking pin 250 and first elongate member 295A to body 316. For example, the fastener 305 may be a locking nut, a set screw, a latch, a cam, a magnet, a ball detent, or the like. In some variations, a friction fit, adhesive, or other attachment mechanism may be used. Any of the aforementioned attachment mechanisms may be used to couple the first elongate member 295A, the second elongate member 295B, pin 250, or any additional elongate members to the housing 310 of the access portal 260, and the same attachment mechanism need not be used for each elongate member. Such mechanisms could be coupled to a surface of body 316, embedded with the body 316, or housed within the body 316.

In an exemplary embodiment, first and second elongate members 295A, 295B may be fixedly coupled to housing 310 and secondary docking pin 212 may be positioned within a lumen of first elongate member 295A and releasably coupled to housing 310 via fastener 305 before advancement to a treatment site. The access portal 260 may be then be advanced to a treatment site and second elongate member 295A may be slid or otherwise advanced over primary docking pin 211 such that primary docking pin 211 may be slidably positioned within the lumen of second elongate member 295B. In this embodiment, loosening, disengaging, or otherwise removing fastener 305 may release secondary docking pin 212 from housing 310, which may allow access portal 260 to be withdrawn or removed from the treatment site without removing docking pins 211, 212. This may allow a surgeon or user to image the area (e.g., using X-ray) without access portal 260 blocking or otherwise interfering with the image, while still allowing access portal 260 to be re-advanced to or repositioned at the same treatment location.

In some embodiments, access portal 260 may comprise only a single elongate member 295A, while in other variations and as described above, the access portal 260 may comprise a plurality of elongate members (e.g., first and second elongate members 295A, 295B, however, additional elongate members may also be included). First and second elongate members 295A, 295B can be configured to receive a plurality of pins 250, wherein a specific pin 250 may extend at least partially through one of the first and second elongate members 295A, 295B. Elongate members 295A, 295B, could be variously sized and have the same or different dimensions. For example, in some variations, the first and/or second elongate member 295A, 295B may comprise a diameter of between about 2.1 mm (0.08 inches) and about 3.8 mm (0.15 inches), between about 2.5 mm (0.10 inches) and about 3.5 mm (0.14 inches), or between about 2.7 mm (0.106 inches) and about 3 mm (0.12 inches). In some variations, the first and/or second elongate member 295A, 295B may comprise a diameter of about 2.8 mm (0.11 inches). Moreover, the first and/or second elongate member 295A, 295B may comprise a length of between about 6.9 cm (2.72 inches) and about 11.6 cm (4.57 inches), between about 7 cm (2.76 inches) and about 10 cm (3.94 inches), or between about 7.5 cm (2.95 inches) and about 8.5 cm (3.35 inches). In some variations, the first and/or second elongate member 295A, 295B may comprise a length of about 7.9 cm (3.11 inches). In other variations, the first and/or second elongate member 295A, 295B may comprise a length of between about 8 cm (3.15 inches) and about 12 cm (4.72 inches), between about 9.0 cm (3.54 inches) and about 11.0 cm (4.33 inches), or between about 9.5 cm (3.74 inches) and about 10.5 cm (4.13 inches). In some variations, the first and/or second elongate members 295A, 295B may comprise a length of about 10.414 cm (4.10 inches). While depicted as tubular elements with a circular cross-sectional shape, the elongate members 295A, 295B may have any cross-sectional shape suitable for receiving a pin 250, for example, oval, square, rectangular, triangular, hexagonal, or the like.

First and second elongate members 295A, 295B may be formed from any suitable materials. For example, in some variations, one or both of the first and second elongate members 295A, 295B may be formed from or comprise a metal alloy. In some variations, first and second elongate members 295A, 295B may be formed from the same material, while in other variations, they may be formed from different materials. Additionally, in some instances, first and second elongate members 295A, 295B may comprise more than one material, for example, one or more portions may be formed from a first material and one or more portions may be formed from a second, different material. While it is contemplated that first and second elongate members 295A, 295B may be rigid to provide stationary support for access portal 260 relative to a vertebra, first and/or second elongate member 295A, 295B may be selectively flexible to permit some controlled movement of portal 260 (e.g., body 316, third elongate member 340) relative to the vertebra. For example, in some variations, first and/or second elongate member 295A, 295B, or a portion thereof, may be formed from or comprise a flexible polymer (e.g., PC/ABS blend, ABS, or the like) or other material that allows for movement of housing 310 and/or third elongate member 340 relative to elongate members 295A, 295B when a force is applied. For example, in some variations, one or more of elongate members 295A, 295B may comprise sections along its length with different flexural properties such that a distal end of the elongate member 295A, 295B may be more flexible than a central or proximal portion of the elongate member 295A, 295B. Put another way, an elongate member 295A, 295B may be constructed (e.g., using sections formed from materials with different properties) such that flexibility of the elongate member 295A, 295B decreases from a distal end of elongate member 295A, 295B to a proximal end, which may provide flexibility to move a distal end of elongate member 340 or a tool position therein while providing enough rigidity to dock secondary pin 212 and/or maintain the general positioning of the access device 260.

First, second, and third elongate members 295A, 295A, 340 may be parallel to one another (e.g., longitudinal axes of the first, second and/or elongate members may be parallel), aligned generally along longitudinal axis 290, and distributed generally along a common lateral axis extending perpendicular to longitudinal axis 290. It should be appreciated that the third elongate member 340 may be aligned generally along longitudinal axis 290 (e.g., the longitudinal axis of the third elongate member may be co-linear with longitudinal axis 290) in a first, initial configuration (e.g., during advancement of the portal 260 and/or during the portion of a procedure leading up to slot formation) and may be moved to a second configuration (e.g., during slot formation) in which a longitudinal axis of the third elongate member 340 may be off-set or laterally shifted from longitudinal axis 290. The longitudinal axis of the third elongate member 340 may also be laterally shifted from the longitudinal axes of the first and second elongate members 295A, 295B in the second configuration. In other embodiments, elongate members 295A, 295B, 340 may be differently positioned relative to one another. For example, first and second elongate members 295A, 295B may be positioned on the same side of third elongate member 340, as opposed to on opposite sides as depicted. Further, in some variations, portal 260 may comprise more than one third elongate member 340 (e.g., two, three, four, or more).

The first and/or second elongate members 295A, 295B may also be fixedly, movably, or releasably coupled to docking pin guide 300. Such coupling may permit movement of guide 300 up or down a longitudinal axis of one or more elongate members 295A, 295B, and in some variations, may allow for removal of docking pin guide 300 from access portal 260. Relative longitudinal movement may facilitate appropriate positioning of guide 300 on a patient's skin. For example, docking pin guide 300 may be axially adjustable to account for different patient anatomy, e.g., different amounts of tissue between the target lamina and a skin surface. Additionally, docking pin guide 300 may be adjustable to allow for movement across lamina laterally or medially.

Docking pin guide 300 may include angled or contoured surfaces configured for contact with skin. For example, in some variations, docking pin guide 300 may comprise two surfaces angled inward toward a central surface. The central surface may be transverse and in some variations, generally perpendicular, to longitudinal axis 290. In other variations, docking pin guide 300 may be more curved, for example, it may be arcuate or semi-circular. The central surface may comprise first and second openings and a recess 302. The first and second elongate members 295A, 295B may be positioned through first and second openings and the third elongate member 340 may be positioned within recess 302. Recess 302 may be configured to permit movement of third elongate member 340 relative to docking pin guide 300 when docking pin guide 300 is aligned with flattened surface 318 of third elongate member 340. For example, recess 302 may have a longitudinal axis that is perpendicular to a longitudinal axis of docking pin guide 300 and may extend through a sidewall of the docking pin guide 300 such that an opening is formed for passage of the third elongate member 340 therethrough.

In use, docking pin guide 300 may be withdrawn or retracted proximally toward body 316 to align docking pin guide 300 with flattened surface 318 such that third elongate member 340 may be moved laterally. Put another way, when docking pin guide 300 is positioned between flattened surface 318 on outer surface of elongate member 340 and a distal end of elongate member 340 (e.g., along a midpoint of elongate member 340, three-fourths of the distance between body 316 and distal end of elongate member 340, one-fourth of the distance between body 316 and distal end of elongate member 340), docking pin guide 300 may hold elongate members 295A, 295B, 340 stationary (i.e., it constrains translational and/or rotational movement of elongate members 295A, 295B, 340 relative to one another and body 316) to facilitate placement of access portal 260 in the appropriate location on the vertebrae (i.e., facilitate advancement of docking pin 250 into access portal 260). When docking pin guide 300 is moved proximally into alignment with flattened surface 318, elongate member 340 may be moved laterally through the opening of recess 302 and out of the docking pin guide 300.

In some variations, first and second openings on docking pin guide 300 may comprise slots (as opposed to holes), which may allow the first and second elongate members 295A, 295B to be released from docking pin guide 300. This may allow third elongate member 340 to be moved in a first direction from its initial (central) position and in a second, opposite direction from its initial position (e.g., left-of-center and right-of-center, laterally and medially). In some variations, first and second slots in docking pin guide 300 may be offset, which may help hold first and second elongate members 295A, 295B in the docking pin guide 300. Third elongate member 340 may also assist in positioning the first and second elongate members 295A, 295B within the slots and may hold the first and second elongate members 295A, 295B within the slots when it is positioned centrally between them. After the third elongate member 340 is moved through recess 302 (as described above), the first and second elongate members 295A, 295B may be squeezed together or otherwise moved toward one another to disengage them from docking pin guide 300. Docking pin guide 300 may then be removed from access portal 260 altogether. In some variations, docking pin guide may be rotated 180 degrees and first and second elongate members 295A, 295B may be reinserted into slots in docking pin guide 300. Once rotated 180 degrees, the opening in recess 302 may face the opposite direction, and thus the third elongate member 340 may move from its initial central position, through recess 302 to extend the channel in the bone in a second, opposite direction. In some instances it may be useful to reinstall the docking pin guide 300 to further stabilize first and second elongate members 295A, 295B.

In one embodiment, with the docking pin guide 300 initially engaged, the third elongate member 340 may move medially, but not laterally, from its initial position. After the docking pin guide 300 is removed and optionally rotated and reinstalled, the third elongate member 340 may move laterally but not medially from its initial position. In variations in which the docking pin guide 300 is not reinstalled, the third elongate member 340 may freely move both laterally and medially from its initial position.

Docking pin guide 300 may be formed from a suitable medical grade material and formed to contact a patient's skin. Pin guide 300 may be curved to facilitate correct positioning of access portal 260 relative to a lamina (not shown) or other anatomical feature. Such positioning can ensure appropriate alignment of cutting tools and correct formation of channels and slots within a bone of a patient. For example, as shown in FIG. 13 and explained above, docking pin guide 300 can be configured to slide up and down elongate members 295A, 295B.

Housing 310 can be configured to permit relative movement between one or more of the first and second elongate members 295A, 295B and third elongate member 340, wherein this relative movement can be lateral and/or medial or generally perpendicular to longitudinal axis 290. As mentioned briefly above, housing 310 may comprise a body 316 and an actuator 315. Actuator 315 may be coupled to the third elongate member 340 and may be configured to move or allow movement of third elongate member 340 relative to one or more of first and second elongate members 295A, 295B and body 316. In some variations, actuator 315 may function as a lock. For example, actuator 315 may comprise first and second positions. When actuator 315 is in the first position, it may prevent relative movement between third elongate member 340 and body 316 (and first and/or second elongate member 295A, 295B). When actuator 315 is in the second position, it may allow relative movement between third elongate member 340 and body 316 (and first and/or second elongate member 295A, 295B. For example, in some variations (such as those depicted in FIGS. 9, 10A-10B, 11A-11B, and 13) actuator 315 may comprise a disk-shaped dial. The disk-shaped dial may be rotatably coupled to elongate member 340 such that when the dial is rotated in a first direction (e.g., anticlockwise), the dial moves to a first locked position and constrains the position of the third elongate member 340. When the dial is rotated in a second, opposite direction (i.e., clockwise), the dial moves to a second unlocked position in which third elongate member 340 may be moved laterally.

In some variations, actuator 315 may comprise a latch, cam, slider, or other mechanism suitable for moving or allowing movement of third elongate member 340. In other variations, third elongate member 340 may releasably couple to the housing 310 (e.g., friction fit, slot, adhesive, magnetic, or other attachment mechanism) such that the third elongate member 340 may be released from the housing 310, moved, and recoupled to the housing 310 in a different location. Housing 310 (e.g., body 316) may be formed of a metal alloy, polymer, or other material.

Turning back to the variation depicted in FIGS. 9, 10A-10B, 11A-11B, and 13, body 316 of housing 310 may comprise an internal chamber 306 and a plurality of slots that may facilitate movement of the third elongate member 340 relative to the body 316. For example, body 316 may comprise a first slot or opening 308 on a proximal surface of the body 316 (FIG. 9), a second slot or opening 309 on a distal surface of the body 316 (FIG. 16), and third a slot or opening 312 on a first side surface of the body 316 (FIG. 9). In some variations, the body 316 may comprise a fourth slot or opening on a second, opposite side surface of the body 316. The third elongate member 340 may be positioned within and through the first and second slots 308, 309 such that the third elongate member 340 extends distally through the body 316. Actuator 315 (e.g., dial) may be at least partially housed within the internal chamber 306 and may extend outward through the third slot 312 and optional fourth slot in body 316, thus allowing a user to access the actuator 315 to move and/or unlock the third elongate member 340.

The first and second slots 308, 309 may be aligned such that they form a passageway through body 316. Additionally, in variations comprising a fourth slot, the third and fourth slots 312 may be also be aligned such that they also form a passageway through body 316. The passageway formed by the third 312 and fourth slots may be generally perpendicular to the passageway formed by the first and second slots 308, 309. In some variations, the first and second slots 308, 309 may be centrally positioned on the proximal and distal surfaces of the body 316. The second slot 309 may be positioned between the first and second elongate members 295A, 295B (i.e., the first and second elongate members 295A, 295B may be coupled to body 316 on opposite sides of the second slot 309).

First and second slots 308, 309 may be configured for lateral movement, medial movement, or both lateral and medial movement of third elongate member 340. For example, each slot may have a first end and a second end and may be oriented orthogonally or at an angle to a line that intersects the first and/or second docking pin. The slots 308, 309 may be symmetrically or asymmetrically positioned with respect to the intersecting line. In some variations, for example those in which first and second slots 308, 309 may be configured for lateral or medial movement (but not both), the first end of first and second slots 308,309 may be generally centrally positioned on body 316 and/or aligned with longitudinal axis 290 and the first and second slots 308, 309 may extend in one direction (e.g., medially or laterally, right or left). In other variations, for example those in which first and second slots may be configured for both lateral and medial movement, a midpoint of first and second slots 308, 309 may be aligned with longitudinal axis 290 such that the first and second slots 308, 309 may extend from the midpoint in two directions (e.g., medially and laterally, right and left) between first and second ends, which are positioned on either side of longitudinal axis 290. It should be appreciated that in some variations, slots 308, 309 may be offset (shifted) relative to longitudinal axis 290 such that a different point along the length of first and second slots 308, 309 may be aligned with longitudinal axis 290. In some of these variations, lateral and medial travel paths may not be equal lengths.

Moreover, in some instances, the first and second slots 308, 309 may have the same cross-sectional shape (e.g., rectangular, oval, or the like) and dimensions (e.g., length and width), while in other variations, the first and second slots 308, 309 may have different cross-sectional shapes and/or dimensions (e.g., the second slot 309 may be wider, which may allow for additional movement at the distal end of the third elongate member 340).

Figure 16:
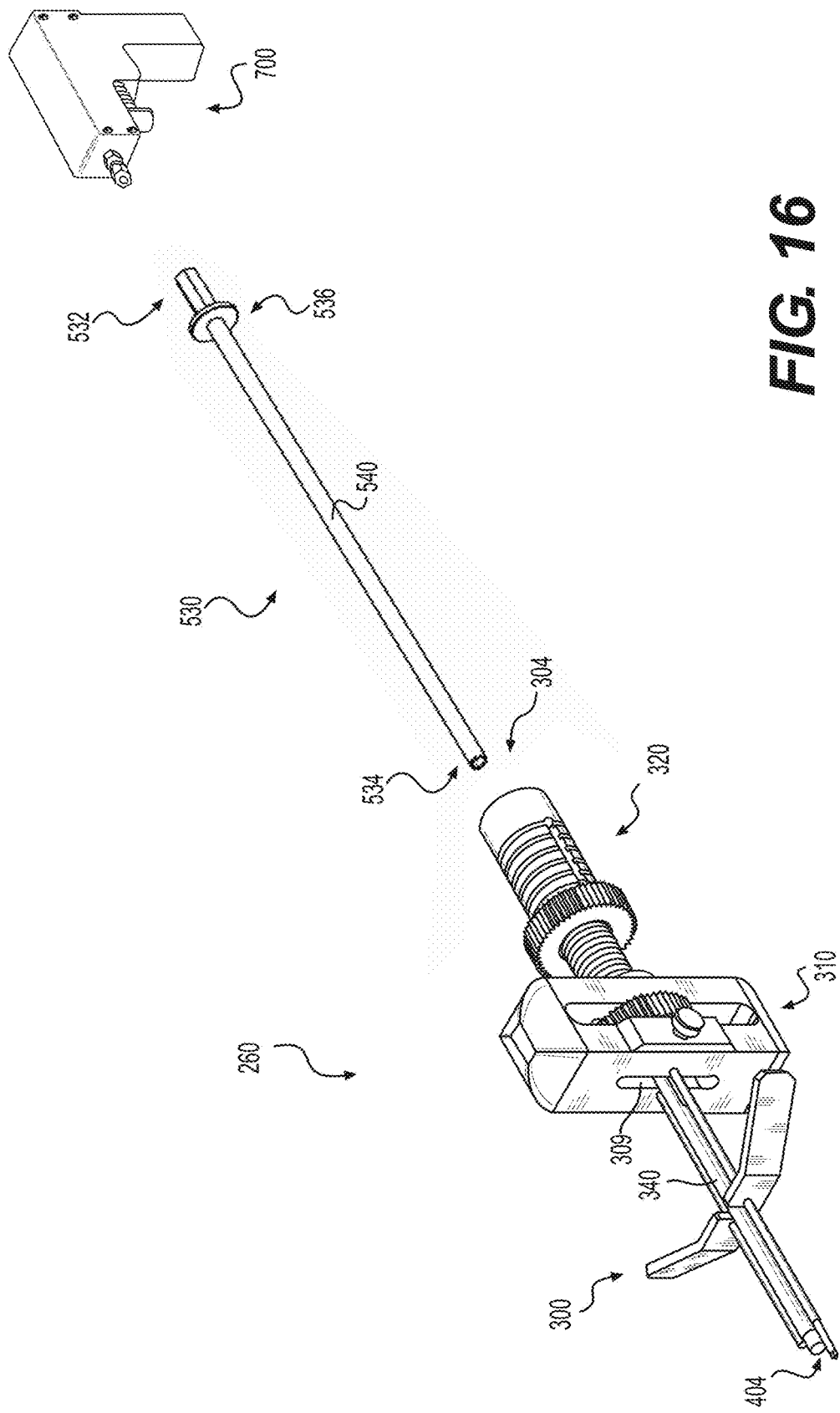
FIG. 16 shows an access portal detached from a trephine and a power source, according to an exemplary embodiment.

As mentioned above, in some variations, the first and second slots 308, 309 may be configured (e.g., dimensioned and positioned) to allow the third elongate member 340 to move medially or laterally, but not both medially and laterally. In these variations, the first and second slots 308, 309 may have a shorter length than in variations in which the third elongate member 340 may move both medially and laterally (body 310 depicted in FIGS. 9 and 16 is configured for both medial and lateral movement). In variations in which first and second slots 308, 309 are configured to accommodate movement of third elongate member 340 in a single direction, first and/or second slot 308, 309 may have a length between about 1.3 cm (0.51 inches) and about 2.0 cm (0.79 inches), between about 1.5 cm (0.59 inches) and about 1.8 cm (0.71 inches), or about 1.6 cm (0.63 inches). In variations in which first and second slots 308, 309 are configured to accommodate movement of third elongate member 340 in two directions (e.g., medially and laterally), first and/or second slot may have a length between about 2.6 cm (1.02 inches) and about 4.0 cm (1.57 inches) or between about 3.0 cm (1.81 inches) and about 3.5 cm (1.38 inches). In some variations, the first and/or second slot 308, 309 may have a length of about 3.2 cm (1.26 inches).

In some instances, the width of the first and/or second slot may be about equal to or just slightly larger than the diameter of the third elongate member 340. For example, the width may be between about 5 mm (0.197 inches) and about 6 mm (0.236 inches) or between about 5.2 mm (0.205 inches) and about 5.5 mm (0.217 inches). In some embodiments, the width of the first and/or second slot may be about 5.4 mm (0.213 inches).

The third 312 and fourth slots may also have the same cross-sectional shape (e.g., rectangular) and dimensions, and may have the same or different cross-sectional shapes and dimensions as the first and second slots 308, 309. For example, in some instances, the third 312 and/or fourth slot may have the same length as the first and/or second slots 308, 309, while in other variations, the third 312 and/or fourth slot may be longer or shorter than the first and/or second slots 308, 309. Similarly, in some variations, the third 312 and/or fourth slot may have a larger or smaller width than the first and/or second slots 308, 309. For example, as depicted in FIG. 9, the third slot 312 may have a longer length and a shorter width than the first slot 308. Moreover, while the third slot 312 may have a rectangular or oval cross-sectional shape to accommodate the disk-shaped dial, this need not be in the case. In some variations, for example, in variations in which additional degrees of freedom for the third elongate member 340 are desired, the third slot 312 (and optional fourth slot) may have a circular cross-sectional shape, which may accommodate a spherical or ball shaped actuator.

As mentioned above, third elongate member 340 may be positioned through the first and second slots 308, 309 and the actuator 315 may extend from within the body 316 through the third slot 312. Thus, first and second slots 308, 309 may act as guides or tracks for the third elongate member 340, while third slot 312 (and fourth slot) may act as a guide or track for actuator 315. Put another way, first and second slots 308, 309 and third slot 312 may allow for movement of the third elongate member 340 and actuator 315 (e.g., dial) respectively in along one axis (e.g., along a longitudinal axis of the slot, perpendicular to longitudinal axis 290), while constraining movement of elongate member 340 and actuator 315 respectively along other axes. Movement of actuator 315 (e.g., rotational, translational) within third slot 315 moves and/or allows movement of third elongate member 340 within first and second slots 308, 309, thus allowing formation of a slot in bone, as will be described in more detail below. Free-form movement is also contemplated whereby a surgeon may move third elongate member 340 relative to housing 310 freely in one or more lateral directions.

Additionally, access portal 260 (e.g., housing 310, actuator 315) may further include one or more stops, movement assist, dampening, or other movement related mechanism. In some instances, a user may encounter resistance when moving or sliding third elongate member 340 laterally from, for example, muscle or other anatomical structures of the patient. Thus, in some variations, it may be useful to include additional elements to assist a user with this lateral movement. Thus, in some embodiments, housing 310 may further comprise a rack and pinion coupled to third elongate member 340, which may provide a user leverage in moving third elongate member 340. The rack and pinion may additionally include a friction or lock screw. In other variations, housing 310 may further comprise wire or cable coupled to third elongate member 340 and rolled around a drum. The wire or cable may be used to pull third elongate member 340 laterally. In other instances, housing 310 may comprise a ratchet and pawl or a cam that may assist in moving the third elongate member 340. Additionally or alternatively, the housing 310 (e.g., slots 308 and/or 309) may also comprise ball detents such that when third elongate member 340 is moved laterally, it may stop in the ball detent locations. The ball detent locations may correspond to desired drilling locations and thus may assist a user in identifying when third elongate member 340 reaches the next drilling location. This may increase repeatability of the procedure, for example, by demarcating the various positions of the third elongate member 340 and may enable a user to move the third elongate member 340 to the same location more easily.

Depth guide adjuster 320 may be configured to control the relative depth of one or more elongate members or devices positioned within lumens of one or more elongate members of access portal 260 and may be configured to transfer rotational movement into linear movement along longitudinal axis 290. In one embodiment, guide adjuster 320 may comprise a handle or outer housing 321, a central member 322, a pin 323, and an adjusting dial 325. In some variations, outer housing 321 may comprise an elongate tubular member with a lumen 326 therethrough, a proximal end 304, and a longitudinal through wall slot 324 connecting lumen 326 to an outer surface of outer housing 321. Central member 322 may comprise a threaded rod comprising a lumen therethrough (depicted in FIG. 10B with a tool within the lumen). Outer housing 321 may be operably coupled to adjusting dial 325 (e.g., it may abut or otherwise rest on a proximal surface of adjusting dial 325), which may be rotatably coupled to central member 322. Central member 322 may be positioned within lumen 323 of outer housing and may advance or retract within lumen 323 as adjusting dial 325 is rotated. Pin 323 may be fixedly coupled to central member 322 and may be slidably positioned within longitudinal slot 324, which may both couple outer housing 321 and central member 322 and provide an indication of the depth of a tool positioned within lumen 326 and lumen of central member 322.

Outer housing 321 of guide adjuster 320 may comprise markings, indicia, or other indicators of absolute or relative depth. In some embodiments, guide adjuster 320 can be configured to adjust the height of an instrument in increments, such as, for example, 0.5, 1, 2, or 4 mm. Manipulating guide adjuster 320 can permit a surgeon to precisely control the depth of one or more components within a patient. Precise depth control can be critical to ensure that a nerve is not inadvertently severed. As shown in FIG. 9, a proximal end 304 of guide adjuster 320 can be configured to engage a handle or distal facing surface of obturator 330. It is also contemplated that proximal end 304 could be configured to engage other types of surgical instrument. In some embodiments, access portal 260 could operate without the use of guide adjuster 320.

One or more components of access portal 260 can be formed from a suitable medical grade material. Further, one or more parts of access portal 260 may include a metal alloy or material with similar properties. For example, in some embodiments, one or more elongate members 295A, 295B, 340 can be at least partially formed using a metal alloy, such as stainless steel. In other embodiments, first and second elongate members 295A, 295B can be made of a material having additional rigidity or other features providing additional strength. For example, in some variations, first and/or second elongate members 295A, 295B may be formed from or comprise PC/ABS plastic and/or comprise stainless steel portions or structures. These or other components of portal 260 can be formed of or comprise a radiopaque or radiolucent material, such as ABS plastic, to provide markers for guidance during a procedure.

Figure 10A:
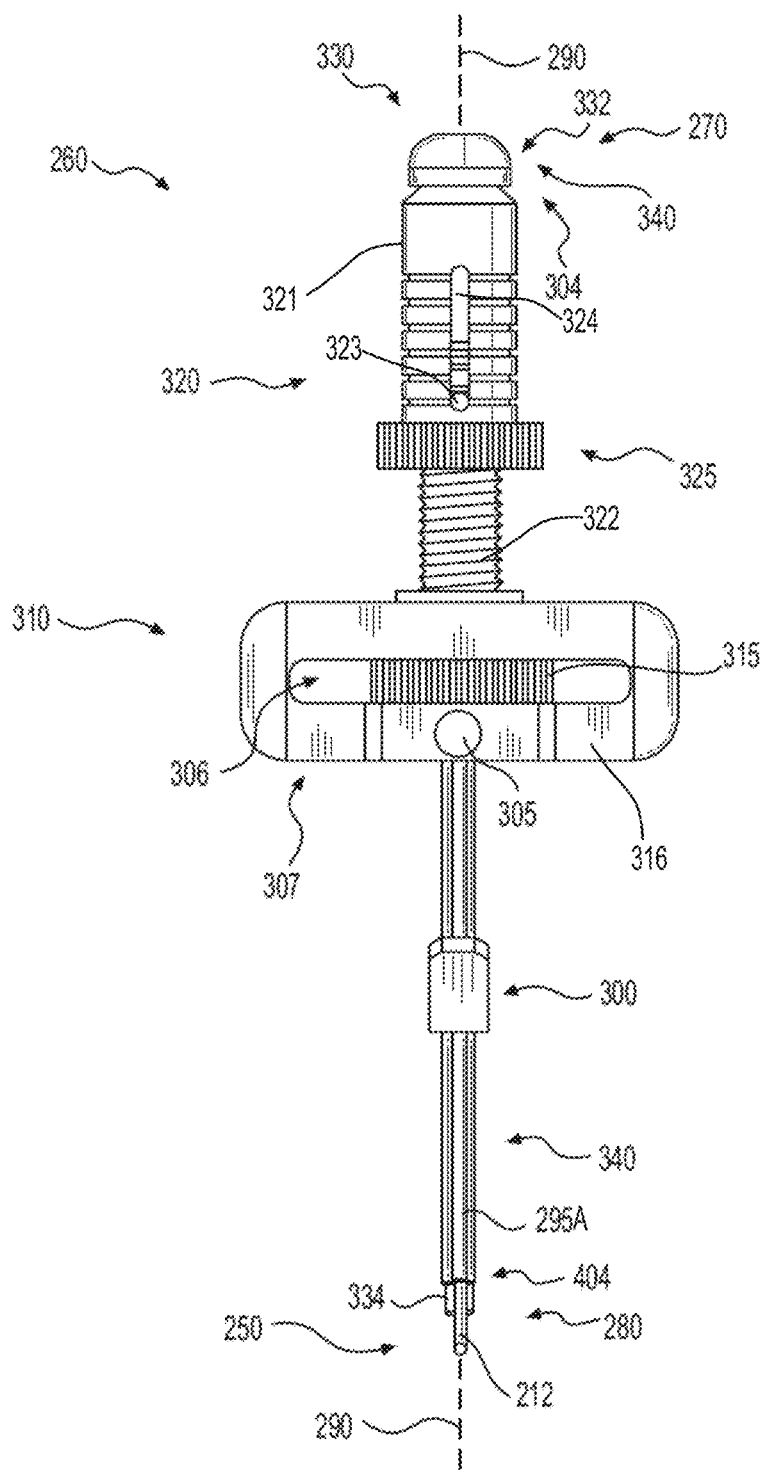
FIGS. 10A and 10B show side and cut-away side views, respectively, of an access portal, according to an exemplary embodiment.

FIGS. 10A-12B illustrate different views of access portal 260, according to an exemplary embodiment. FIG. 10A illustrates a side view of portal 260 wherein one pin 250 is positioned directly behind another pin (not shown) and third elongate member 340 is configured to move left or right relative to housing 310. As shown in FIG. 10B, illustrating a cut away view of portal 260, third elongate member 340 can translate left and right within first slot 308 and internal chamber 306. Accordingly, the entire third elongate member 340 (both proximal and distal ends) can move left as indicated by an arrow 342 or right as indicated by an arrow 344. Guide adjuster 320 and a medical instrument (obturator 330 in FIGS. 10A-11B) can also be translated in one or more vertical directions relative to housing 310, such that longitudinal axes of the third elongate member 340 and the medical instrument are translated to a position parallel to, but shifted from, their initial positions. This translation can occur while body 316 remains fixedly anchored relative to a patient.

Figure 11A:
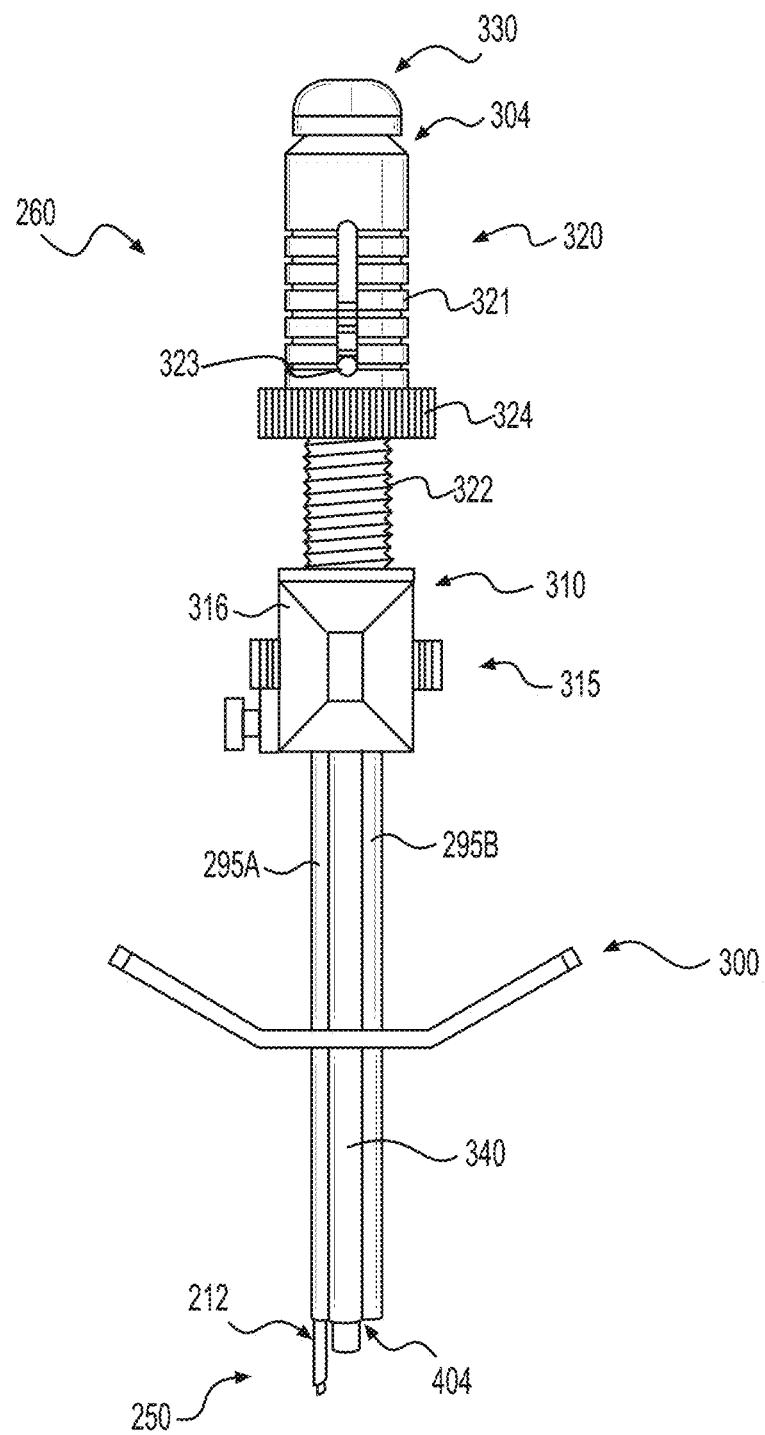
FIGS. 11A and 11B show side and cut-away side views, respectively, of an access portal, according to an exemplary embodiment.

FIG. 11A illustrates another side view of access portal 260, according to an exemplary embodiment. Docking pin guide 300 can be fixedly or movably coupled to one or more elongate members 295A, 295B, 340. In some embodiments, pin guide 300 may not be required or other devices could be configured to perform one or more functions of pin guide 300.

Figure 10B:
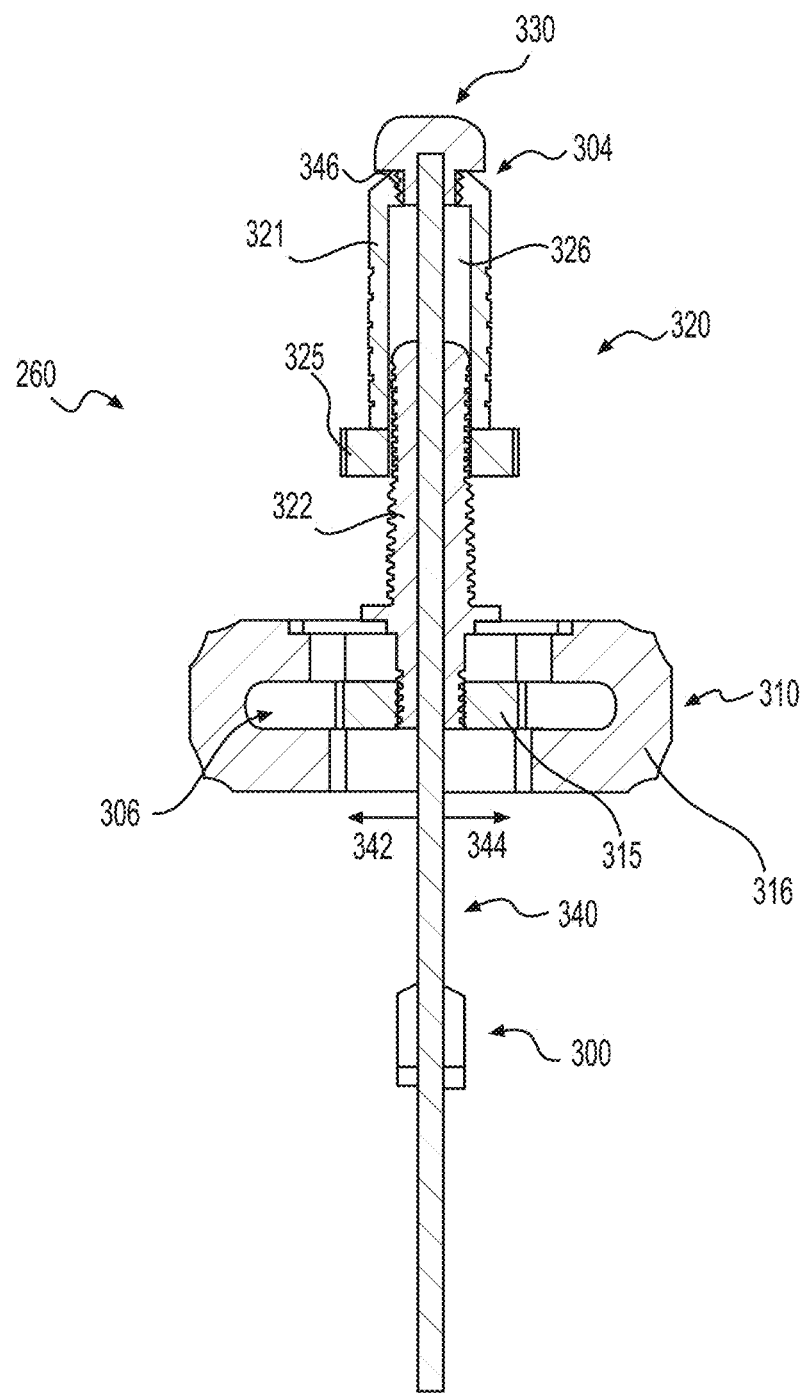
Figure 11B:
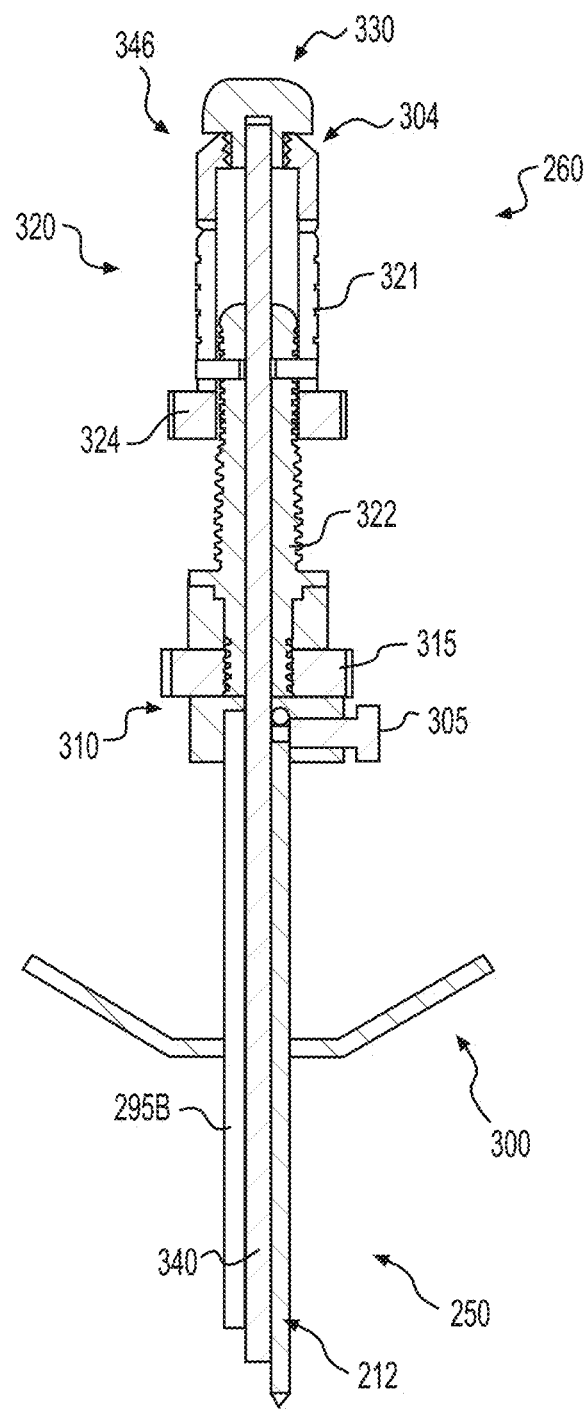
Figure 12A:
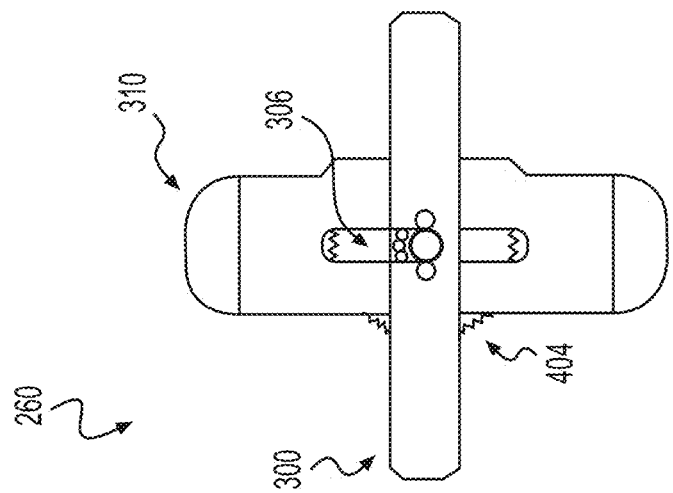
FIGS. 12A and 12B show above and below views, respectively, of an access portal, according to an exemplary embodiment.
Figure 12B:
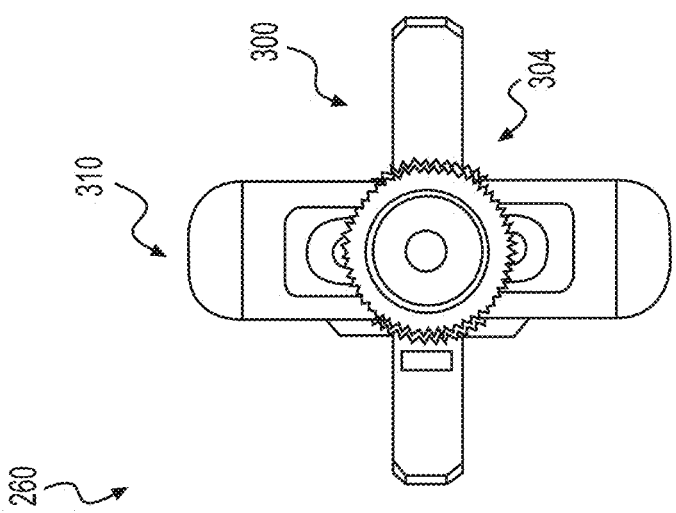

FIGS. 10B and 11B depict cut-away side views of access portal 260, according to an exemplary embodiment. In particular, access portal 260 can be configured to adjust the height of a medical instrument located within third elongate member 340 relative to first and second elongate members 295A, 295B, housing 310, or guide adjuster 320. For example, proximal end 304 of guide adjuster 320 can be moved proximally or distally relative to the patient to vary the height of an instrument and to raise or lower a position of the instrument relative to portal 260. Such height adjustment can increase or decrease the extent to which an instrument extends into the patient's body.

Guide adjuster 320 may be configured to move relative to one or more parts of portal 260. As explained below, guide adjuster 320 can be used to limit the movement of one or more instruments relative to vertebra 10. For example, guide adjuster 320 could be used to limit ventral or distal movement of trephine 530, feeler probe 555, rongeur 560, or other device associated with portal 260. Guide adjuster 320 could be adjusted before or while an instrument is being used. Limiting instrument movement can serve to protect tissue, such as, for example, spinal cord 28, from accidental contact.

As mentioned above, guide adjuster 320 may comprise adjusting dial 325. Adjusting dial 325 may be rotatably coupled, e.g., using threads, to central member 322. Rotational movement of adjusting dial 325 relative to central member 322 may raise or lower outer housing 321 relative to housing 310 and third elongate member 340. Thus, rotational movement of adjusting dial 325 (e.g., clockwise, anticlockwise) may raise or lower an instrument operably coupled to or with proximal end 304 of outer housing 321 relative to housing 310 and distal end of third elongate member 340. Other configurations are also contemplated. For example, central member 322 may move relative to housing 310 to adjust a relative height of outer housing 321.

Components of portal 260 can also include one or more threads, or other connectors, to couple various components together. For example, obturator 330 is shown engaged with guide adjuster 320 via a threaded couple 346. Dials 315, 325 are shown engaged with central member 322 of guide adjuster 320 using threads. Dial 315 may be rotated to lock or unlock third elongate member 340 relative to body 316. Dial 325 may be rotated to move obturator 330, or another type of instrument located within third elongate member 340, up or down relative to housing 310. For example, dial 325 may be rotated clockwise to raise outer housing 321 relative to housing 310 and distal end of third elongate member 340 and/or rotated anticlockwise to lower outer housing 321 relative to housing 310 and distal end of third elongate member 340.

While FIGS. 10B and 11B show various threads movably or fixedly coupling components, various other types of connections between one or more components of access portal 260 are contemplated. Other types of connectors could include a button, a lever, a cam, a rack and a pawl, a tab, a snap-connect, or a thumb-wheel and a gear. Various components could also be connected using a luer lock, a collet, a ball and socket, a ¼ turn fastener, or a magnetic element. Access portal 260 can be configured to receive one or more surgical instruments, such as, for example, obturator 330. Obturator 330 can be configured to aid insertion of access portal 260 into a patient. Obturator 330 can at least partially reside within guide adjuster 320, housing 310, and/or third elongate member 340.

Figure 14:
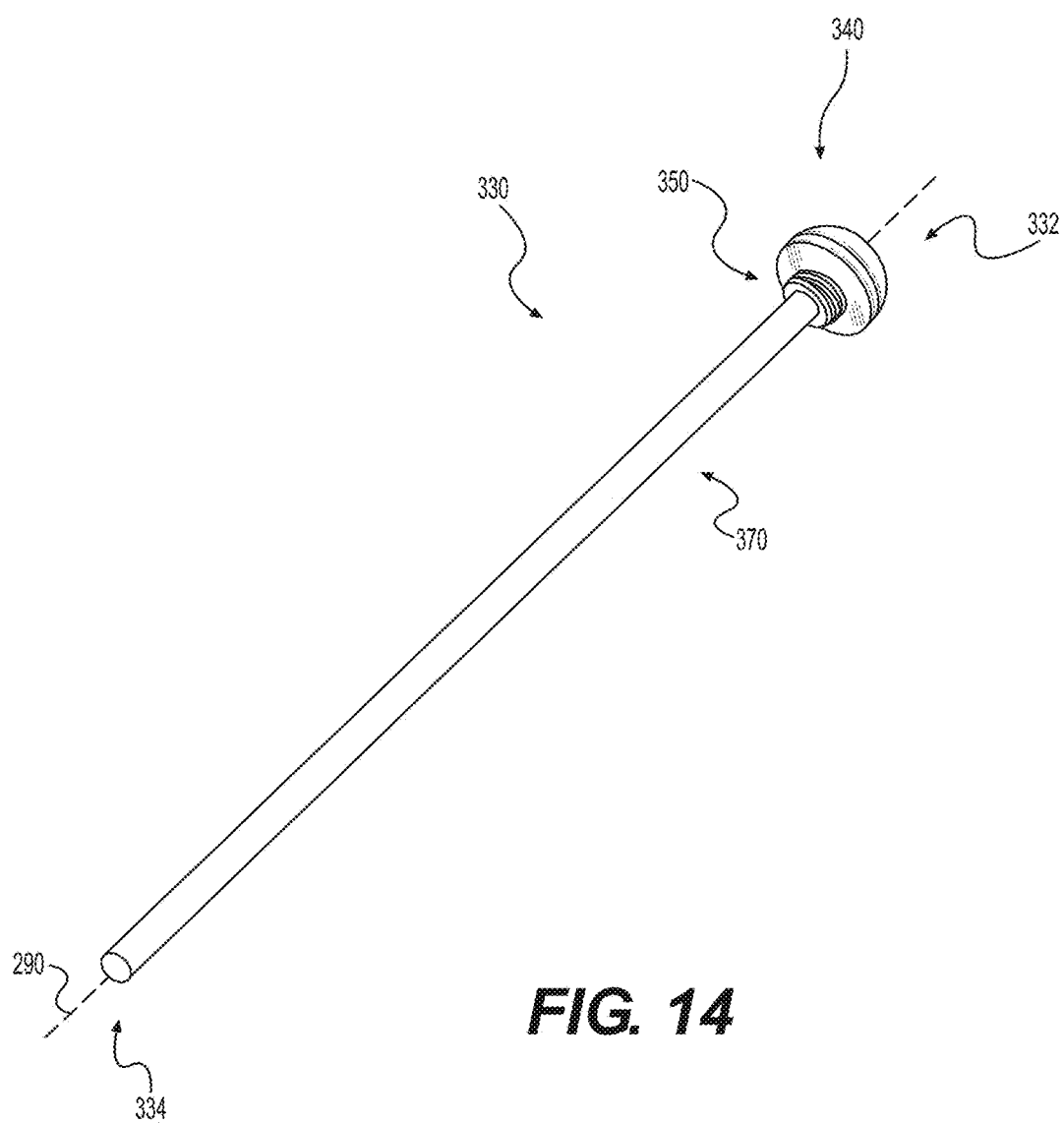
FIG. 14 shows a stylet, according to an exemplary embodiment.

As shown in FIG. 14, obturator 330 can include a proximal end 332 and a distal end 334. In some embodiments, proximal end 332 can include a handle 350 configured to aid removal of obturator 330 from portal 260. Proximal end 332 could also be configured to limit distal movement of obturator 330 relative to guide adjuster 320 or portal 260. Distal end 334 can include a blunt tip configured to part soft tissue and not penetrate bone. Distal end 334 may extend beyond distal end 280 of portal 260. Obturator 330 can also be configured to attach to or detach from guide adjuster 320 or portal 260. Obturator 330 can include a stylet shaft 370 having distal end 334. Distal end 334 can be cone shaped to provide dilation of soft tissue as access portal 260 is slid over one or more pins 250. It is also contemplated that distal end 334 could include a sharp tip configured to pierce or cut tissue.

As explained above, third elongate member 340 can be configured to receive at least part of obturator 330. For example, the lumen of third elongate member 340 may be shaped and sized to receive distal end 334 of obturator 330. Also, the lumen of third elongate member 340 may be configured to receive at least part of a surgical instrument. In some embodiments, third elongate member 340 can be centered on longitudinal axis 290. Third elongate member 340 can include a proximal end 402 and a distal end 404.

In some embodiments, elongate members 295A, 295B can be configured to move relative to third elongate member 340. For example, distal end 394 of first and/or second elongate members 295A, 295B can be configured to move laterally relative to distal end 404 of third elongate member 340 (see FIG. 13). One or more of first, second, and third elongate members 295A, 295B, 340 can remain generally parallel relative to each other and move laterally relative to each other. In other embodiments, one or more elongate members 295A, 295B, 340 could be flexible or their respective attachment to housing 310 could be flexible to permit some selective lateral movement of their distal ends 394, 404. As explained below, lateral movement between distal ends 394, 404 can permit formation of an appropriately sized slot 62 within lamina 16.

As shown in FIG. 15, access portal 260 may be slid over one or more pins 250. During insertion, obturator 330 may be located within third elongate member 340 such that distal end 334 of obturator 330 at least partially extends beyond distal end 404 of third elongate member 340. Distal end 334 may assist dilation of tissue during access to a surgical site or may cut tissue to assist locating distal end 404 at the surgical site.

Once positioned adjacent to lamina 16, one or more pins 250 associated with access portal 260 may be anchored to lamina 16. For example, secondary pin 212 may be anchored to lamina 16 by tapping on obturator 330. In another example, both primary pin 211 and secondary pin 212 can be anchored to lamina 16 using access portal 260. Other possible sequences for anchoring a plurality of pins 250 are also contemplated.

Following appropriate positioning of distal end 404 at the surgical site, obturator 330 can be removed from access portal 260 and third elongate member 340. Appropriate positioning can occur when obturator 330 makes contact with lamina 16. Once obturator 330 is removed, portal 260 may be moved slightly, in an anterior direction, to ensure that distal end 404 resides above lamina 16.

Following anchoring, trephine 530 may be inserted through access portal 260 (e.g., third elongate member 340), as shown in FIG. 16. As also shown, guide adjuster 320 can be moved proximally and distally relative to housing 310. As explained below, such height adjustment can at least partially limit distal movement of trephine 530 relative to access portal 260.

Trephine 530 can include an elongate member 540 comprising distal end 534 and a lumen therethrough, and a proximal end 532. Proximal end 532 can be configured to engage access portal 260 to at least partially limit distal movement of trephine 530 relative to access portal 260. For example, proximal end 532 could include a hub 536 configured to engage guide adjuster 320 (e.g., outer housing 321). In some embodiments, hub 536 may comprise a cylindrical distal end (e.g., a washer) and a hexagonal proximal end, which may be integrally formed or formed separately and coupled to one another using, for example, laser welding, soldering, a press-fit connection, or the like. In some variations, hub 536 may comprise a shank (e.g., with a beveled edge) or a quick release connector (e.g., a trinkle or AO connector).

The cylindrical distal end may couple or otherwise rest on a proximal surface of outer housing 321 of guide adjuster 320 and the proximal end may couple to or engage a power source 700 (e.g., a surgical drill powered by an electric motor, or a pneumatic drive) or similar device configured to rotate trephine 530. In some variations, hub 536 may be rotated by hand. Trephine 530 may be cordless and powered by a battery.

Distal end 534 of trephine 530 can be configured to cut bone. For example, distal end 534 can include unidirectional teeth to rotatably cut bone during clockwise or anticlockwise rotation. Distal end 534 can also include an undercut helical spiral (not shown) to retain bone fragments during cutting of the bone. The helical spiral may be contained on an elongate member 540 extending generally from distal end 534 to proximal end 532. Trephine 530 may also be coated with a coating to aid removal, such as, for example, a lubricous coating. In some variations, elongate member 540 may be coated with a lubricous coating (e.g., on an inner and/or outer diameter thereof), which may reduce friction between bone within elongate member 540 and/or between the outer surface of elongate member 540 and surrounding bone. Additionally or alternatively, in some variations, a cooling fluid (e.g., saline) may be applied to trephine 530 (e.g., within or to elongate member 540), which may dissipate heat generated and may cool the device. Trephine 530 may also be tapered or have a reduced diameter within a region of distal end 534 to reduce friction with surrounding tissue. One or more other features may be included on a distal region of trephine 530 to aid removal from lamina 16.

In some embodiments, trephine 530 can be placed within a lumen of third elongate member 340 of access portal 260 such that distal end 534 of trephine 530 extends beyond distal end 404 of third elongate member 340. The distance between distal ends 534 and 404 can be controlled to provide appropriate spacing between distal end 534 of trephine 530 and distal end 404. Such relative depth control can ensure that trephine 530 does not extend too far into vertebra 10.

In some embodiments, guide adjuster 320 can be used to control the relative spacing of distal ends 534 or 404. For example, as mentioned above, moving guide adjuster 320 proximally or distally can move outer housing 321 proximally or distally, which may in turn move hub 536 and elongate member 540 proximally or distally. Thus, guide adjuster 320 can be used to limit the longitudinal movement of trephine 530 relative to housing 310.

In particular, dial 325 may be used to adjust the relative height of guide adjuster 320. A distance between distal end 534 of trephine 530 and guide adjuster 320 can be adjusted so that when hub 536 makes contact with guide adjuster 320, distal end 534 may make contact with vertebra 10. Dial 325 can then be used to move guide adjuster 320 distally by a known distance. Thus, guide adjuster 320 can prevent unwanted distal displacement of trephine 530 beyond the known distance. Movement of trephine 530 beyond the known distance could damage spinal cord 28 or other tissue located beyond an anterior surface of vertebra 10.

Other devices could also be used to limit the movement of trephine 530 relative to access portal 260. For example, one or more wedges or blocks could be added to access portal 260 to provide an adjustable limit to distal movement of trephine 530. Levers or cams of variable height may be used to limit movement of trephine 530.

Under a lateral fluoroscopic view, a channel of suitable depth may be bored into lamina 16. Guide adjuster 320 may be adjusted so that distal end 534 of trephine 530 is located at the same position as distal end 404 of third elongate member 340. Then, guide adjuster 320 may be incrementally moved ventrally or distally to incrementally deepen a channel within lamina 16. Such controlled ventral or distal movement of trephine 530 can provide precise control over channel depth to ensure that tissue located within vertebral foramen 15 is not inadvertently damaged.

Figure 3A:
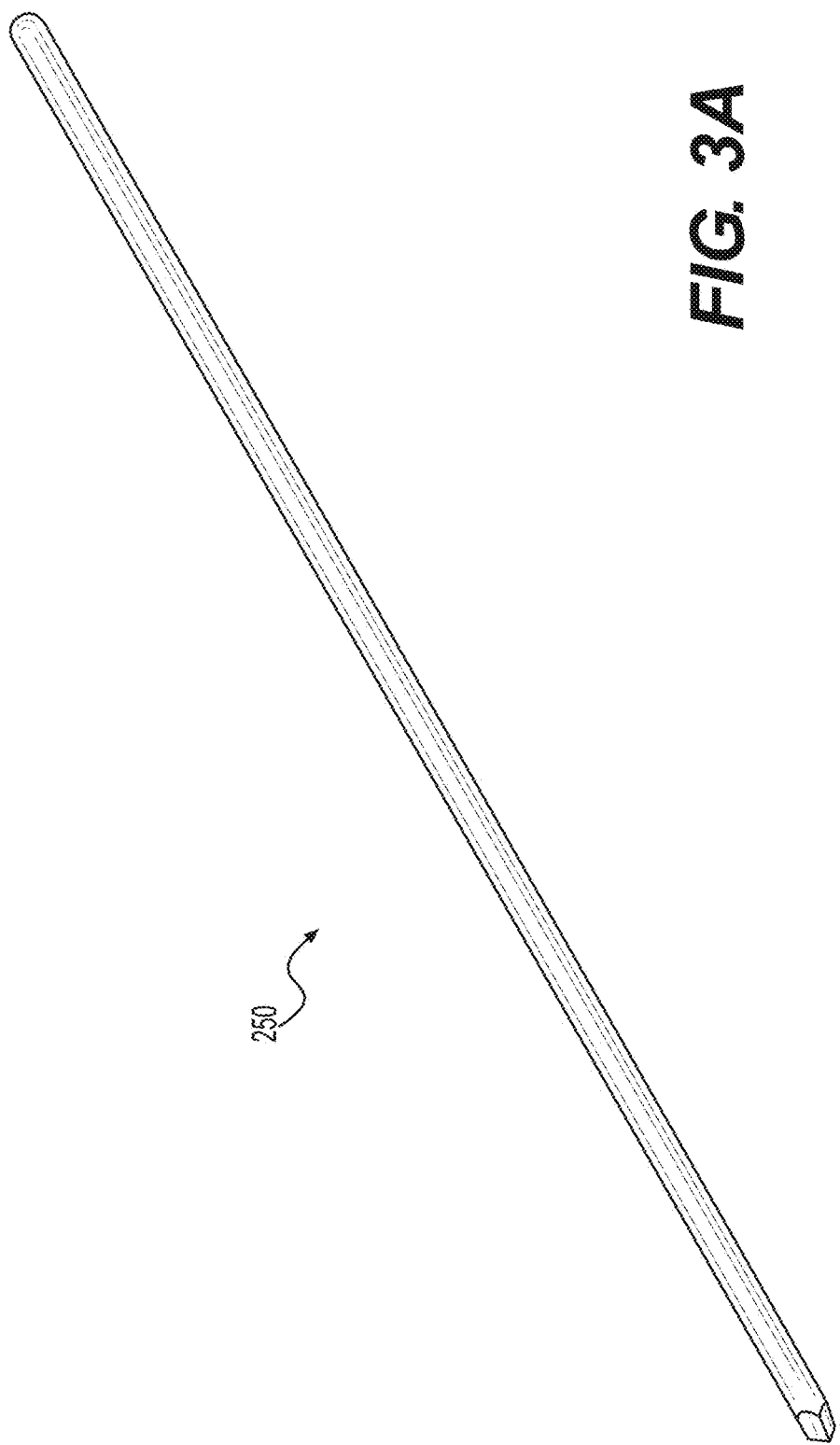
Figure 3C:
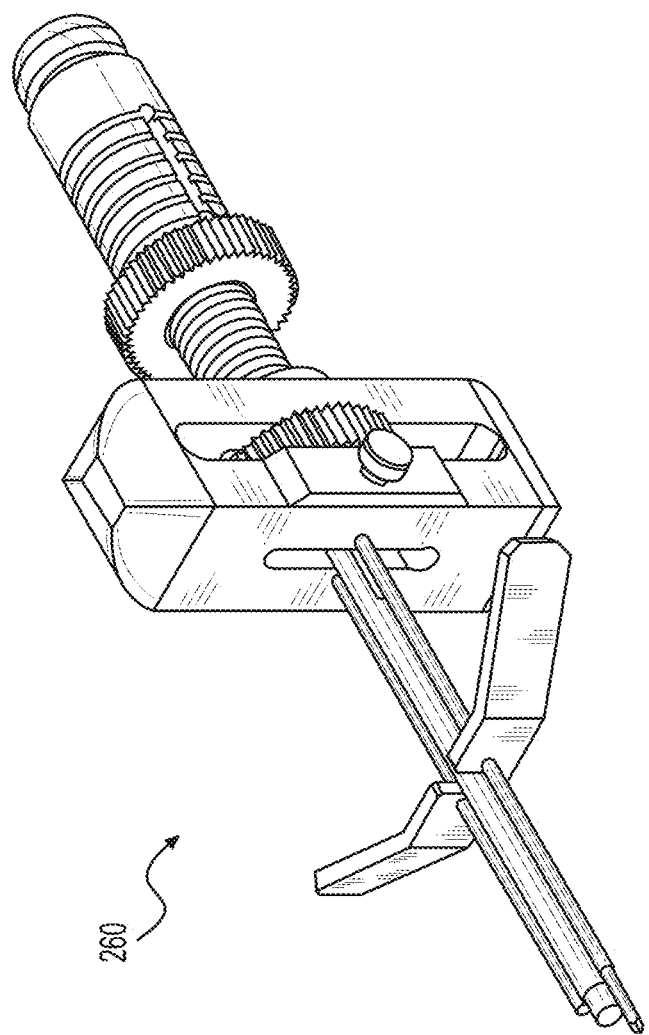
Figure 3D:
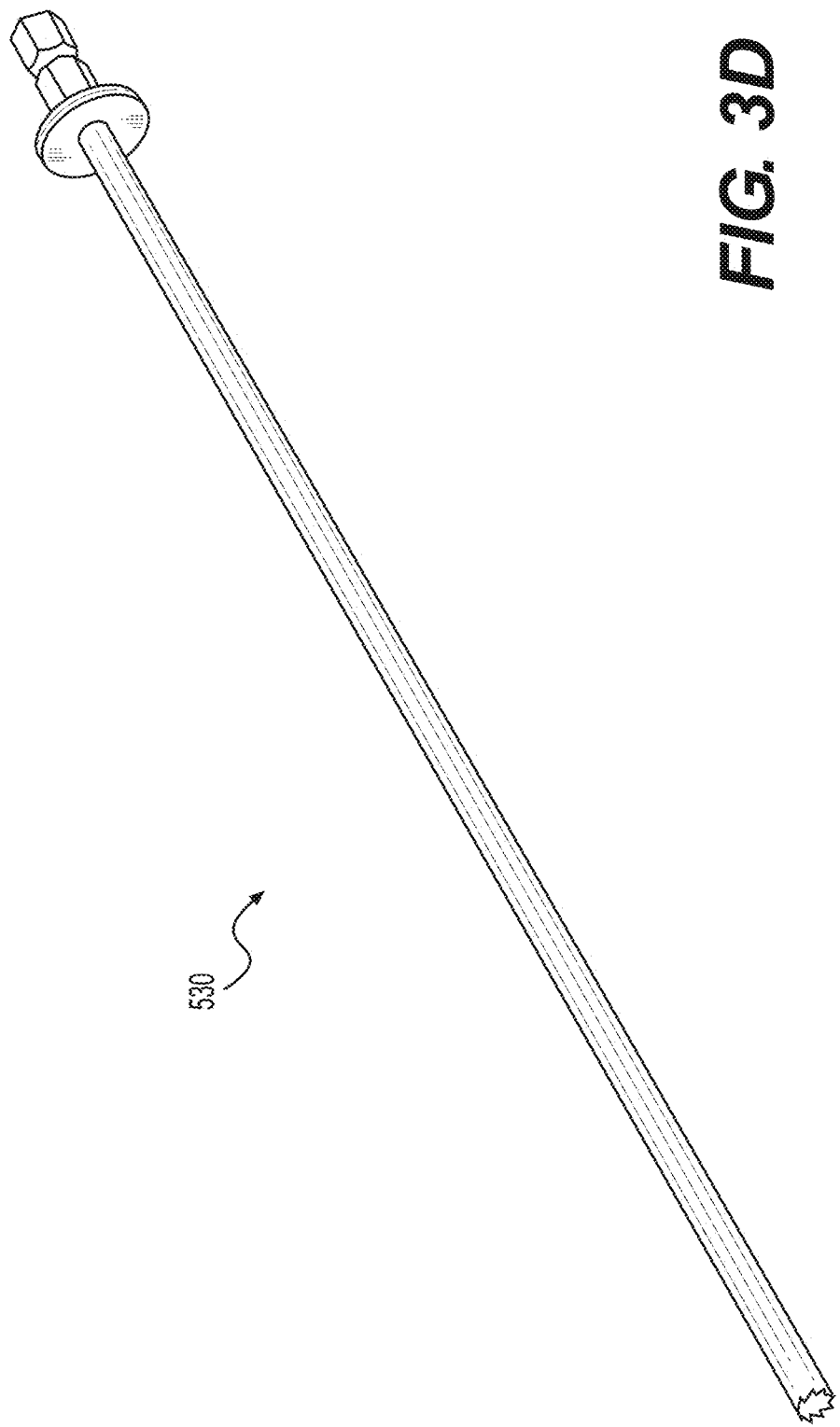
Figure 3E:
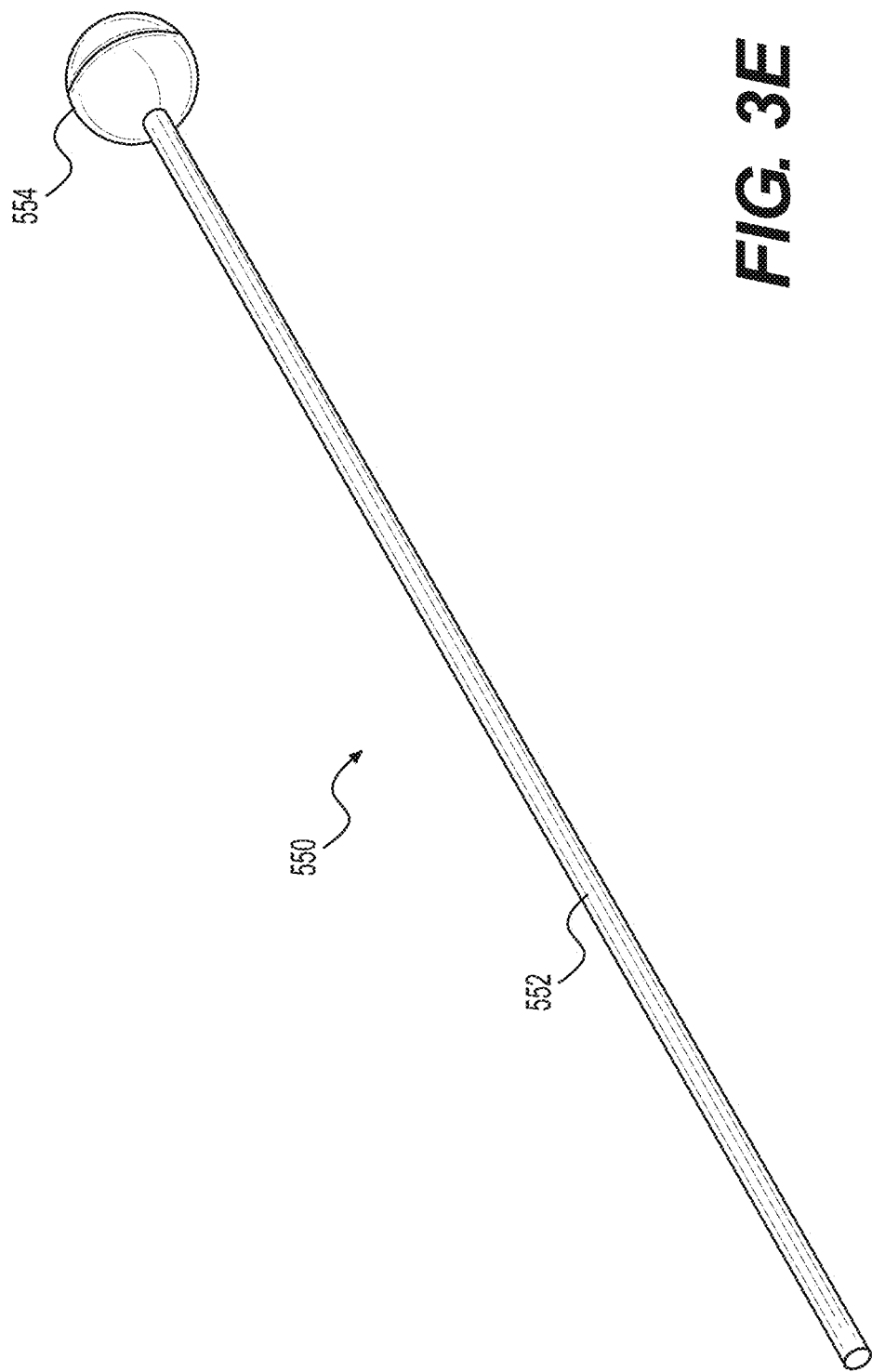
Figure 3F:
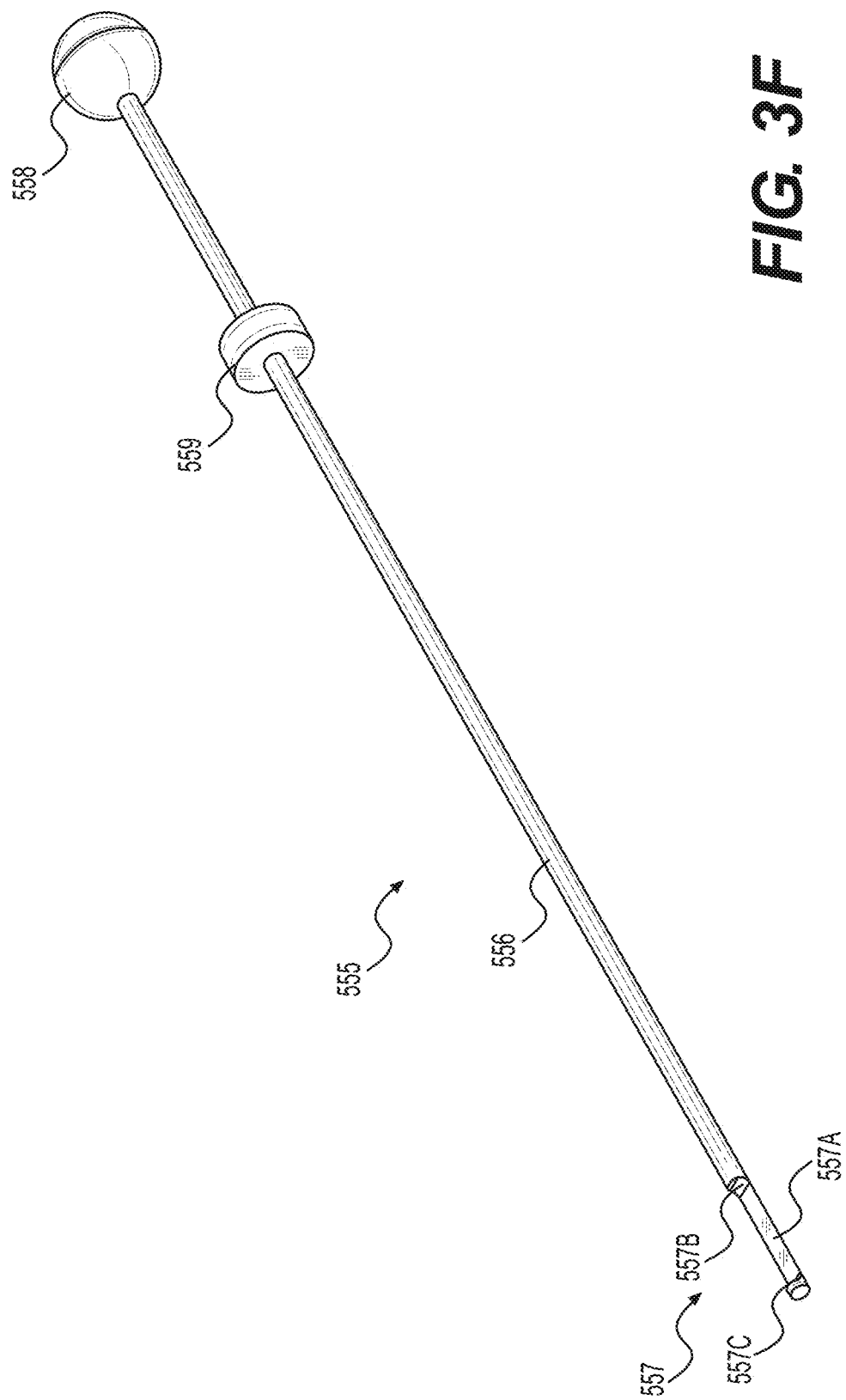

In use, hub 536 may engage power source 700 configured to provide rotational movement of trephine 530. A channel in lamina 16 can be bored out by rotating trephine 530 and incrementally deepening the channel until an anterior aspect of lamina 16 is breached by trephine 530. Fluoroscopic guidance could be used to confirm the depth of trephine 530 relative to lamina 16. Feeler probe 555, as shown in FIG. 3F, can be used to probe the channel to verify that lamina 16 has been breached.

Figure 17:
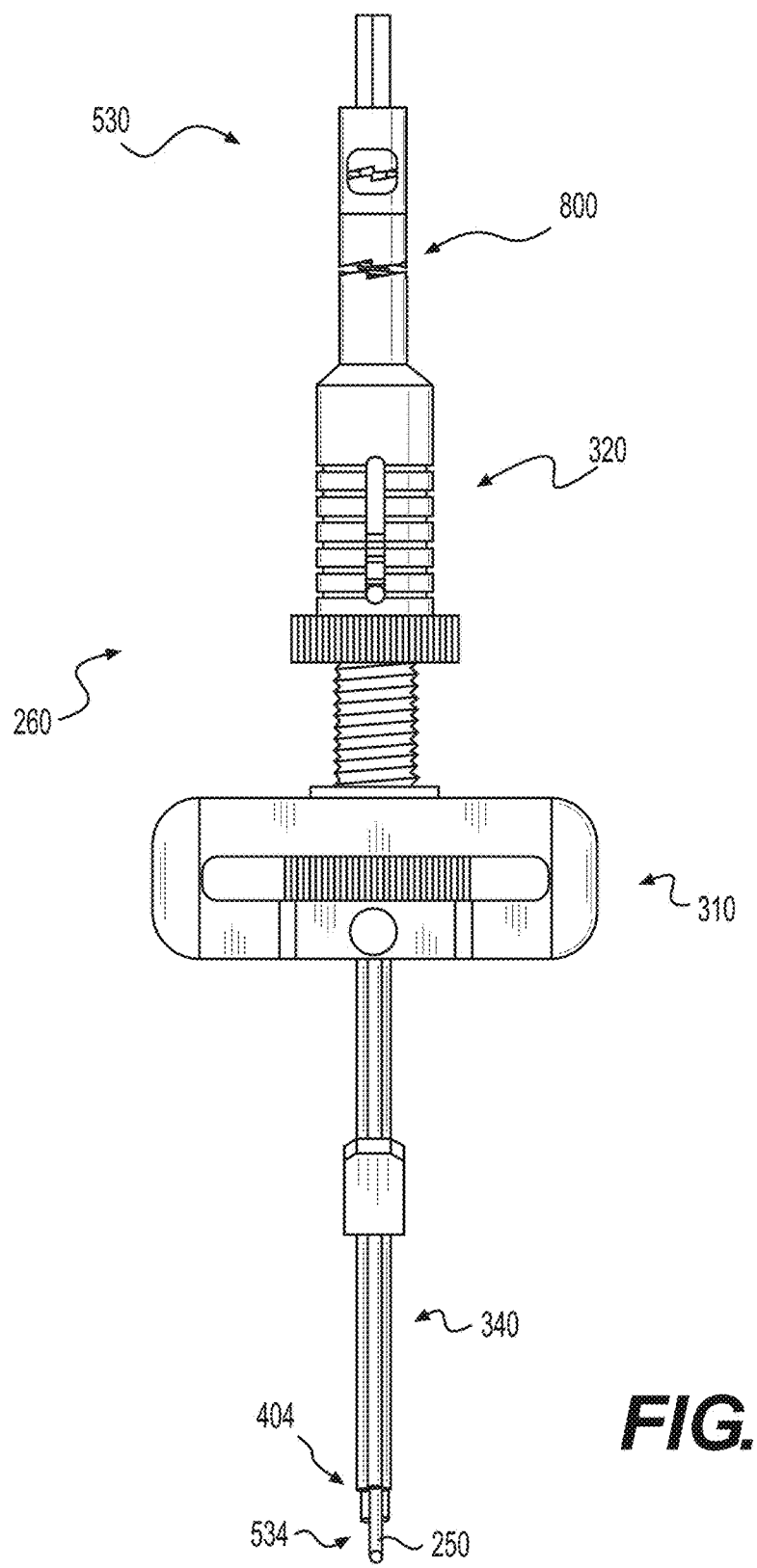
FIG. 17 shows an access portal containing a trephine guide having a clutch, according to an exemplary embodiment.

In some embodiments, a clutch 800 can be used to ensure that trephine 530 does not continue to cut too far beyond an anterior aspect of lamina 16. As shown in FIG. 17, for example, clutch 800 may form part of trephine 530 and couple to access portal 260. The operation of clutch 800 will now be described in detail.

Figure 18A:
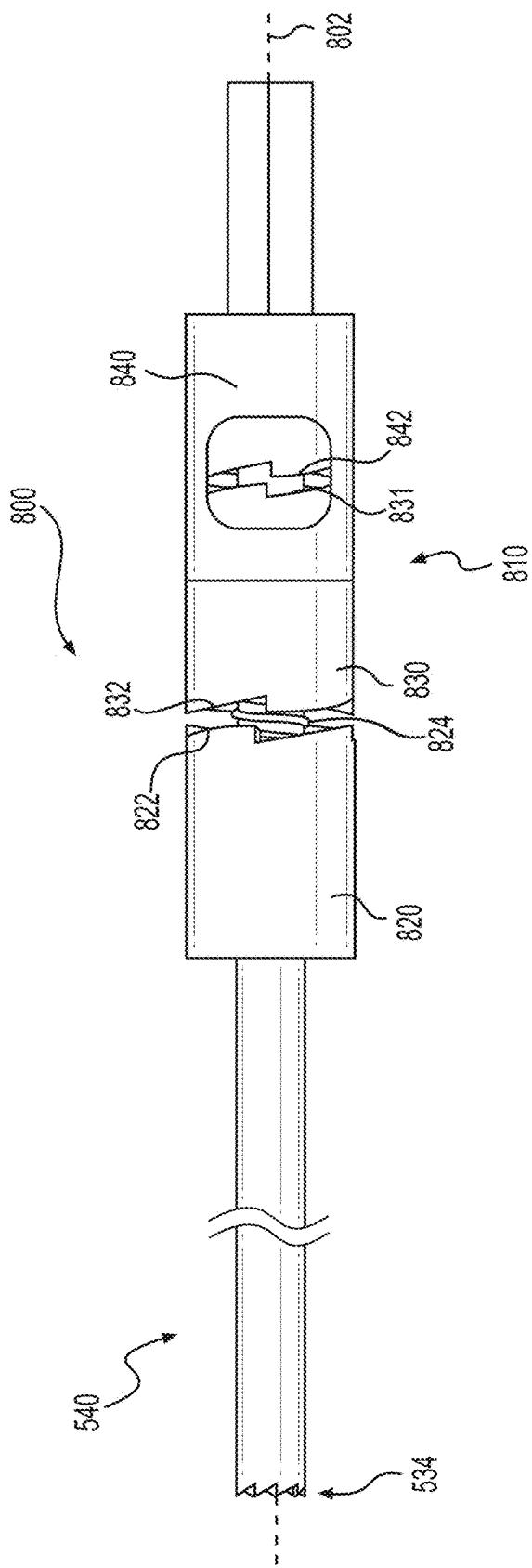
FIGS. 18A, 18B, and 18C show side views of a partially cut-way clutch and trephine, according to an exemplary embodiment.
Figure 18B:
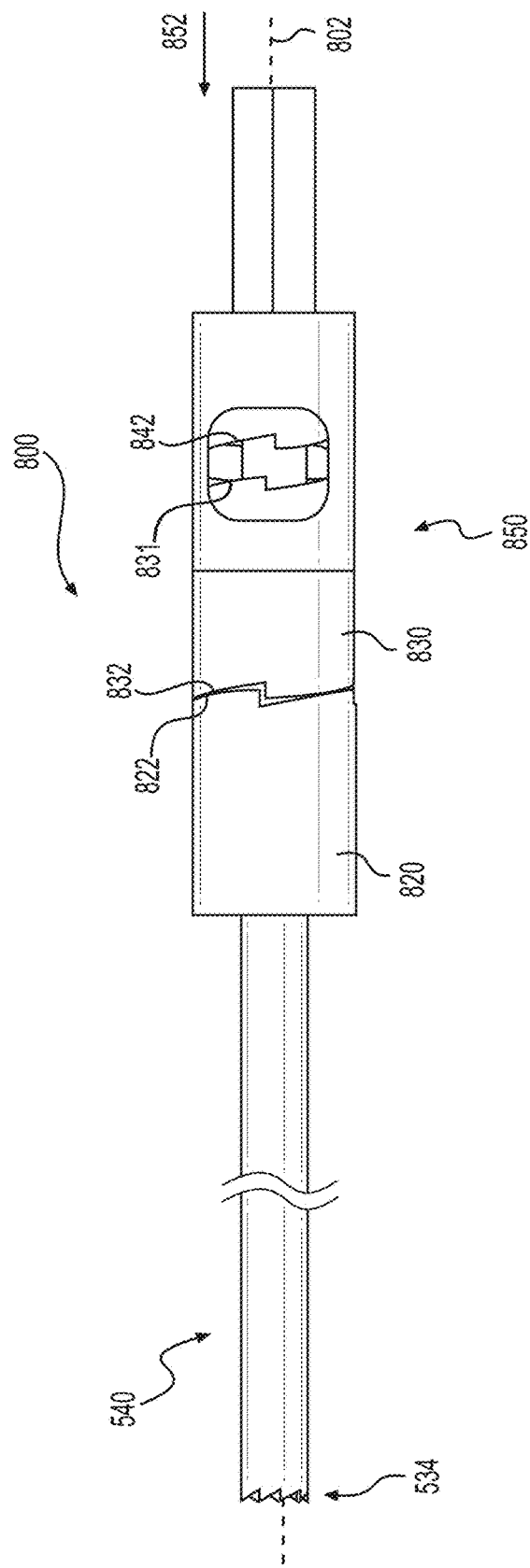
Figure 18C:
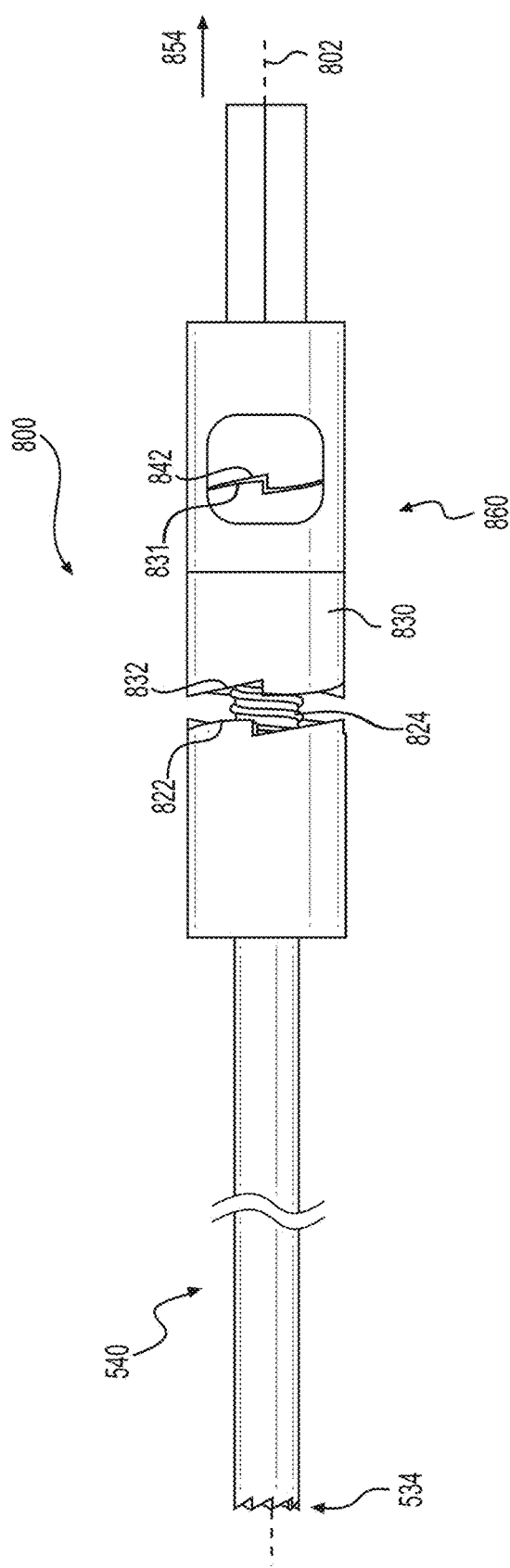
Figure 18D:
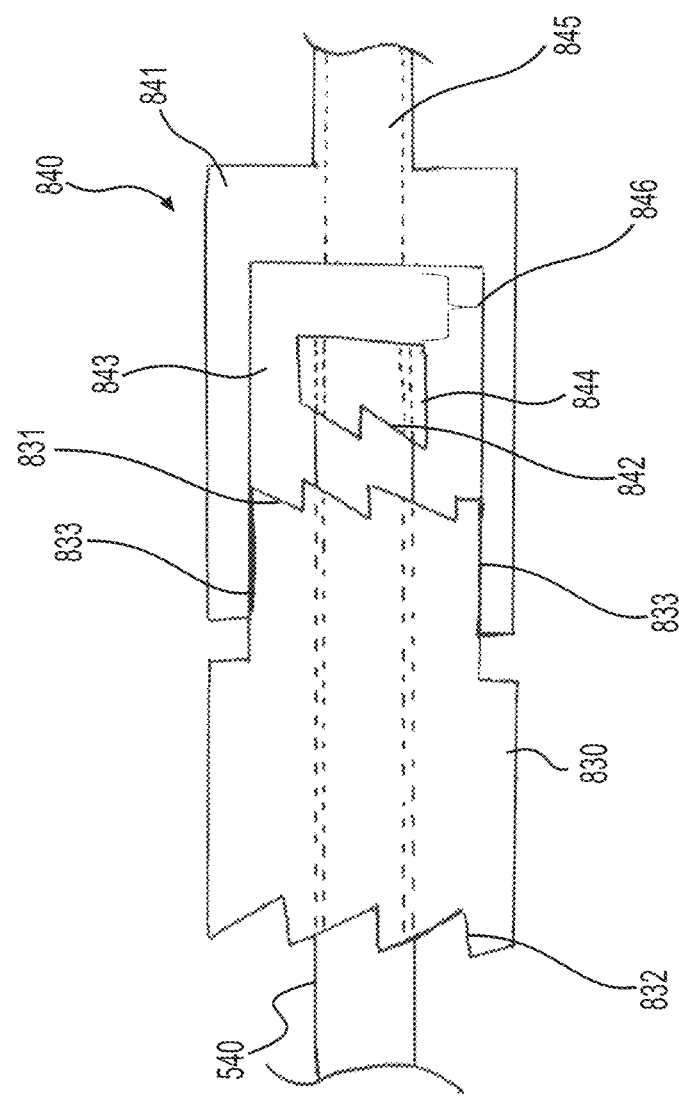
FIG. 18D shows a schematic cross-sectional view of a portion of the clutch in FIGS. 18A-18C.

FIGS. 18A, 18B, and 18C illustrate side views of three different configurations of clutch 800, according to an exemplary embodiment. To assist in explaining the internal components of clutch 800, FIGS. 18A-18C include a cut-away window such that some of the internal structures may be seen. Additionally, FIG. 18D depicts a schematic cross-sectional view of a portion of clutch 800 providing additional detail. Clutch 800 can include a two-way clutch mechanism whereby rotational movement may be transmitted when clutch 800 is compressed and tensioned. Clutch 800 could also include a one-way clutch mechanism to transmit rotational movement in one of compression or tension.

FIG. 18A shows clutch 800 in a neutral configuration 810, wherein rotation of hub 536 (coupled to or integral with proximal end of proximal member 840) is not transferred into rotational movement of elongate member 540. Clutch 800 may achieve neutral configuration 810 when no compressive or tensile forces are applied to hub 536 or elongate member 540 along a longitudinal axis 802.

Clutch 800 may generally comprise a proximal member 840, an intermediate member 830, and a distal member 820. As can be best be seen in FIG. 18D, proximal member may comprise an outer member 841 (e.g., an elongate tubular or cylindrical element) comprising a cavity 843 and an inner member 844 (e.g., a tubular or disc-shaped element) comprising a coupling element 842. Inner member 844 may be housed or otherwise positioned within cavity 843 of outer member 841 may move proximally and distally within cavity 843. In some configurations, there may be a gap 846 between a proximal end of inner member 844 and a proximal end of cavity 843. A proximal end of outer member 841 may be fixedly coupled to or formed integrally with hub 536 (depicted in FIG. 16), and a proximal region of outer member 841 may comprise a lumen therethrough, which may fluidly couple a proximal end of hub 536 and the proximal surface of cavity 843. Inner member 844 may be fixedly coupled to a proximal end of elongate member 540 (e.g., a proximal end of elongate member 540 may be fixed within a lumen of inner member 844). Inner member 844 and elongate member 540 may be attached using any suitable means, for example, welding (e.g., laser welding), a press-fit connection, adhesive, a mechanical connection (e.g., screwed), a combination thereof, or the like. Inner member 844 may comprise a coupling element 842 on a distal end thereof, which as described in more detail below, may be configured to mate, engage, or otherwise releasably couple with a corresponding coupling element on intermediate member 830.

Intermediate member 830 may comprise a proximal end, a distal end, and a lumen therethrough. In some variations, intermediate member 830 may comprise a tubular or cylindrical element. Intermediate member 830 may comprise a first coupling element 831 on a proximal end thereof and a second coupling element 832 on a distal end thereof. The first coupling element 831 may be configured to mate, engage, or otherwise releasably couple with coupling element 842 on inner member 844 of proximal member 840, while the second coupling element 842 may be configured to mate, engage, or otherwise releasably couple with a corresponding coupling element on distal member 820 (not depicted in FIG. 18D, see FIG. 18A). Moreover, intermediate member 830 may comprise a proximal region with a first diameter and a distal region with a second, larger diameter. A proximal portion 833 of proximal region of intermediate member 830 may be positioned within a distal portion of cavity 843 of outer member 841, and may be fixedly coupled thereto using any suitable means, for example, welding (e.g., laser welding), a press-fit connection, adhesive, a mechanical connection (e.g., screwed), a combination thereof, or the like. The second diameter of intermediate member 830 may be larger than the first diameter, and in some variations, may be equal to a diameter of the proximal and distal members 840, 820. Elongate member 540 may be slidably positioned within a lumen of intermediate member 830, such that it may move freely (e.g., translate, rotate) within intermediate member 830.

Distal member 820 may also comprise a proximal end, a distal end, and a lumen therethrough. Proximal end of distal member 820 may comprise coupling element 822, which may be configured to mate, engage, or otherwise releasably couple with coupling element 832 on distal end of intermediate member 830. Elongate member 540 may be positioned within lumen of distal member 820, and distal end (or a distal end portion) of distal member 820 may be fixedly coupled to elongate member 540 using any suitable means, for example, welding (e.g., laser welding), a press-fit connection, adhesive, a mechanical connection (e.g., screwed), a combination thereof, or the like. As will be described in more detail below, clutch 800 may further comprise a spring 824, which may circumferentially surround elongate member 540 and may be positioned between intermediate member 830 and distal member 820.

Proximal, intermediate, and distal members 840, 830, 820 may be formed of any suitable material. In some variations, proximal, intermediate, and/or distal member 840, 830, 820 may be formed from brass and/or stainless steel and elongate member 540 may comprise a stainless steel rod or tube.

As mentioned above, coupling elements 822, 832, 831, and 842 may be configured to selectively engage to permit transmission of rotational movement. In some variations, for example, as shown in FIGS. 18A-18D, coupling members 822, 832, 831, and 842 may each include a set of one way teeth. The teeth may be angled or ramped. The teeth may act as gears that can transmit rotation in a first direction, e.g., clockwise, and limit rotational transfer in a second direction, e.g., anticlockwise. Various other cogs, belts, plates, and fluids could be configured to provide selective rotational transmission.

Clutch 800 may comprise a neutral configuration 810 (depicted in FIG. 18A), a first engaged configuration 850 (depicted in FIG. 18B), and a second engaged configuration 860 (depicted in FIG. 18C). In the neutral configuration 810, distal member 820, intermediate member 830, and proximal member 840 may be generally free to rotate independently of some of the other clutch members. For example, any rotational movement of inner member 844 of proximal member 840 may not be transferred to intermediate member 830, and any rotational movement of distal member 820 may not be transferred to intermediate member 830. Consequently, proximal and distal members 840, 820 may be free to rotate relative to one another. In the first engaged configuration 850, distal and intermediate members 820, 830 may become engaged such that selective rotation of hub 536 rotates elongate member 540. In the second engaged configuration 860, inner member 844 of proximal member 840 may become engaged with intermediate member 830 such that selective rotation of hub 536 may be transmitted to elongate member 540.

Neutral configuration 810 may be achieved by biasing one or more members (e.g., distal member 820, intermediate member 830) of clutch 800. One or more springs may be used to selectively bias one or more clutch members relative to each other or clutch 800. For example, as depicted in FIG. 18A, in neutral configuration 810, spring 824 may bias distal member 820 and intermediate member 830 away from one another. While depicted positioned between distal member 820 and intermediate member 830, in some variations, spring 824 may be positioned in gap 846 between inner member 844 and outer member 841 of proximal member 840. In yet other variations, clutch 800 may comprise a plurality of springs, for example, a first spring positioned between distal member 820 and intermediate member 830 and a second spring positioned within gap 846 between inner member 844 and outer member 841. Spring 824 may be any type of spring, for example, a flat spring, a coil spring, or the like. It is also contemplated that another type of biasing mechanism could be used, such as, for example, a washer, an elastomer, or a similar device.

FIG. 18A illustrates clutch 800 in the neutral configuration 810. As can be seen there, coupling member 822 on distal member 820 is disengaged or spaced apart from coupling member 832 on distal end of intermediate member 830. Additionally, coupling member 831 on proximal end of intermediate member 830 is disengaged or spaced apart from coupling member 842 on inner member 844 of proximal member 840.

FIG. 18B illustrates clutch 800 in the first engaged configuration 850, wherein a compressive force 852 (indicated by arrow 852) is applied to hub 536 (not depicted) on proximal end of proximal member 840. When force 852 is applied, force may be transmitted through outer member 841 of proximal member 840 to the proximal portion 833 of intermediate member 830 through the connection of outer member 841 and intermediate member 830. Inner member 844 may move proximally toward proximal surface of cavity 843 of outer member 841. This may decrease the gap 846 formed between proximal surface of cavity 843 and inner member 844 such that a proximal end of inner member 844 abuts, contacts, or otherwise temporarily couples with proximal surface of cavity 843, and thus outer member 841. Thus, the force 852 may move outer member 841 distally toward inner member 844, and intermediate member 830 distally toward distal member 820, which may collapse or compress spring 824. Coupling members 832 and 822 may then become engaged. Once coupling members 832 and 822 are engaged, rotation of hub 536 may be transferred to elongate member 540 through the fixed connection of elongate member 540 and distal member 820. As explained above, rotational transfer can be one-way. In other embodiments, clockwise or anticlockwise movement could be transferred.

FIG. 18C illustrates clutch 800 in a second engaged configuration 860, wherein a tensile force 854 (indicated by arrow 854) is applied to hub 536 (not depicted) on proximal end of proximal member 840. When force 854 is applied, force may also be transmitted through outer member 841 of proximal member 840 to the proximal portion 833 of intermediate member 830 through the connection of outer member 841 and intermediate member 830. The force 854 may move intermediate member 830 proximally toward inner member 844 of proximal member 840, and coupling members 831 and 842 may engage. Once coupling members 831 and 842 are engaged, rotation of hub 536 (not depicted) coupled to proximal end of outer member 841 may be transmitted to elongate member 540.

In operation, clutch 800 can provide a safety feature to limit rotation of distal end 534 after distal end 534 passes through lamina 16. Initially, compression force 852 can be applied to drill trephine 530 through lamina 16. When compression is applied, clutch 800 can assume configuration 850 as shown in FIG. 18B. Specifically, clutch 800 can transfer rotational movement when distal end 534 is in contact with bone or encounters a certain level of force opposing compression force 852. Such forces on distal end 534 can be encountered as trephine 530 is drilling through bone. Configuration 850 permits trephine 530 to drill through bone.

Once distal end 534 exits a surface or aspect of a bone, a force acting on distal end 534 and opposing compression force 852 can significantly decrease. The reduced force can permit clutch 800 to assume neutral configuration 810 (FIG. 18A). With members 820, 830 disengaged, elongate member 540 may no longer rotate relative to hub 536. Reducing rotation of distal end 534 limits the cutting action of trephine 530, reducing the risk of inadvertently cutting much beyond lamina 16. Such inadvertent cutting could damage tissue located about lamina 16. For example, spinal cord 28 or other nerve tissue, such as, exiting nerve roots.

To then retract elongate member 540 from a bone structure, tensile force 854 can be applied to hub 536. As shown in FIG. 18C, intermediate member 830 and inner member 844 of proximal member 840 can engage. Such engagement can permit transfer of rotational movement from hub 536 to elongate member 540, allowing a surgeon to more easily remove elongate member 540 from the bone structure.

In some embodiments, clutch 800 could include a one-way clutch. That is, have only one engagement configuration, such as, for example, as shown in FIG. 18B. It is also contemplated that trephine 530 could include additional features to facilitate insertion or extraction of elongate member 540 into or from a bone structure. For example, elongate member 540 could include a thread, surface feature, taper, or lubricous coating to aid insertion or extraction. In addition, clutch 800 could include a pin, button, cam or similar device configured to provide an "active" reverse clutch, as opposed to the passive reverse clutch described above and shown in FIG. 18C.

Bone ejector 550 (FIG. 3E) can be configured for placement within the lumen of elongate member 540 of trephine 530 and may be used to push or otherwise remove bone captured within trephine 530. Bone ejector 550 may comprise an elongate member 552 (e.g., a solid rod, a sleeve) and a handle or knob 554. In some variations, the elongate member 552 may comprise a lumen therethrough, but need not. The elongate member 552 may be coupled to the handle or knob 554 at a proximal end thereof such that a user may apply force to bone ejector 550 using handle 554 to advance (e.g., slide or push) bone ejector 550 relative to trephine 530 to remove bone within trephine 530. For example, a user may push on handle 554 while the bone ejector 550 is positioned within the lumen of the trephine 530 such that the elongate member 552 contacts bone captured within lumen of trephine 530 and removes it therefrom. In some variations, bone ejector 550 may further comprise a spring (e.g., along a length of elongate member 552, between handle 554 and elongate member 552), which may assist in circumstances in which bone is difficult to remove from trephine 530. In some variations, the spring may be pre-loaded. While depicted as a separate tool, in some variations, bone ejector 550 may be integrated into or integral with the trephine 530.

Feeler probe 555 (FIG. 3F) may comprise an elongate member 556 with a recess 557 in a distal end region thereof, a handle or knob 558 coupled to a proximal end of elongate member 556, and a stopper 559, positioned between the handle 558 and the recess 557. A distal end surface of the elongate member 556 may be blunt or otherwise atraumatic. The recess 557 may comprise a flat central surface 557A transverse (e.g., substantially perpendicular) to the distal end surface of the elongate member 556, a curved proximal side surface 557B, and a curved distal side surface 557C, and may be configured to at least partially engage a surface of lamina 16. As mentioned above, feeler probe 555 may be used to confirm that an anterior surface of lamina 16 has been breached, for example, by contacting distal side surface 557B of recess 557 with an underside or edge of lamina 16 within channel 60. In some variations, recess 557 may have a length of between about 1.96 cm (0.77 inches) and about 3.00 cm (1.18 inches), between about 2.00 cm (0.79 inches) and about 2.7 cm (1.06 inches), or between about 2.3 cm (0.91 inches) and about 2.7 cm (1.06 inches). In some instances, recess 557 may have a length of about 2.54 cm (1.00 inch). Additionally, in some variations, recess 557 may have a maximum depth of between about 1.5 mm (0.06 inches) and about 2.8 mm (0.11 inches), between about 2.00 mm (0.08 inches) and about 2.7 mm (0.106 inches), or between about 2.3 mm (0.09 inches) and about 2.6 mm (0.102 inches). In some variations, recess 557 may have a maximum depth of about 2.5 mm (0.98 inches).

Stopper 559 may be positioned along elongate member 556 such that it prevents the distal end of elongate member 556 from advancing distally beyond or otherwise protruding from a distal end of trephine 530 beyond a specified distance, which may assist in preventing nerve root damage. For example, in some variations, stopper 559 may be positioned such that it prevents the distal end of elongate member 556 from protruding more than about 1.27 mm (0.05 inches), 3.05 mm (0.12 inches), or between about 1.27 mm (0.05 inches) and about 3.05 mm (0.12 inches inches) from the distal end of trephine 530. In some variations, the distal end of elongate member 556 may protrude about 2.27 mm (0.09 inches) from the distal end of trephine 530. Stopper 559 may have any suitable form, for example, it may comprise a disk-shaped or cylindrical element circumferentially surrounding elongate member 556. Stopper 559 may be formed separately from the elongate member 556 and may be coupled thereto, or it may be integrally formed with elongate member 556.

Figure 19:
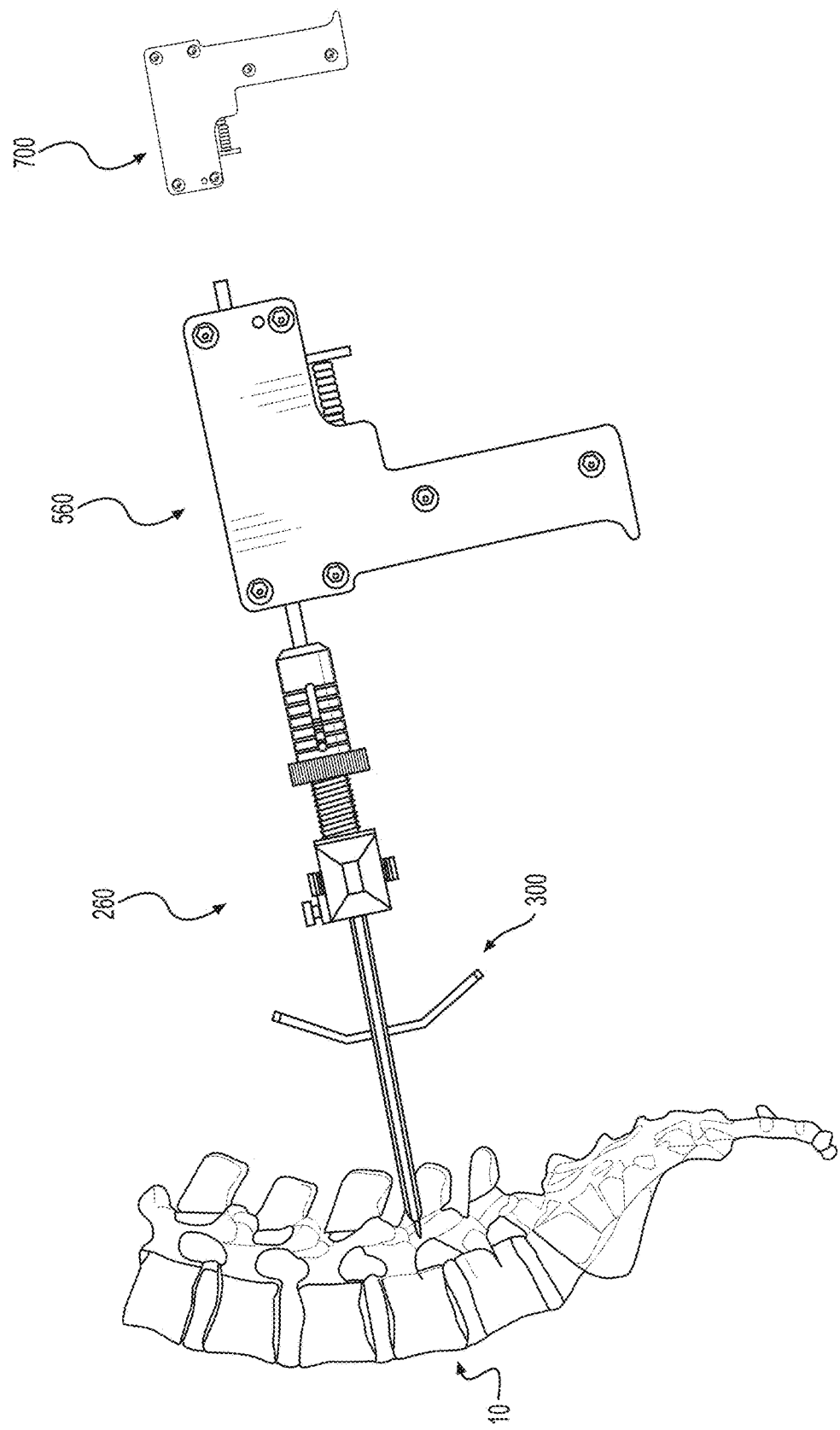
FIG. 19 shows an access portal containing a rotating rongeur attached to a vertebra and separate from a power source, according to an exemplary embodiment.

Following the formation of a suitable channel in vertebra 10 and the removal of trephine 530 from access portal 260, rongeur 560 may be placed within access portal 260, as shown in FIG. 19. In some embodiments, one or more cutting or anchoring components of rongeur 560 can be configured to rotate. Rotational movement can be provided by power source 700.

Figure 20:
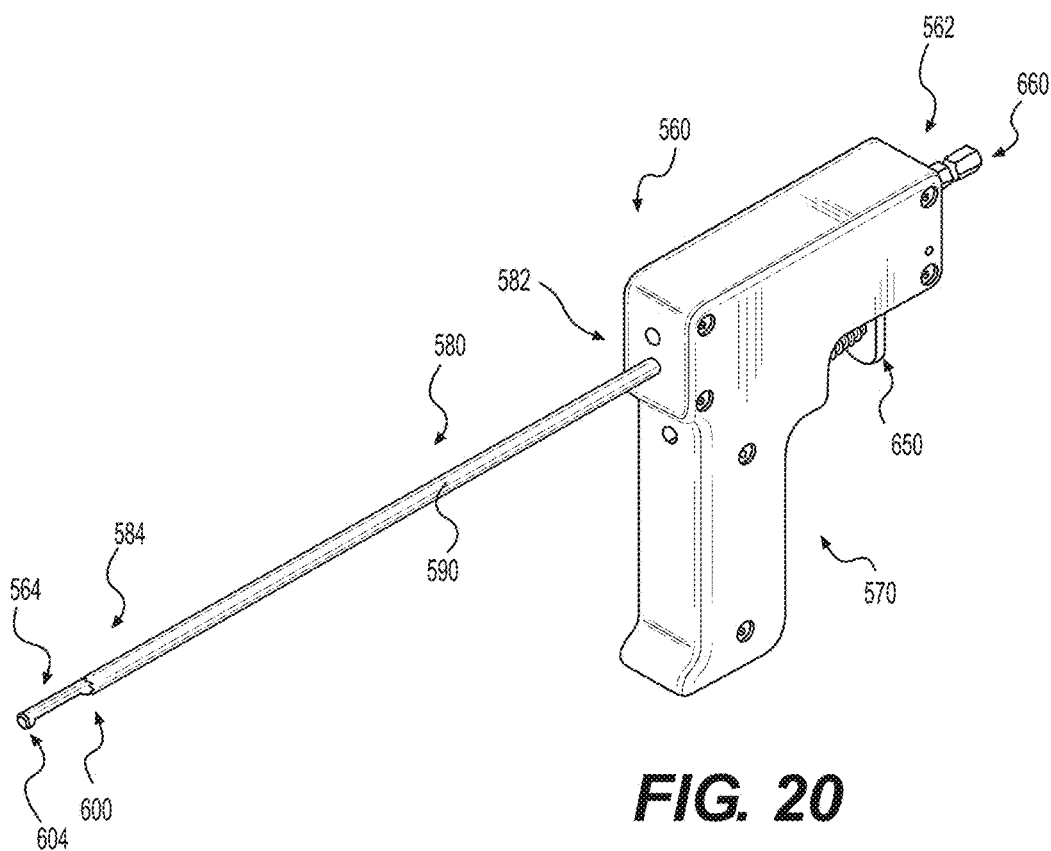
FIG. 20 shows a rongeur, according to an exemplary embodiment.

FIG. 20 depicts rongeur 560, according to an exemplary embodiment. Rongeur 560 can include a proximal end 562 and a distal end 564. Rongeur 560 can also include a hub 660, a handle 570, and a shaft 580. Hub 660 can releasably couple with power source 700 (FIG. 19). Shaft 580 can include a proximal end 582, a distal end 584, and a lumen 590 extending generally from distal end 584 to proximal end 582. Distal end 584 can include serrated teeth. In some embodiments, distal end 584 can be configured to cut bone.

Rongeur 560 can also include a rod 600 configured to at least partially reside within lumen 590. Relative movement can occur between rod 600 and lumen 590. As explained below, rod 600 and shaft 580 can move longitudinally and/or rotationally relative to each other. For example, shaft 580 can rotate and move longitudinally relative to handle 570 while rod 600 remains stationary relative to handle 570. Rod 600 can include a distal end 604 configured to anchor bone, such as, for example, vertebra 10. Rongeur 560 could also include clutch 800 as described above.

Figure 21:
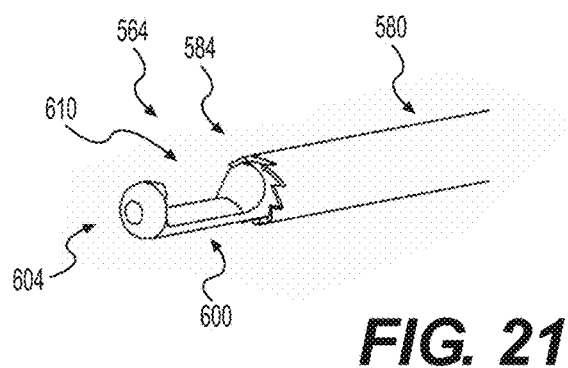
FIG. 21 shows an enlarged view of a distal end of a rongeur, according to an exemplary embodiment.

FIG. 21 depicts an enlarged view of distal end 564 of rongeur 560, according to an exemplary embodiment. As shown, distal end 604 of rod 600 may extend beyond distal end 584 of shaft 580. Rod 600 may also include a recess or cavity 610 configured to anchor to tissue or capture tissue, such as, for example, bone.

Figure 22A:
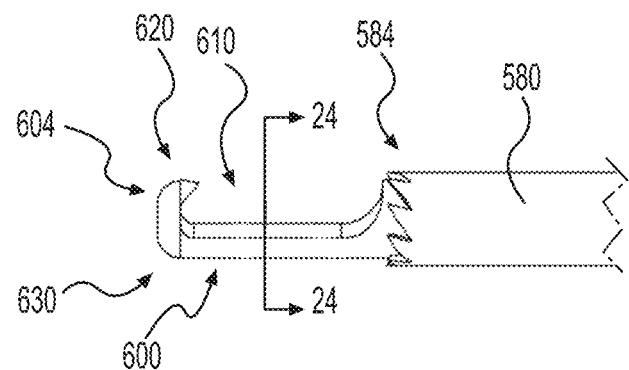
FIG. 22A shows an enlarged side view of a distal end of a rongeur in an open configuration, according to an exemplary embodiment.
Figure 22B:
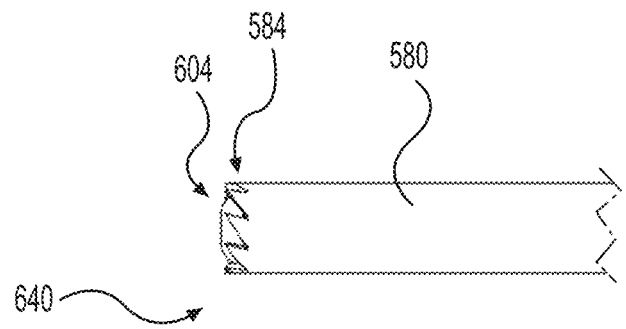
FIG. 22B shows an enlarged side view of a distal end of a rongeur in a closed configuration, according to an exemplary embodiment.

In operation, distal end 584 can move relative to distal end 604. As shown in FIG. 22A, distal end 584 can be located proximal to distal end 604. Such an "open configuration" 630 can expose cavity 610 to surrounding tissue such that tissue may be anchored or captured by rongeur 560. Distal end 584 may move relative to distal end 604 such that cavity 610 is at least partially enclosed by shaft 580, as shown in FIG. 22B. This may represent a "closed configuration" 640 of rongeur 560.

Figure 24:
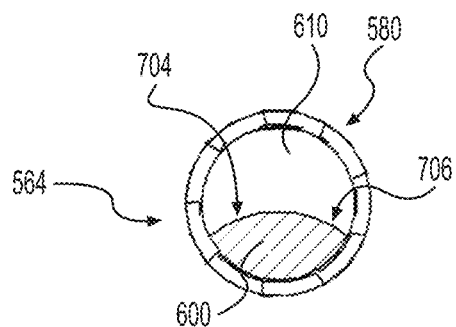
FIG. 24 depicts a cross-sectional view of a distal end of a rongeur, according to an exemplary embodiment.

In some embodiments, relative movement between rod 600 and shaft 580 can function to capture tissue within cavity 610. FIG. 24 shows a cross-sectional view of cavity 610, wherein cavity 610 can be surrounded by rod 600 or shaft 580. As explained below, relative movement between rod 600 and shaft 580 can capture bone within cavity 610.

In some instances, rongeur 560 can be configured to cut bone. For example, shaft 580 may include a sharp edge, a serrated surface, or other feature configured to cut bone. Rongeur 560 can also be configured to anchor to a boney structure. For example, rod 600 can include a hook 620, or similar structure, configured to at least partially anchor to bone tissue. Bone could be anchored using a proximal or a distal end of cavity 610. In addition, rongeur 560 can be configured to both cut and anchor bone. For example, rongeur 560 can cut or anchor bone using one or more relative movements of cutting or anchoring components of rongeur 560. In other variations, in addition to, or in lieu of bone rongeur 560, other bone and/or tissue removal devices may be used to remove bone using a different mechanism, such as ultrasound, a laser, a water jet device, or a wire saw (e.g., a flexible wire (or plurality of wires twisted or otherwise coupled together) with a handle on each end).

Rongeur 560 can include one or more components configured to move relative to one or more other components. For example, shaft 580 may be configured to move longitudinally and/or rotationally relative to rod 600. As shown in FIGS. 22A and 22B, distal end 584 of shaft 580 can move longitudinally relative to distal end 604 of rod 600. In some embodiments, rod 600 can be moved distally or proximally while shaft 580 remains stationary relative to handle 570. In other embodiments, shaft 580 can be moved distally or proximally while rod 600 remains stationary relative to handle 570. In yet other embodiments, both rod 600 and shaft 580 can simultaneously move relative to handle 570.

Rongeur 560 can also be configured to provide rotational movement of one component relative to another component. For example, shaft 580 may be configured to rotate relative to rod 600. Specifically, shaft 580 can be rotated clockwise or anticlockwise while rod 600 remains stationary relative to handle 570.

In some embodiments, rongeur 560 can be configured to provide longitudinal and rotational movements of one component relative to another component. For example, shaft 580 may be configured to move longitudinally and rotate relative to rod 600. In some embodiments, rod 600 can be moved distally or proximally while shaft 580 can be rotated clockwise or anticlockwise. In other embodiments, shaft 580 can be moved distally or proximally and rotated clockwise or anticlockwise while rod 600 remains stationary relative to handle 570.

Various methods of cutting bone can be effective depending on the particular requirements of the surgical procedure and patient anatomy. For example, where relatively low density bone requires removal, axial compression between shaft 580 and rod 600 may be sufficient. In situations where the bone is denser, or hardened, additional mechanical advantage could be obtained by providing rotational movement. If even more force is required, compressive and rotational forces can be applied to aid bone removal.

Longitudinal and/or rotational movement can be controlled using one or more control members. For example, a lever 650 could provide longitudinal movement of shaft 580 relative to rod 600 and a hub 660 could provide rotational movement of shaft 580 relative to rod 600. Lever 650 could be manually operated by a user, using, for example, pressure from a finger or a thumb. Various other types of control members and actuation mechanisms are contemplated. For example, rongeur 560 could be coupled to an electric motor, a pneumatic system, or other mechanism configured to provide relative movement of hub 660. In other embodiments, these powered devices could be integral with rongeur 560. Hub 660 could also be flexible or include a flexible coupling to permit relative movement between rongeur 560 and power source 700 while power source 700 supplies power to rongeur 560.

Figure 23A:
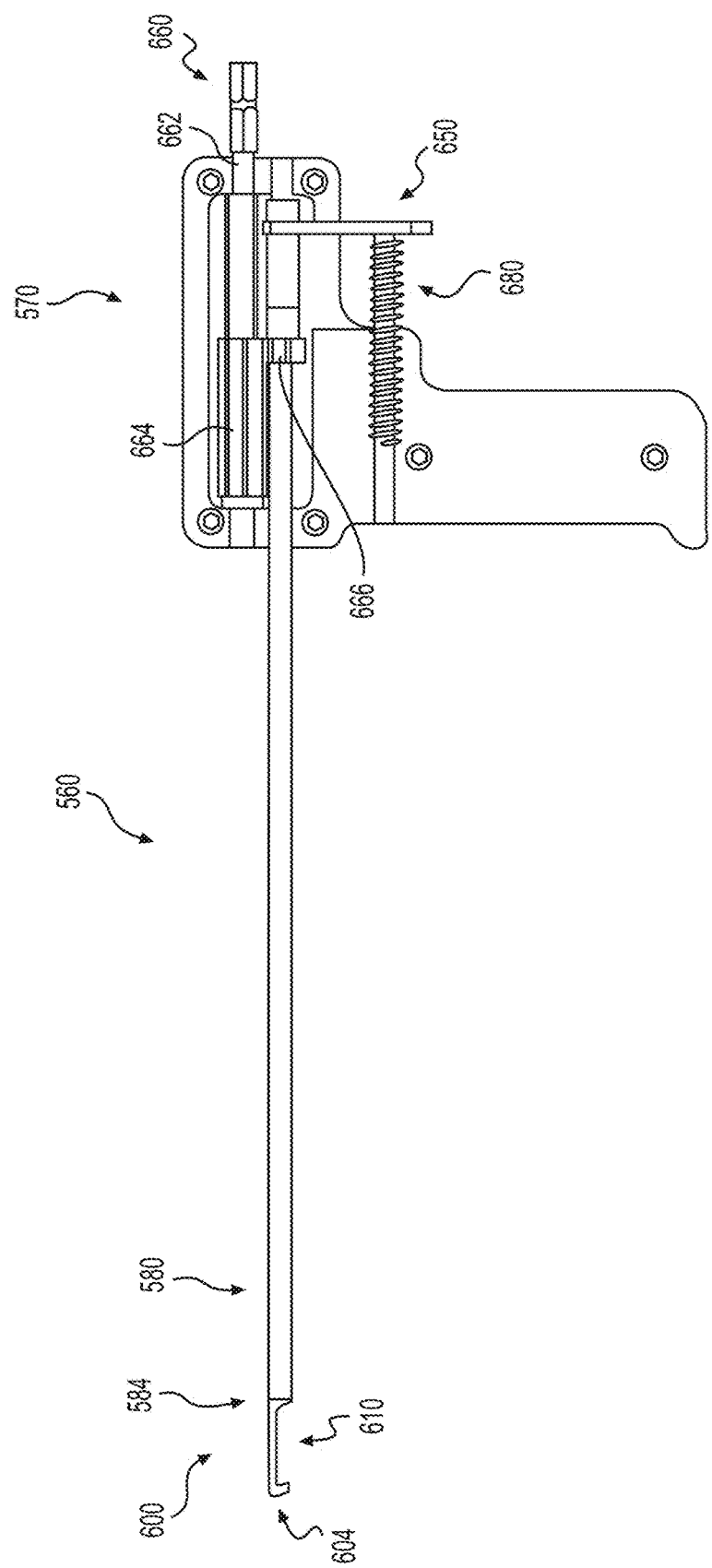
FIG. 23A shows a cross-sectional view of a rongeur, according to an exemplary embodiment.
Figure 23B:
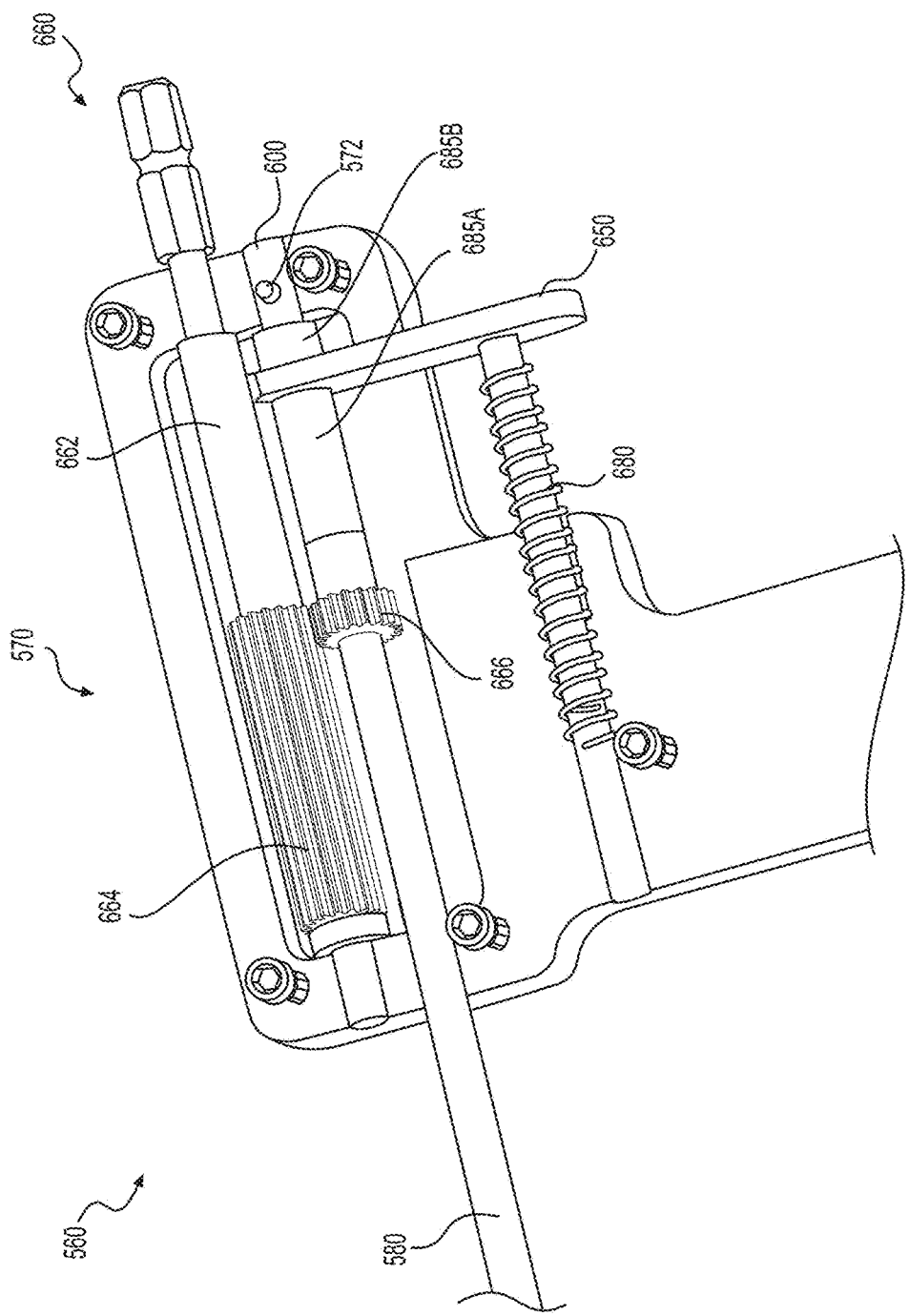
FIG. 23B shows an enlarged cross-sectional view of a rongeur, according to an exemplary embodiment.

FIGS. 23A and 23B depict cross-sectional views of rongeur 560, according to an exemplary embodiment. As shown, shaft 580 can be rotationally coupled to hub 660, wherein both may be configured for rotational movement relative to handle 570. As shown in FIG. 23B, hub 660 can be coupled to a shaft 662 that may include a gear 664. However, hub 660 may be coupled to shaft 580 using any suitable coupling configured to transmit movement. Shaft 580 can include a gear 666. Gears 664, 666 can be configured for rotational and longitudinal movement.

In some embodiments, hub 660 can be rotated by power source 700 (not shown) to rotate shaft 662. Such rotation may cause rotation of gears 664, 666 in one or more ratios. While not shown, gears 664, 666 could include different ratios, a clutch mechanism, or other system configured to regulate transfer of rotational movement.

Gears 664, 666 can also be configured for relative longitudinal movement. For example, lever 650 may be actuated to slide gear 666 in a longitudinal direction relative to gear 664. As explained above, such longitudinal movement can cause relative movement between rod 600 and shaft 580. Specifically, distal end 584 of shaft 580 can move relative to bone anchored in cavity 610 of rod 600.

As shown in FIG. 23A, rod 600 may be fixedly coupled to handle 570 via a fastener 572 (e.g., a pin, screw, bolt, or the like) and lever 650 may be operably coupled to shaft 580 via, for example, spacers 685A, 685B (e.g., sleeves, collars) that may be positioned on either side of a proximal end of lever 650. In other variations, a single spacer may be used and a proximal end of lever 650 may be coupled to the single spacer. Lever 650 may be biased using a spring 680. Lever 650 may be moved via movement of an operator's hand, digit, or other operator action. Other biasing devices are also contemplated, as explained above. Lever 650 may move in one or more directions relative to handle 570. Shaft 580 may be configured to move longitudinally within handle 570 when lever 650 is actuated. In other embodiments, rotational movement of lever 650 may be converted into longitudinal movement of shaft 580 relative to handle 570. Shaft 580 and rod 600 can be variously coupled to handle 570 for relative longitudinal and/or rotational movement. Various other movement mechanisms are contemplated.

Rongeur 560 can be configured to provide tactile feedback to a surgeon during operation. Depressing lever 650 can provide automated rotation and/or longitudinal movement of shaft 580 relative to rod 600 while rod 600 provides anchoring to the underside of lamina 16. In addition, bone can be captured within shaft 580 for removal.

FIG. 24 depicts a cross-sectional view of distal end 564 of rongeur 560, according to an exemplary embodiment. As shown, cavity 610 can be at least partially surrounded by shaft 580 and rod 600. Rod 600 may also include a surface 706 facing toward cavity 610. Surface 706 can be shaped or sized to mimic an engagement profile of part of channel formed in vertebra 10. For example, if a channel formed in vertebra 10 is generally cylindrical, surface 706 may be curved to engage a curved wall of the channel. Specifically, surface 706 may include a curved surface 704 having a radius about equal to half the outer diameter of shaft 580. Such dimensions may assist bone removal, as explained with regard to FIGS. 25A-25C.

Figure 25A:
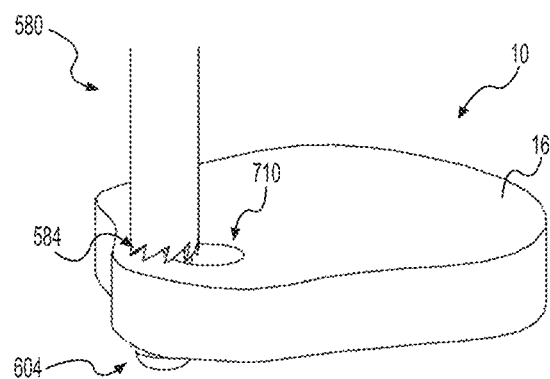
FIG. 25A shows a partial view of a vertebra containing a channel with a rongeur located therein, according to an exemplary embodiment.
Figure 25B:
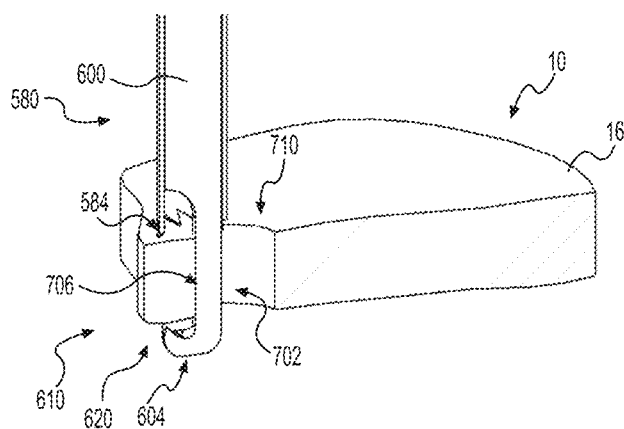
FIG. 25B shows a partial cut-away view of a vertebra containing a channel with a rongeur located therein, according to an exemplary embodiment.

FIG. 25A depicts a portion of vertebra 10 including a channel 710 formed as previously described. Also shown is distal end 584 of shaft 580 located on a posterior surface of vertebra 10, with distal end 604 of rod 600 located on an anterior surface of vertebra 10. FIG. 25B depicts a partial cut-away view of vertebra 10 shown in FIG. 25A, illustrating rod 600 within channel 710. Rod 600 can also include a surface 702 located generally opposite surface 706.

Rongeur 560 can be variously oriented within channel 710. For example, rongeur 560 may be oriented such that cavity 610 is facing toward a lateral boarder of lamina 16. A portion of vertebra 10 can be located within cavity 610 of rod 600, whereby surface 706 of rod 600 can be located to closely engage part of the wall of channel 710.

As previously explained, one or more components of rongeur 560 can move to anchor rongeur 560 within channel 710. For example, rod 600 can move longitudinally relative to shaft 580 to locate a portion of lamina 16 between distal end 584 of shaft 580 and distal end 604 of rod 600. Such anchoring can substantially maintain a position of rongeur 560 while a portion of lamina is cut by rongeur 560.

In some embodiments, hook 620 may contact an anterior surface of vertebra 10. Other features of rongeur 560 may also provide stabilization during cutting of vertebra 10. Such stabilization features should be configured to minimize disruption to surrounding tissue during the resection procedure.

In use, a portion of lamina 16 may be removed by rotating knob 660 in one or more directions, while applying pressure to lever 650 to maintain the position of distal end 604 within channel 710. Multiple passes with rongeur 560 may be required to breach a lateral aspect of lamina 16. Each pass may require removing rongeur 560 from access portal 260 to eject one or more bone fragments. A combination of lateral and anterior-posterior views may be used to verify the position of rongeur 560 or the amount of bone removed.

Figure 25C:
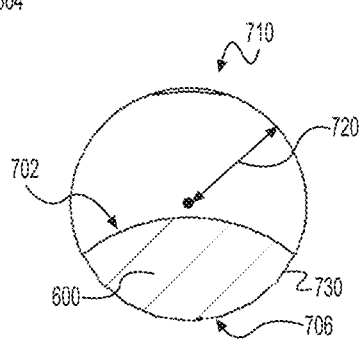
FIG. 25C shows a view into a channel containing a rongeur, according to an exemplary embodiment.

FIG. 25C depicts rod 600 located within channel 710. As shown, surface 706 can be located against part of an inner surface 730 of channel 710. Channel 710 can include a radius 720. Surface 706 can include a radius of curvature substantially similar to radius 720 such that surface 706 can fit against inner surface 730. Because rod 600 can be shaped to engage inner surface 730, the likelihood that rongeur 560 will detach from vertebra 10 during bone removal can be reduced. Thus, rod 600 can be configured to permit better anchoring and engagement with vertebra 10.

In order to enlarge a cross-sectional area of channel 710, to form slot 62 (FIG. 4B), distal end 564 of rongeur 560 may be moved laterally relative to distal end 254 of pin 250 that may be anchored to vertebra 10. Such relative lateral movement can be achieved if third elongate member 340 is displaced laterally relative to first and second elongate members 295A, 295B, permitting increased lateral separation between rongeur 560 and anchored pins 250. Distal end 564 of rongeur 560 can be moved and extended relative to distal end 404 of third elongate member 340 to enlarge channel 710 and for slot 62 if required. Such movement can continue until a boarder of lamina 16 has been breached (FIG. 4B).

FIGS. 26A-D show various slots 62 formed within vertebra 10, using the system of the present disclosure. The relative locations of pins 250 (not shown) in a bone structure are shown at locations 292. As described, it is the lateral movement of third elongate member 340 (and any instrument within third elongate member 340) relative to anchored pins 250 at locations 292 that allows the formation of slots 62 shown in FIGS. 26A-D.

Figure 26B:
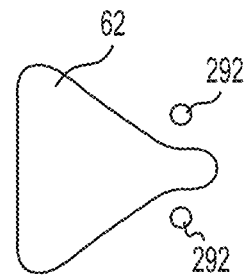
Figure 26C:
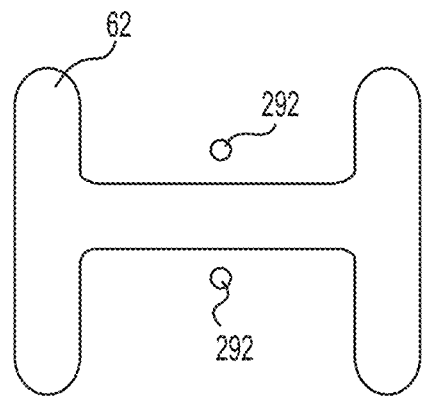
Figure 26D:
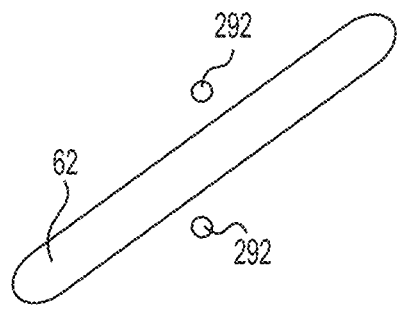

FIG. 26A illustrates slot 62 formed by moving a cutting device laterally in a single direction left and away from pin locations 292. FIG. 26B illustrates slot 62 formed by moving cutting device laterally in more than one direction away from pin locations 292. FIG. 26C illustrates slot 62 formed by moving cutting device laterally in both a left and a right direction away from pin locations 292 and then moving the cutting device in both superior and inferior directions. FIG. 26C illustrates slot 62 formed by moving a cutting device in two directions away from pin locations 292 and angled relative to a lateral plane. Other configurations of slot 62 are also contemplated.

Figure 27:
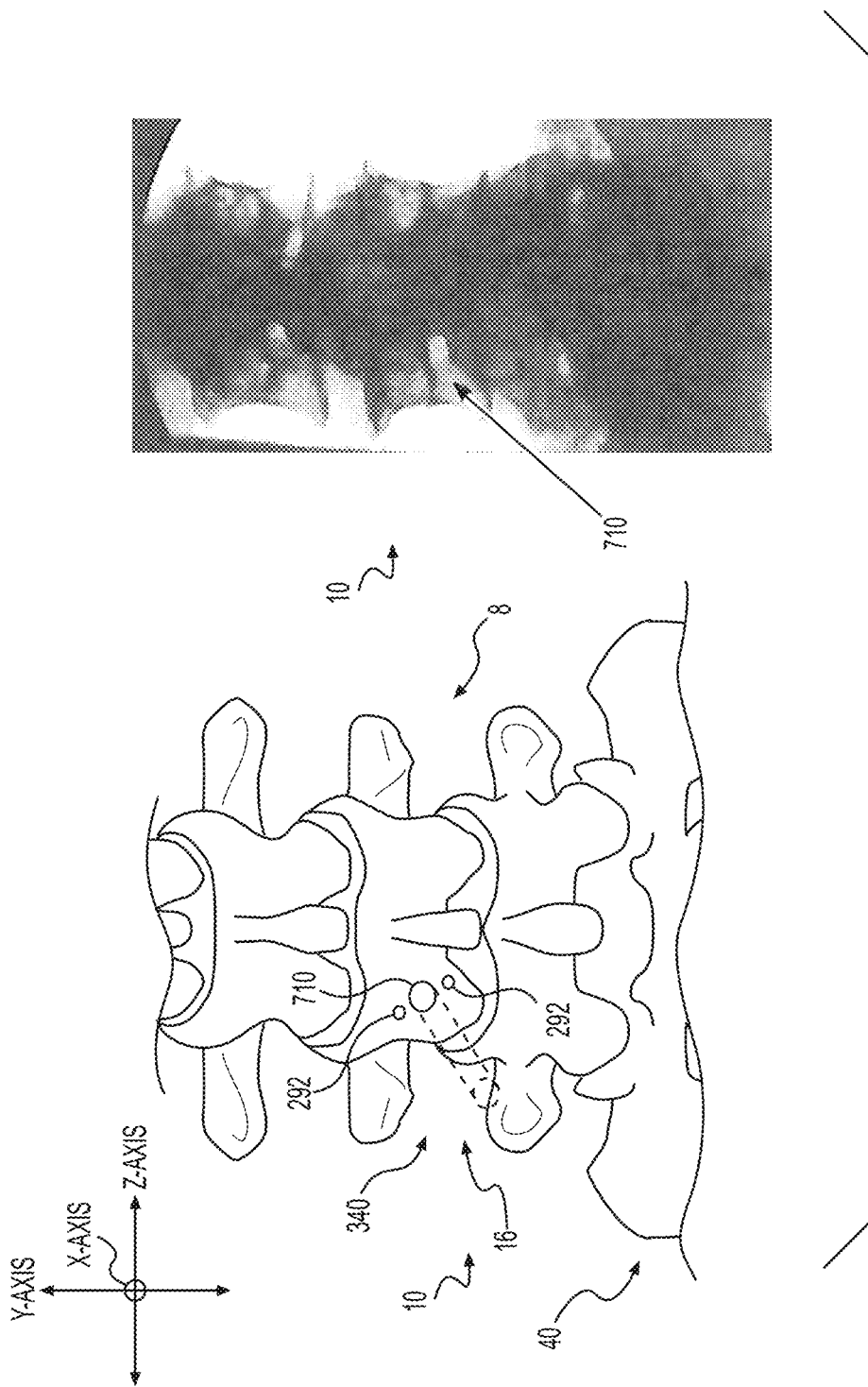
FIG. 27 shows, on the left side, a posterior view of a vertebral column including a vertebra containing a channel and, on the right side, a fluoroscopic image of a posterior view of the vertebral column including a vertebra containing a channel, according to exemplary embodiments.

FIG. 27 shows a posterior image of vertebral column 8 aligned with a fluoroscopic image of vertebral column 8, wherein vertebra 10 has undergone a surgical procedure according to an exemplary embodiment. For purposes of orienting the reader, part of third elongate member 340 is shown with dashed lines and pin locations 292 are shown. The corresponding fluoroscopic image on the right shows channel 710 as a whitened section.

Tilting a C-Arm to an ipsilateral oblique view (approximately 10 degrees off anterior-posterior) may yield a better view. In an anterior-posterior view, bone removal breaching a lateral boarder of vertebra 10 can be verified using fluoroscopy. Feeler probe 555 may also be used to tactilely verify that a lateral border of vertebra 10 has been breached.

In some embodiments, one or more channels 710 can be created in vertebra 10. For example, two channels 710 can be separately created. Following their formation, lateral resection of bone located between the two channels could be used to create single slot 62. Various other modifications to the surgical procedure are also contemplated within the scope of the present disclosure.

Kits

In some embodiments, a plurality of the devices described here may be packaged together as a kit. For example, a kit may comprise any combination of one or more docking pins 250, one or more handles 240 for docking pin(s) 250, an access portal 260, a trephine 530, a bone ejector 550, a feeler probe 555, and a rongeur 560. For example, in some variations, a kit may comprise primary and secondary docking pins, an access portal, and a trephine. In other variations, a kit may comprise a docking pin, an access portal, a trephine and a bone ejector. In yet other variations, a kit may comprise all of the above-mentioned tools, i.e., a docking pin and a handle, an access portal, a trephine, a bone ejector, a feeler probe, and a rongeur. It should be appreciated that a kit may comprise docking pins, handles, access portals, trephines, bone ejectors, feeler probes, and/or rongeurs with any of the features described herein. In some variations, the kit may further comprise instructions for using one or more of docking pin, access portal, trephine, bone ejector, feeler probe and rongeur, and/or instructions for a surgical procedure using one or more of the aforementioned tools. Additionally, in some variations, the kit may comprise one or more K-wires in lieu of or in addition to docking pins 250.

In one embodiment, a kit may comprise an access portal 260 and a trephine 530. Access portal 260 may comprise first elongate member 295A, second elongate member 295B, third elongate member 340, and depth guide adjuster 320. First and second elongate members 295A, 295B may be configured to receive first and second docking pins 250 respectively, and third elongate member 340 may be configured to receive a surgical tool (e.g., trephine 530, bone ejector 550, feeler probe 555, and/or rongeur 560). Trephine 530 may comprise elongate member 540, hub 536, and two-way clutch 800 operably coupling elongate member 540 and hub 536. As described in detail above, rotational movement may be transmitted from hub 536 to a distal end of elongate member 540 through two-way clutch 800 when both a compressive force and a tensile force is applied to hub 536. In some variations, the kit may further comprise bone ejector 550, feeler probe 555, and rongeur 560 and each of the aforementioned tools may be configured to be slidably positioned within third elongate member 340 of access portal 260. In some instances, the kit may further comprise first and second docking pins 250.

In another embodiment, the kits described here may comprise access portal 260, trephine 530, bone ejector 550, feeler probe 555, and rongeur 560, and the access portal 260 may comprise housing 310 and elongate member 340 coupled to the housing 310. In this variation, housing 310 may comprise body 316 and actuator 315, and actuator 315 may be coupled to elongate member 340. In this variation, rotation of actuator 315 in a first direction may lock the position of elongate member 340 relative to body 316 and rotation of actuator 315 in a second, opposite direction may allow lateral movement of elongate member 340 relative to body 316. In some variations, access portal 260 may further comprise first and second docking pin guides or elongate members 295A, 295B, which may be configured to receive first and second docking pins 250. In these variations, rotation of actuator 315 in the second direction may also allow lateral movement of elongate member 340 relative to first and second docking pin guides. Elongate member 340 may be configured to receive at least a portion of trephine 530, bone ejector 550, feeler probe 555, and/or rongeur 560.

Methods

In one embodiment, a surgery or procedure for treating a patient with lumbar spinal stenosis, radiculopathy or spinal condition is provided. The patient selection and one or more treatment sites may be determined based on patient symptoms, clinical effects from local anesthetic and/or steroidal injections, and/or radiographic imaging, including but not limited MRI, CT scan, and fluoroscopic studies, such as an epidurogram. During the procedure, the patient may be positioned on the surgical or procedure table in a prone or lateral decubitis position, with one or both legs in a straight or in a knee-chest position. The patient is then draped and prepped in the usual sterile fashion. Anesthesia may be achieved using local, regional and/or general anesthesia.

The target lamina(e) on the patient may be identified before, during, and/or after the desired anesthesia is achieved, and may be marked with ink and/or an inserted radiographic marker or wire. Fluoroscopy and/or surface landmarks may also be used to identify one or more target laminae. An epidurogram, myelogram, or other nerve highlighting, using contrast media or other suitable material, may be performed under radiography to identify the anatomy. A stab incision may be made in the skin, and optionally extended in a cephalad, caudal, lateral and/or medial direction up to 1 cm, 2 cm, 3 cm or 4 cm, 5 cm or 10 cm in length. The incision may be dissected down to the underlying fascia. A tissue dilator may be used to further dissect the tissue, such as the paraspinal muscles, until the targeted hemilamina is identified. A first docking pins or K-wire may be positioned and inserted into a superior, inferior, medial or lateral region of the hemilamina, followed by the optional positioning and insertion of a second docking pin or K-wire. A mallet and/or a handle instrument may be used to insert the docking pin or K-wire into the lamina, and/or may be detached from the pin or K-wire after insertion. In other variations involving two or more treatment sites, the second pin or K-wire, or any other additional pins or K-wires may be inserted into a different hemilamina that may or may not be adjacent to the first hemilamina. An access cannula or device may then be coupled to the one or more pins or wires, and then is advanced distally along the pin(s) or wire(s) so that the distal tip of the access cannula is in contact or otherwise adjacent to the target location on the hemilamina. The positioning of the access cannula may be confirmed with live fluoroscopy and locked into position using the locking mechanism, e.g. locking screw, if provided on the access cannula system. In some variations, the position and/or orientation of the cannula is confirmed to make sure that the longitudinal path or volume extending distally from the distal end of the cannula does not intersect the superior edge and/or inferior edge of lamina, or the spinous process medial to the target location or the facet joint lateral to the target location. The cannula position and/or orientation may be further adjusted based on the distance from the superior edge, inferior edge, spinous process and/or facet joint of the lamina. An elongate trephine device may be selected and then inserted into the access cannula to create an opening from the posterior surface of the hemilamina through the anterior surface of the hemilamina. In some variations, an opening with a diameter or cross-section dimension of 1 mm, 2 mm, 3 mm, 4 mm, 5 mm, 6 mm, 7 mm, 8 mm, 9 mm, or 10 mm, or between 2 mm to 10 mm, 4 mm to 8 mm, or 5 mm to 10 mm may be formed in the lamina. In some variations, the initial opening may be further supplemented or modified by translating, pivoting and/or longitudinally displacing the access cannula relative to the one or more pins or wires, and removing additional bony material from a cannula position that overlaps or contacted the perimeter of the existing opening. The initial opening may also be modified by removing the trephine and inserting a different trephine or a bone rongeur to remove additional bone or other tissue, with or without moving the access cannula. The bone rongeur or other directional tissue removal tool may also be rotated to remove tissue at different circumferential locations, with or without further displacement of the access cannula. In some examples, an elongate slot in the lamina may be formed using the trephine by laterally translating or pivoting the access cannula along a single movement axis. In other examples, symmetrical enlargement, angled slots, and/or other complex shaped opening or openings may be formed in the lamina by translating, pivoting, and/or rotating the access cannula along two or more movement axes. In other embodiments where repeated trephine usage is performed, each use may be at a lamina position may or may not overlap with one or more other lamina positions. In some further embodiments, a multiple discrete, non-overlapping openings may be formed in a single lamina. In some examples, each of the bone removal locations is located within the boundaries formed by the superior edge and inferior edges of lamina, the spinous process and facet joint of the hemilamina, but in other examples, one or more bone removal location may involve the superior edge and inferior edges of lamina, the spinous process and facet joint of the hemilamina. The removal of bone from any of these four anatomical locations may be pre-planned or may be determined during the procedure based on radiographic imaging, e.g. an epidurogram, myelogram, or other nerve highlighting. Radiographic imaging may be performed before a procedure, during a procedure, and/or after a procedure (e.g., at procedure completion). In some variations, the access cannula may be incrementally moved or translated laterally toward the medial facet joint or superior articular process until or just before bone from the medial facet joint or superior articular process is removed and/or confirmed by imaging.

In one further embodiment, a stab incision of approximately 4 cm, or 2 cm to 5 cm in length is made in the skin and down to the fascia of the overlying the targeted spinal nerve root or impingement site. A dilator is advanced through the overlying muscle until the target hemilamina is reached. A first docking pin is then inserted into a superior location on the hemilamina using a releasably coupled pin handle, which is then decoupled from the first docking pin once the desired insertion depth and location is confirmed. A second docking pin is then inserted into an inferior portion of the hemilamina using the same or different pin handle. The pin handle is then decoupled from the second docking pin. An access instrument in then inserted over the two docking pins, followed by insertion of a trephine through the access instrument. An opening of 6 mm, or in the range of 4 mm to 10 mm or 4 mm to 8 mm, is created in the lamina, and then removed from the access instrument. A rotatable bone rongeur is then inserted into the access instrument to remove bone and/or tissue enlarge the opening toward the lateral recess. The bone rongeur and/or access instrument is moved laterally and the bone and/or tissue removal is repeated until the medial facet joint is undercut. An epidurogram, myelogram, or other nerve highlighting along with fluoroscopy or other imaging modality is performed to confirm decompression of the corresponding impingement site or nerve root by injection of contrast or imaging agent, typically but not always 1 to 2 ml, at the target location to assess agent flow and/or to identify the exiting nerve root. If adequate flow is confirmed, the bone rongeur and access system may be removed, and the targeted location may then be closed at one or more anatomical layers using sutures, staples and/or tissue glue.

In another embodiment, or a further embodiment of the above general methods that include one or more of the features below, the patient may be positioned in on the table, and draped and prepped in the usual sterile fashion. The present disclosure could include the following procedure. Initially, in an Anterior-Posterior view, the lamina to be treated can be identified. A mark may be made on the patient's skin inferior and medial of the pedicle. A longitudinal incision may be made having about 12 mm in length. This incision may include about 6 mm superior incision and about 6 mm inferior extension from the mark, but in other embodiments, may extend 2 mm to 10 mm, or 4 mm to 8 mm in either or both longitudinal directions. Next, a docking pin or K-wire may be tapped to hold an initial position. A C-arm and/or the patient's table may be rotated to a contralateral oblique view and the pin may be pivoted to align it generally perpendicular to the lamina's surface. The desired oblique view or projection may be achieved by positioning the superior articulating process midway or generally between the anterior and posterior aspects of the corresponding vertebral body, such that the endplate of the vertebral body is aligned with the projection axis, e.g. the appearance of the endplate is a single line, or closest to a single line. The pin may then be further inserted or forced down until it reaches the lamina's underside. The docking pin handle, if any, may be removed from the docking pin.

The access portal, including a second pin, may be placed over the docked pin and moved down until the tip of the obturator contacts the surface of the lamina. The second pin may be anchored to the lamina. In some variations, the one or both docking pins may be pre-coupled to the access device and are inserted into the lamina with the access device already coupled. In other variations, a template may be used with the first docking pin to identify the location for the second docking pin, or the position and/or orientation of the access device. The template may comprise an optically transparent material, and may include an opening for the first docking pin and/or second docking pin, and an opening or other indicia to align the template to one or more anatomical features, e.g. a spinous process, articular process, or one or more edges of the lamina. The obturator may then be removed and replaced with a trephine. The teeth of the trephine may contact the lamina surface. Following, the adjuster may be set for a 5 mm gap, or in the range of 3 mm to 7 mm, or 4 mm to 6 mm. Drilling can begin until the trephine reaches the adjuster. Drilling can be continued in 2 mm increments, or in increments in the range of 1 mm to 4 mm, or 2 mm to 3 mm. Drilling may be stopped when the surgeon feels a loss of resistance. If a clutch is used, transmission of movement to the trephine's cutting element may be interrupted. Various mechanisms could be used to indicate disengagement of the clutch, such as, for example, visual, audio, or other types of indicators. The trephine may then be removed from the access portal. Following, a bone ejector rod or plunger can be used to push bone out of the internal diameter of the trephine's cutter.

A feeler probe can be used to confirm that the lamina has been completely cut through. This can include hooking the feeler probe to an underside of the lamina. The pin guide may be slid up to or near the housing, which may permit translation or other movement or displacement of the third elongate member of access device, and the actuator (e.g., dial 315) may be unlocked. The drill may be switched into reverse and attached to the rotating rongeur. The rongeur may be oriented such that the lateral opening of the rongeur is facing the desired cutting direction, e.g. toward the medial facet joint or toward the superior articular process. The rongeur may then be inserted in the access portal until the handle of the rongeur contacts the guide adjuster. Then the lumen containing the rongeur and the rongeur may be slid laterally. The distal end or lateral opening of the rongeur may then be hooked to the underside of the lamina. Once properly hooked, the rongeur may be activated. Bone may be cut by depressing the rongeur's lever with a "pecking action." Cutting may be stopped and the rongeur removed after the end of travel on the actuator plate. Then, the rongeur's cutter may be carefully retracted to collect bone sample. One or more of the above steps may be repeated until the rongeur has cut through an edge of the lamina. The access procedure above may be repeated at or more other locations on the patient, and either ipsilateral or contralateral from the first location.

In some further embodiments, the skin mark or target location may be determined by first obtaining an Anterior-Posterior view of the spine, and adjusting the fluoroscopy arm and/or patient table so that the appearance of the lower endplate of the superior vertebral body is a single line or as close to a single line as possible. Referring back to the AP view, the center of the superior pedicle and the inferior border of the superior pedicle may be identified, and corresponding vertical line and horizontal line, respectively, may be marked on the patient's back. The lateral border of the trephine cannula may be aligned with the medial side of the vertical line, and another vertical line may be drawn approximately 1.5 times the width of the cannula spaced medially from the first vertical line. The superior border of the trephine is also oriented or aligned horizontally inferior to the horizontal line, and a horizontal line is drawn along the inferior border of the trephine cannula. The intersection of the second vertical and horizontal lines is the incision point, and may be additionally marked to avoid or reduce any confusion with the other three intersection points. A separate ruler or other elongate measurement or marking tool with a width that is 1.5 times the diameter of the corresponding trephine cannula may also be provided to draw the second vertical line. In procedure kits or trays that comprise a plurality of different sized trephines, a plurality of corresponding rulers or marking tools may be provided. For example a T, L or X shaped marking tool may be provided that has a 1.5× vertical element and a 1.0× horizontal element to facilitate the marking, and may have indicia on its surface to indicate the superior/inferior and/or medial/lateral directions.

In other variations, the access device and docking pins are not used, and the trephine and rongeurs may be used with a different minimally invasive spinal access system or a manual cannula at the identified incision point. The tools and procedures may also be used with robotic tool holding systems and/or robotic or computer navigation systems such that the skin markings procedures herein are not required, and the imaging modalities of the navigation system are used.

While the embodiments of the present disclosure have been shown and described, modifications thereof can be made by one skilled in the art without departing from the spirit and teachings of the present disclosure. The embodiments described and the examples provided herein are exemplary only, and are not intended to be limiting. Many variations and modifications of the present disclosure described herein are possible and are within the scope of the present disclosure. One or more features of the methods described herein need not be performed in the order listed. Accordingly, the scope of protection is not limited by the description set out above, but is only limited by the claims which follow, that scope including all equivalents of the subject matter of the claims.

What is claimed is:

1. A method of treating lumbar spinal stenosis by at least partially decompressing a compressed nerve root, comprising:
   identifying the compressed nerve root;
   identifying at least one of a center of and an inferior border of a superior pedicle using fluoroscopic imaging;
   percutaneously accessing a region of a lamina located adjacent to the compressed nerve root;
   forming a channel having a longitudinal axis through the region of the lamina, wherein the channel is formed medial to a lateral border of the lamina; and
   laterally extending the channel in at least one direction generally perpendicular to the longitudinal axis of the channel.

2. The method of claim 1, wherein the region of the lamina includes a lateral recess area and wherein the method further includes extending the channel to breach the lateral border of the lamina.

3. The method of claim 1, wherein at least one of forming the channel and laterally extending the channel is performed without direct visualization.

4. The method of claim 1, further including making an incision at the intersection of a vertical line associated with the center of the superior pedicle and a horizontal line associated with the inferior border of the superior pedicle.

5. The method of claim 4, further including inserting a device through the incision, aligning the device substantially parallel to the superior pedicle, and anchoring the device to the lamina at a plurality of anchoring locations.

6. The method of claim 5, wherein forming the channel further includes forming the channel generally between at least two of the plurality of anchoring locations.

7. The method of claim 5, wherein the device comprises an access lumen, and wherein the method further comprises moving the access lumen from a first position to a different position without moving the plurality of anchoring locations.

8. The method of claim 7, wherein the step of moving the access lumen is performed without changing an orientation of the access lumen.

9. The method of claim 7, wherein the access lumen is restricted to a linear movement substantially orthogonal to the longitudinal axis of the channel.

10. The method of claim 7, further comprising releasably engaging a lock to maintain one of the positions of the access lumen relative to the plurality of anchoring locations.

11. The method of claim 1, further comprising anchoring a docking pin to the lamina and advancing a device along the docking pin toward the region of the lamina.

12. The method of claim 11, wherein the device comprises first and second elongate members each configured to receive a docking pin and a third elongate member configured to receive a cutting tool, and wherein the method further comprises advancing the cutting tool through a lumen of the third elongate member to the region of the lamina.

13. The method of claim 12, further comprising moving the third elongate member laterally relative to the docking pin anchored to the lamina.

14. The method of claim 1, wherein forming the channel through the region of the lamina further comprises creating an opening in the lamina using a trephine.

15. The method of claim 14, further comprising confirming that the opening traverses an anterior surface of the lamina.

16. The method of claim 14, wherein the trephine comprises a two-way clutch.

17. The method of claim 16, wherein the trephine further comprises an elongate member and a hub, wherein rotational movement is transmitted from the hub to the elongate member through the two-way clutch when a compressive force is applied to the hub and when a tensile force is applied to the hub.

18. The method of claim 17, wherein the two-way clutch comprises a first engaged configuration and a second engaged configuration, wherein the two-way clutch is in the first engaged configuration when the compressive force is applied to the hub and is in the second engaged configuration when the tensile force is applied to the hub.

19. The method of claim 17, wherein the two-way clutch comprises a neutral configuration, a first engaged configuration, and a second engaged configuration, wherein rotational movement is not transmitted from the hub to the elongate member when the two-way clutch is in the neutral configuration.

20. The method of claim 19, wherein the two-way clutch is in the first engaged configuration when the trephine is moving through the lamina to form the opening.

21. The method of claim 20, wherein the two-way clutch transitions to the neutral configuration when a distal end of the trephine exits the lamina.

22. The method of claim 21, wherein the two-way clutch transitions to the second engaged configuration when the distal end of the trephine is retracted through the opening.

* * * * *